US010517820B2

(12) United States Patent
Bellinger et al.

(10) Patent No.: US 10,517,820 B2
(45) Date of Patent: *Dec. 31, 2019

(54) RESIDENCE STRUCTURES AND RELATED METHODS

(71) Applicants: Massachusetts Institute of Technology, Cambridge, MA (US); The Brigham and Women's Hospital, Inc., Boston, MA (US)

(72) Inventors: Andrew Bellinger, Wellesley, MA (US); Shiyi Zhang, Shanghai (CN); Carlo Giovanni Traverso, Newton, MA (US); Robert S. Langer, Newton, MA (US); Stacy Mo, Darien, IL (US); Tyler Grant, Arlington, MA (US); Mousa Jafari, Waltham, MA (US); Dean Liang Glettig, Cambridge, MA (US); Angela DiCiccio, San Francisco, CA (US); Lowell L. Wood, Jr., Bellevue, WA (US); Philip A. Eckhoff, Kirkland, WA (US)

(73) Assignees: Massachusetts Institute of Technology, Cambridge, MA (US); The Brigham and Women's Hospital, Inc., Boston, MA (US); Tokitae LLC, Bellevue, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/379,727

(22) Filed: Apr. 9, 2019

(65) Prior Publication Data

US 2019/0298652 A1 Oct. 3, 2019

Related U.S. Application Data

(63) Continuation of application No. 16/177,704, filed on Nov. 1, 2018, which is a continuation of application
(Continued)

(51) Int. Cl.
| | | |
|---|---|---|
| A61K 9/00 | (2006.01) | |
| A61K 9/48 | (2006.01) | |
| C08G 18/73 | (2006.01) | |
| C08G 63/08 | (2006.01) | |
| C08G 18/42 | (2006.01) | |
| A61K 47/58 | (2017.01) | |
| A61K 47/69 | (2017.01) | |
| A61K 31/357 | (2006.01) | |
| A61K 31/65 | (2006.01) | |
| A61K 31/7048 | (2006.01) | |
| C08G 83/00 | (2006.01) | |

(Continued)

(52) U.S. Cl.
CPC .......... *A61K 9/0065* (2013.01); *A61K 9/0053* (2013.01); *A61K 9/48* (2013.01); *A61K 31/357* (2013.01); *A61K 31/65* (2013.01); *A61K 31/7048* (2013.01); *A61K 47/10* (2013.01); *A61K 47/32* (2013.01); *A61K 47/34* (2013.01); *A61K 47/40* (2013.01); *A61K 47/42* (2013.01); *A61K 47/58* (2017.08); *A61K 47/6901* (2017.08); *A61M 31/002* (2013.01); *C08G 18/4277* (2013.01); *C08G 18/73* (2013.01); *C08G 63/08* (2013.01); *C08G 83/006* (2013.01); *C08L 33/02* (2013.01); *C08L 33/08* (2013.01); *C08L 33/14* (2013.01); *C08G 2230/00* (2013.01); *C08L 2203/02* (2013.01); *Y02A 50/411* (2018.01)

(58) Field of Classification Search
None
See application file for complete search history.

(56) References Cited

U.S. PATENT DOCUMENTS

| | | |
|---|---|---|
| 3,844,285 A | 10/1974 | Laby |
| 3,976,764 A | 8/1976 | Watanabe et al. |

(Continued)

FOREIGN PATENT DOCUMENTS

| | | |
|---|---|---|
| AU | 61990/90 A | 3/1991 |
| EP | 0202159 A2 | 11/1986 |

(Continued)

OTHER PUBLICATIONS

Extended European Search Report dated Dec. 20, 2017 for Application No. EP 15806017.8.
International Search Report and Written Opinion for PCT/US2015/035423 dated Sep. 15, 2015.
International Preliminary Report on Patentability for PCT/US2015/035423 dated Dec. 22, 2016.
International Search Report and Written Opinion dated Jul. 21, 2016 for Application No. PCT/US2016/030020.
International Preliminary Report on Patentability dated Nov. 16, 2017 for Application No. PCT/US2016/030020.
(Continued)

*Primary Examiner* — Abigail Vanhorn
(74) *Attorney, Agent, or Firm* — Wolf, Greenfield & Sacks, P.C.

(57) ABSTRACT

Described are methods of making a gastric residence structure including an active substance. The methods may include forming one or more arms comprising a loadable polymeric component, wherein the loadable polymeric component includes one or more polymeric materials and at least one active substance. The methods may also include connecting the one or more arms to an elastic polymeric component using a separate linker component. The gastric residence structures may be configured to be folded and physically constrained during administration and may be configured to assume an open retention shape upon removal of a constraint. The change between the folded shape and the open retention shape may be mediated by the elastic polymeric component that undergoes elastic deformation when the residence structure is in the folded shape and recoils when the gastric residence structure assumes the open retention shape.

69 Claims, 52 Drawing Sheets

Related U.S. Application Data

No. 15/317,566, filed as application No. PCT/US2015/035423 on Jun. 11, 2015, now Pat. No. 10,182,985.

(60) Provisional application No. 62/010,992, filed on Jun. 11, 2014.

(51) Int. Cl.

| | |
|---|---|
| *A61K 47/32* | (2006.01) |
| *C08L 33/02* | (2006.01) |
| *C08L 33/08* | (2006.01) |
| *C08L 33/14* | (2006.01) |
| *A61K 47/10* | (2017.01) |
| *A61K 47/34* | (2017.01) |
| *A61K 47/40* | (2006.01) |
| *A61K 47/42* | (2017.01) |
| *A61M 31/00* | (2006.01) |

(56) References Cited

U.S. PATENT DOCUMENTS

| | | |
|---|---|---|
| 4,451,260 A | 5/1984 | Mitra |
| 4,676,507 A | 6/1987 | Patterson |
| 4,735,804 A | 4/1988 | Caldwell et al. |
| 4,758,436 A | 7/1988 | Caldwell et al. |
| 4,767,627 A | 8/1988 | Caldwell et al. |
| 4,996,058 A | 2/1991 | Sinnreich |
| 5,002,772 A | 3/1991 | Curatolo et al. |
| 5,007,790 A | 4/1991 | Shell |
| 5,047,464 A | 9/1991 | Pogany et al. |
| 5,443,843 A | 8/1995 | Curatolo et al. |
| 5,840,332 A | 11/1998 | Lerner et al. |
| 6,120,803 A | 9/2000 | Wong et al. |
| 6,306,439 B1 | 10/2001 | Penners et al. |
| 6,375,649 B1 | 4/2002 | Jellie |
| 6,436,069 B1 | 8/2002 | Jellie |
| 6,488,962 B1 | 12/2002 | Berner et al. |
| 6,500,168 B1 | 12/2002 | Jellie |
| 6,548,083 B1 | 4/2003 | Wong et al. |
| 6,685,962 B2 | 2/2004 | Friedman et al. |
| 6,776,999 B1 | 8/2004 | Krumme |
| 6,780,168 B2 | 8/2004 | Jellie |
| 6,962,579 B2 | 11/2005 | Jellie |
| 7,691,151 B2 | 4/2010 | Kutsko et al. |
| 8,021,384 B2 | 9/2011 | Weiss et al. |
| 8,038,659 B2 | 10/2011 | Boyden et al. |
| 8,158,143 B2 | 4/2012 | Lendlein et al. |
| 8,277,843 B2 | 10/2012 | Singh et al. |
| 8,298,574 B2 | 10/2012 | Tsabari et al. |
| 8,377,453 B2 | 2/2013 | Han et al. |
| 8,414,559 B2 | 4/2013 | Gross |
| 8,586,083 B2 | 11/2013 | Mohammad |
| 8,609,136 B2 | 12/2013 | Tsabari et al. |
| 8,753,678 B2 | 6/2014 | Tsabari et al. |
| 8,771,730 B2 | 7/2014 | Navon et al. |
| 9,072,663 B2 | 7/2015 | Navon et al. |
| 9,107,816 B2 | 8/2015 | Lee et al. |
| 9,220,688 B2 | 12/2015 | Alon et al. |
| 9,259,387 B2 | 2/2016 | Navon et al. |
| 10,182,985 B2 | 1/2019 | Bellinger et al. |
| 10,413,507 B2 | 9/2019 | Zhang et al. |
| 2002/0022048 A1 | 2/2002 | Bromberg et al. |
| 2002/0132008 A1 | 9/2002 | Mumper et al. |
| 2004/0180086 A1 | 9/2004 | Ramtoola et al. |
| 2004/0219186 A1 | 11/2004 | Ayres |
| 2005/0175702 A1 | 8/2005 | Muller-Schulte |
| 2006/0142794 A1 | 6/2006 | Lendlein et al. |
| 2007/0104754 A1 | 5/2007 | Sterling et al. |
| 2007/0123809 A1 | 5/2007 | Weiss et al. |
| 2007/0129784 A1 | 6/2007 | Lendlein |
| 2007/0264307 A1 | 11/2007 | Chen et al. |
| 2008/0075766 A1 | 3/2008 | Li et al. |
| 2008/0153779 A1 | 6/2008 | Liao et al. |
| 2008/0260824 A1 | 10/2008 | Nangia et al. |
| 2009/0092415 A1 | 4/2009 | Murakami et al. |
| 2009/0182424 A1 | 7/2009 | Marco et al. |
| 2009/0246142 A1 | 10/2009 | Bhatia et al. |
| 2009/0324694 A1 | 12/2009 | Mohammad |
| 2010/0152410 A1 | 6/2010 | East et al. |
| 2010/0168439 A1 | 7/2010 | Olson |
| 2010/0266655 A1 | 10/2010 | Dadey |
| 2011/0040318 A1 | 2/2011 | Marco et al. |
| 2011/0052700 A1 | 3/2011 | Han et al. |
| 2011/0268666 A1 | 11/2011 | Friedman et al. |
| 2012/0116285 A1 | 5/2012 | Duggirala |
| 2012/0165793 A1 | 6/2012 | Ortiz et al. |
| 2012/0165794 A1 | 6/2012 | Ortiz et al. |
| 2012/0301547 A1 | 11/2012 | Gan et al. |
| 2012/0321706 A1 | 12/2012 | Masri et al. |
| 2013/0226104 A1 | 8/2013 | Hyde et al. |
| 2013/0273135 A1 | 10/2013 | Brooks et al. |
| 2014/0050784 A1 | 2/2014 | Kagan et al. |
| 2014/0052171 A1 | 2/2014 | Tegels |
| 2014/0249499 A1 | 9/2014 | Selaru et al. |
| 2015/0335592 A1 | 11/2015 | Barnscheid et al. |
| 2016/0317796 A1 | 11/2016 | Zhang et al. |
| 2017/0051099 A1 | 2/2017 | DiCiccio et al. |
| 2017/0106099 A1 | 4/2017 | Bellinger et al. |
| 2017/0128576 A1 | 5/2017 | Zhang et al. |
| 2017/0135954 A1 | 5/2017 | Bellinger et al. |
| 2017/0266112 A1 | 9/2017 | Bellinger et al. |
| 2018/0311154 A1 | 11/2018 | Kanasty et al. |
| 2019/0070107 A1 | 3/2019 | Bellinger et al. |
| 2019/0070108 A1 | 3/2019 | Bellinger et al. |
| 2019/0125667 A1 | 5/2019 | Bellinger et al. |
| 2019/0133936 A1 | 5/2019 | Bellinger et al. |
| 2019/0175500 A1 | 6/2019 | Bellinger et al. |
| 2019/0231697 A1 | 8/2019 | Bellinger et al. |
| 2019/0254966 A1 | 8/2019 | Bellinger et al. |
| 2019/0262265 A1 | 8/2019 | Bellinger et al. |

FOREIGN PATENT DOCUMENTS

| | | |
|---|---|---|
| EP | 0344939 A2 | 12/1989 |
| EP | 0388234 A1 | 9/1990 |
| EP | 0415671 A2 | 3/1991 |
| EP | 0202159 B1 | 7/1991 |
| EP | 0344939 B1 | 1/1993 |
| EP | 0820258 B1 | 10/2002 |
| EP | 1124534 B1 | 1/2004 |
| EP | 2329810 A1 | 6/2011 |
| EP | 1528916 B1 | 12/2012 |
| JP | 3-128934 A | 5/1991 |
| JP | 3-163011 A | 7/1991 |
| JP | 2006-518392 A | 8/2006 |
| WO | WO 00/25742 A1 | 5/2000 |
| WO | WO 01/37812 A2 | 5/2001 |
| WO | WO 03/015745 A1 | 2/2003 |
| WO | WO 2004/010978 A1 | 2/2004 |
| WO | WO 2004/073690 A1 | 9/2004 |
| WO | WO 2004/112755 A1 | 12/2004 |
| WO | WO 2006/072948 A1 | 7/2006 |
| WO | WO 2006/084164 A2 | 8/2006 |
| WO | WO 2007/027812 A2 | 3/2007 |
| WO | WO 2007/048223 A2 | 5/2007 |
| WO | WO 2007/083309 A2 | 7/2007 |
| WO | WO 2007/083309 A3 | 7/2007 |
| WO | WO 2007/093999 A1 | 8/2007 |
| WO | WO 2008/015162 A1 | 2/2008 |
| WO | WO 2008/140651 A2 | 11/2008 |
| WO | WO 2009/144558 A1 | 12/2009 |
| WO | WO 2010/035273 A2 | 4/2010 |
| WO | WO 2010/035273 A3 | 4/2010 |
| WO | WO 2010/064100 A1 | 6/2010 |
| WO | WO 2010/064139 A2 | 6/2010 |
| WO | WO 2010/064139 A3 | 6/2010 |
| WO | WO 2011/032087 A2 | 3/2011 |
| WO | WO 2012/087658 A1 | 6/2012 |
| WO | WO 2014/014348 A1 | 1/2014 |
| WO | WO 2015/083171 A1 | 6/2015 |
| WO | WO 2015/191920 A1 | 12/2015 |
| WO | WO 2017/070612 A1 | 4/2017 |

(56) References Cited

FOREIGN PATENT DOCUMENTS

| WO | WO 2017/100367 A1 | 6/2017 |
|---|---|---|
| WO | WO 2017/205844 A2 | 11/2017 |
| WO | WO 2018/064630 A1 | 4/2018 |

OTHER PUBLICATIONS

International Search Report and Written Opinion dated Dec. 29, 2016 for Application No. PCT/US2016/058309.
International Preliminary Report on Patentability dated May 3, 2018 for Application No. PCT/US2016/058309.
International Search Report and Written Opinion dated Feb. 28, 2017 for Application No. PCT/US2016/065453.
International Search Report and Written Opinion dated Nov. 13, 2017 for Application No. PCT/US2017/034856.
International Search Report and Written Opinion dated Dec. 14, 2017 for Application No. PCT/US2017/054608.
Agrawal et al., Clinical relevance of the nutcracker esophagus: suggested revision of criteria for diagnosis. J Clin Gastroenterol. Jul. 2006;40(6):504-9.
Ajili et al., Polyurethane/polycaprolactane blend with shape memory effect as a proposed material for cardiovascular implants. Acta Biomaterialia. 2009;5(5): 1519-30. doi:10.1016/j.actbio.2008.12.014.
Belknap et al., Feasibility of an ingestible sensor-based system for monitoring adherence to tuberculosis therapy. Plos One. Jan. 2013;8(1):e53373(1-5).
Bellinger et al., Oral, ultra-long-lasting drug delivery: Application toward malaria elimination goals. Sci Transl Med. Nov. 16, 2016;8(365):365ra157(1-12). 13 pages.
Bellinger et al., Oral, ultra-long-lasting drug delivery: Application toward malaria elimination goals. Sci Transl Med. Nov. 16, 2016;8(365):365ra157(1-12). Supplementary Materials. 8 pages.
Byrne et al., The ingestible telemetric body core temperature sensor: a review of validity and exercise applications. Brit J Sport Med. 2007;41:126-33, doi:10.1136/bjsm.2006.026344.
Cargill et al., Controlled gastric emptying. 1. Effects of physical properties on gastric residence times of nondisintegrating geometric shapes in beagle dogs. Pharm Res. Aug. 1988;5(8):533-6.
Cargill et al., Controlled gastric emptying. II. In vitro erosion and gastric residence times of an erodible device in beagle dogs. Pharm Res. Jun. 1989;6(6):506-9.
Choudhry et al. Full coverage for preventive medications after myocardial infarction. N Engl J Med. Dec. 1, 2011;365:2088-2097. doi: 10.1056/NEJMsa1107913. Epub Nov. 14, 2011.
Cirillo et al., Carbon nanotubes hybrid hydrogels in drug delivery: A perspective review. BioMed Res Intl. Jan. 21, 2014;2014:825017. 17 pages.
Davies et al., Release characteristics, ovarian activity and menstrual bleeding pattern with a single contraceptive implant releasing 3-ketodesogestrel. Contraception. Mar. 1993;47(3):251-61.
Edwards, Physiological concepts of the pylorus. Proc R Soc Med. Nov. 1961;54:930-3.
Ereqat et al., MDR tuberculosis and non-compliance with therapy. Lancet Infect Dis. Sep. 2011;11(9):662. doi: 10.1016/S1473-3099(11)70227-4.
Fallon et al., The surgical management of Rapunzel syndrome: a case series and literature review. J Pediatr Surg. Apr. 2013;48(4):830-4. doi: 10.1016/j.jpedsurg.2012.07.046.
Farra et al., First-in-human testing of a wirelessly controlled drug delivery microchip. Sci Transl Med. Feb. 22, 2012;4(122):122ra21. doi: 10.1126/scitranslmed.3003276. Epub Feb. 16, 2012.
Fix et al., Controlled gastric emptying. III. Gastric residence time of a nondisintegrating geometric shape in human volunteers. Pharm. Res. 1993;10(7):1087-9.
Fuhrmann et al. Sustained gastrointestinal activity of dendronized polymer-enzyme conjugates. Nat Chem. Jul. 2013; 5:582-9, doi: 10.1038/Nchem.1675.
Genco et al., Bioenterics intragastric balloon: The Italian experience with 2,515 patients. Obes Surg. 2005; 15:1161-4, doi: 10.1381/0960892055002202.
Gordi et al., Pharmacokinetics of gabapentin after a single day and at steady state following the administration of gastric-retentive-extended-release and immediate-release tablets: a randomized, open-label, multiple-dose, three-way crossover, exploratory study in healthy subjects. Clin Ther. May 2008;30(5):909-16. doi: 10.1016/j.clinthera.2008.05.008.
Huang et al., Shape memory materials. Materials Today. Jul.-Aug. 2010;13(7-8):54-61. doi: 10.1016/S1369-7021(10)70128-0.
Hwang et al., Gastric retentive drug-delivery systems. Crit Rev Ther Drug Carrier Syst. 1998;15(3):243-84.
Karim et al., Effectiveness and safety of tenofovir gel, an antiretroviral microbicide, for the prevention of HIV infection in women. Science. Sep. 3, 2010;329(5996):1168-74. doi: 10.1126/science.1193748. Epub Jul. 19, 2010. Erratum in: Science. Jul. 29, 2011;333(6042):524.
Kethu et al., Endoluminal bariatric techniques. Gastrointestinal endoscopy. 2012;76(1):1-7, doi:10.1016/j.gie.2012.02.020.
Kim et al., Biologically derived melanin electrodes in aqueous sodium-ion energy storage devices. P Natl Acad Sci USA. Dec. 24, 2013;110(252): 20912-17, doi: 10.1073/pnas.1314345110.
Kim et al., Polyurethanes having shape memory effects. Polymer. 1996;37(26):5781-93. doi:10.1016/S0032-3861(96)00442-9.
Lam et al., Advanced progress of microencapsulation technologies: In vivo and in vitro models for studying oral and transdermal drug deliveries. J. Control Release. 2014; 178,:25-45.
Laulicht et al., Localization of magnetic pills. Proc Natl Acad Sci. Feb. 8, 2011;108:2252-7, doi:10.1073/pnas.1016367108.
Li et al., Polyanhydride implant for antibiotic delivery—from the bench to the clinic. Adv Drug Deliv Rev. Oct. 16, 2002;54(7):963-86.
Liu et al., Review of electro-active shape-memory polymer composite. Compos Sci and Technol. 2009;69(13): 2064-8. doi:10.1016/j.compscitech.2008.08.016.
Marrazzo et al., Tenofovir-based preexposure prophylaxis for HIV infection among African women. N Engl J Med. Feb. 5, 2015;372(6):509-18. doi: 10.1056/NEJMoa1402269.
Meng et al., A review of shape memory polymer composites and blends. Composites Part A: Applied Science and Manufacturing. 2009;40(11):1661-72. doi:10.1016/j.compositesa.2009.08.011.
Mintchev et al., Pilot study of temporary controllable gastric pseudobezoars for dynamic non-invasive gastric vol. reduction. Physiol Meas. Feb. 2010;31(2):131-44. doi: 10.1088/0967-3334/31/2/001. Epub Dec. 11, 2009.
Moes, Gastroretentive dosage forms. Crit Rev Ther Drug Carrier Syst. 1993;10: 143-195. Submitted in 3 parts.
Mohr et al., Initiation of shape-memory effect by inductive heating of magnetic nanoparticles in thermoplastic polymers. Proc Natl Acad Sci U S A. Mar. 7, 2006;103(10):3540-5. Epub Feb. 28, 2006.
Olson et al., Chemical mimicry of viral capsid self-assembly. Proc Natl Acad Sci U S A. Dec. 26, 2007;104(52):20731-6. Epub Dec. 18, 2007.
Osterberg et al., Adherence to medication. N Engl J Med. Aug. 4, 2005;353(5):487-497.
Phadke et al., Rapid self-healing hydrogels. Proc Natl Acad Sci U S A. Mar. 20, 2012;109(12):4383-8. doi: 10.1073/pnas.1201122109. Epub Mar. 5, 2012.
Phillips et al., Gastric trichobezoar: case report and literature review. Mayo Clin Proc. Jul. 1998;73(7):653-6. Review.
Richter et al., Esophageal manometry in 95 healthy adult volunteers. Variability of pressures with age and frequency of "abnormal" contractions. Dig Dis Sci. Jun. 1987;32(6):583-92.
Salessiotis, Measurement of the diameter of the pylorus in man: Part I. Experimental project for clinical application. The Amer J of Surgery. Sep. 1972; 124:331-3, doi:http://dx.doi.org/10.1016/0002-9610(72)90036-0.
Salunke et al., Self-assembly of purified polyomavirus capsid protein VP1. Cell. Sep. 12, 1986;46(6):895-904.
Singer et al., The fluid mosaic model of the structure of cell membranes. Science. Feb. 18, 1972;175(4023):720-31.

(56) References Cited

OTHER PUBLICATIONS

Singh et al., Floating drug delivery systems: an approach to oral controlled drug delivery via gastric retention. J Control Release. Feb. 3, 2000;63(3):235-59.
Tao et al. Silk-based conformal, adhesive, edible food sensors. Adv Mater. 2012; 24:1067-72, doi:10.1002/adma.201103814.
Timmer et al., Pharmacokinetics of etonogestrel and ethinylestradiol released from a combined contraceptive vaginal ring. Clin Pharmacokinet. Sep. 2000;39(3):233-42.
Traverso et al., Special delivery for the gut. Nature. Mar. 26, 2015;519:S19.
Whitesides et al., Self-assembly at all scales. Science. Mar. 29, 2002;295(5564):2418-21.
Wilber et al., Monodisperse self-assembly in a model with protein-like interactions. J Chem Phys. Nov. 7, 2009;131(17):175102. doi: 10.1063/1.3243581.
Wilber et al., Self-assembly of monodisperse clusters: Dependence on target geometry. J Chem Phys. Nov. 7, 2009;131(17):175101. doi: 10.1063/1.3243580.
Won et al. Oligopeptide complex for targeted non-viral gene delivery to adipocytes. Nat Mater. Dec. 2014;13:1157-64, doi: 10.1038/Nmat4092.
Zhang et al., A pH-responsive supramolecular polymer gel as an enteric elastomer for use in gastric devices. Nat Mater. Oct. 2015;14(10):1065-71. 9 pages. Epub Jul. 27, 2015. doi: 10.1038/NMAT 4355.
Zhang et al., A pH-responsive supramolecular polymer gel as an enteric elastomer for use in gastric devices. Nat Mater. Oct. 2015;14(10):1065-71. 9 pages. Epub Jul. 27, 2015. doi: 10.1038/NMAT 4355. Suppl Info 6 pages.
Zhang et al., Biodegradable shape memory nanocomposites with thermal and magnetic field responsiveness. J Biomater Sci Polym Ed. 2013;24(9):1057-70. doi: 10.1080/09205063.2012.735098. Epub Oct. 15, 2012.
U.S. Appl. No. 15/307,806, filed Oct. 28, 2016, DiCiccio et al.
U.S. Appl. No. 16/177,670, filed Nov. 1, 2018, Bellinger et al.
U.S. Appl. No. 16/177,687, filed Nov. 1, 2018, Bellinger et al.
U.S. Appl. No. 16/177,704, filed Nov. 1, 2018, Bellinger et al.
U.S. Appl. No. 16/277,516, filed Feb. 15, 2019, Bellinger et al.
U.S. Appl. No. 15/143,230, filed Apr. 29, 2016, Zhang et al.
U.S. Appl. No. 15/317,601, filed Dec. 9, 2016, Zhang et al.
U.S. Appl. No. 15/317,628, filed Dec. 9, 2016, Bellinger et al.
U.S. Appl. No. 16/014,549, filed Jun. 21, 2018, Bellinger et al.
U.S. Appl. No. 15/769,949, filed Apr. 20, 2018, Kanasty et al.
U.S. Appl. No. 15/782,021, filed Jun. 6, 2018, Bellinger et al.
EP 15806017.8, Dec. 20, 2017, Extended European Search Report.
PCT/US2015/035423, Sep. 15, 2015, International Search Report and Written Opinion.
PCT/US2015/035423, Dec. 22, 2016, International Preliminary Report on Patentability.
PCT/US2016/030020, Jul. 21, 2016, International Search Report and Written Opinion.
PCT/US2016/030020, Nov. 16, 2017, International Preliminary Report on Patentability.
PCT/US2016/058309, Dec. 29, 2016, International Search Report and Written Opinion.
PCT/US2016/058309, May 3, 2018, International Preliminary Report on Patentability.
PCT/US2016/065453, Feb. 28, 2017, International Search Report and Written Opinion.
PCT/US2017/034856, Nov. 13, 2017, International Search Report and Written Opinion.
PCT/US2017/054608, Dec. 14, 2017, International Search Report and Written Opinion.
U.S. Appl. No. 16/528,197, filed Jul. 31, 2019, Zhang et al.
[No Author Listed], Wound Closure Manual. Ethicon, Inc. A Johnson and Johnson company. 2005: 127 pages.
Uhrich et al., Polymeric Systems for Controlled Drug Release. Chem Rev. 1999;99:3181-98.

100

| 110 | 130 | 120 |

| 120 | 130 | 110 | 130 | 120 |

FIG. 1C

RESIDENCE STRUCTURES AND RELATED METHODS

RELATED APPLICATIONS

This Application is a Continuation of U.S. application Ser. No. 16/177,704, filed Nov. 1, 2018, entitled "RESIDENCE STRUCTURES AND RELATED METHODS", which is a Continuation of U.S. application Ser. No. 15/317,566, filed Dec. 9, 2016, which is a national stage filing under 35 U.S.C. 371 of International Patent Application Serial No. PCT/US2015/035423, filed Jun. 11, 2015, which claims priority under 35 USC 119(e) to U.S. Provisional Application Ser. No. 62/010,992, filed Jun. 11, 2014, the contents of each is incorporated herein by reference in its entirety for all purposes.

STATEMENT OF GOVERNMENT SUPPORT

This invention was made with Government support under Grant No. R37 EB000244 awarded by the National Institutes of Health. The Government has certain rights in this invention.

FIELD OF THE INVENTION

Embodiments described herein generally relate to residence structures, systems, and related methods.

BACKGROUND OF THE INVENTION

Adherence rates of patients to a self-administration protocol for therapeutics and diagnostics over an extended or indefinite duration is often poor, with adherence rates for oral therapies for chronic asymptomatic conditions estimated to be less than 50%. The challenge of low adherence rates is greatest in primary and secondary prevention applications where a disease to be prevented or treated is often asymptomatic and the therapy has no immediate tangible benefit. Many factors contribute to low adherence rates including treatment cost, access, side effects, and the inconvenience of dosing regimens.

Current state-of-the-art approaches to improving adherence rates include educational interventions, telephone-based counseling, health information technology solutions, interactive pharmacy tools, and changing models of payment for care, such as no-copayment plans after myocardial infarction. All of these approaches have achieved only modest improvements. Meanwhile, pharmacologic solutions to the adherence rate problem are generally involve invasive delivery structures and a subset of pharmacologic agents formulated for extended release. Recent advances in extended release pharmacologic systems are predominantly limited to subcutaneous, transdermal, intravaginal, and surgical implants. Conventional solutions include invasive modalities such as surgical implants (including, e.g., wireless, programmable structures available from MicroCHIPS, Inc. (Lexington, Mass.)) or modalities limited to specialized applications such as birth control (including, e.g., NuvaRing® and Implanon®, both available from Merck & Co., Inc. (Whitehouse Station, N.J.)). Structures like those available from MicoCHIPS are also limited to delivering therapeutic agents with high potency because they can be administered in only microgram or smaller quantities.

Oral administration has the potential for the widest patient acceptance; however, no oral delivery system has been demonstrated to enable extended release via the oral route due to a number of fundamental barriers. Principally, the transit time for a bolus of food through, for example, the human gastrointestinal tract is rapid, typically lasting about 24 to 48 hours and including about 1 to 2 hours in the stomach, about 3 hours in the small intestine, and about 6 to 12 hours in the large intestine. One strategy for extended duration therapeutic delivery, therefore, would be to prolong the transit time of an orally-administered therapeutic (but not food). Gastric residence and/or slowed transit could be attempted and/or tolerated at a number of segments of a gastrointestinal tract, as evidenced by bezoars and bariatric structures. Bezoars (i.e., masses found trapped in the gastrointestinal system) can form from a variety of materials that are indigestible (such as food aggregates and hair) and often become clinically apparent in adult humans only at sizes in the hundreds of grams. A bariatric structure, such as an endoscopically-administered intra-gastric balloon, can be used to fill a portion of a patient's stomach to achieve noninvasive gastric reduction for weight loss. Previous attempts at gastric residence for drug delivery include mucoadhesion, gastric swelling, and flotation on gastric fluids. However, none of these approaches have even demonstrated gastric residence for more than 24 hours, let alone progressed to clinical use.

SUMMARY OF THE INVENTION

Residence structures, systems, and related methods are generally provided.

In one aspect, residence structures are provided. In some embodiments, the residence structure comprises a loadable polymeric component, a first linker coupling the loadable polymeric component to a second polymeric component, a second linker comprising at least a portion of or coupled with the loadable polymeric component and/or the elastic polymeric component, wherein at least one of the loadable polymeric component, the second polymeric component, and the first linker, and the second linker comprises an elastic polymeric component, wherein the loadable polymeric component comprises at least about 60 wt % of the total structure weight, wherein the residence structure is characterized by a folding force of at least about 0.2 N, wherein the first linker is degradable under a first set of physiological conditions, and wherein the second linker is degradable under a second set of physiological conditions different than the first set of conditions and is not substantially degradable under the first set of conditions.

In some embodiments, the residence structure comprises a loadable polymeric component, a second polymeric component coupled to the loadable polymeric component via at least one degradable linker comprising at least a portion of or coupled with the loadable polymeric component and/or the second polymeric component, wherein at least one of the loadable polymeric component, the second polymeric component, and the degradable linker comprises an elastic polymeric component, wherein the loadable polymeric component comprises at least about 60 wt % of the total structure weight, wherein the residence structure has a folding force of at least about 0.2 N, and wherein the residence structure has an uncompressed cross-sectional dimension of at least about 2 cm.

In some embodiments, the residence structure comprises a loadable polymeric component and a second polymeric component coupled with the loadable polymeric component, at least one degradable linker comprising at least a portion of or coupled with the loadable polymeric component and/or the second polymeric component, wherein the residence structure is configured such that it is retained at a location internally of a subject for at least about 24 hours.

In some embodiments, the residence structure comprises a loadable polymeric component and a second polymeric component coupled with the loadable polymeric component, at least one degradable linker comprising at least a portion of or coupled with the loadable polymeric component and/or the second polymeric component, wherein the loadable polymeric component comprises an active substance, the residence structure is configured such that the active substance is released from the loadable polymeric material at a particular initial average rate as determined over the first 24 hours of release, and wherein the active substance is released at an average rate of at least about 1% of the initial average rate over a 24 hour period after the first 24 hours of release.

In another aspect, systems are provided. In some embodiments, the system comprises a containing structure, a residence structure contained within the containing structure, wherein the residence structure is constructed and arranged to have a first configuration after release from the containing structure, wherein the residence structure is constructed and arranged to have a second configuration when contained within the containing structure, wherein the first configuration has an uncompressed cross-sectional dimension of at least about 2 cm, and wherein the second configuration has a convex hull at least about 10% less than a convex hull of the first configuration and/or wherein the second configuration has a largest cross-sectional dimension at least about 10% less than a largest cross-sectional dimension of the first configuration, and wherein a first portion of the device is degradable under a first set of physiological conditions, while a second portion of the device is not substantially degradable under the first set of physiological conditions.

In another aspect, methods for delivering a residence structure are provided. In some embodiments, the method comprises administering, to a subject, a containing structure comprising a residence structure, such that the containing structure releases the residence structure at a location within the subject, wherein the residence structure has a second configuration within the containing structure, wherein, after the residence structure is released from the containing structure, the residence structure obtains a first configuration such that the residence structure is retained at or in proximity to the location within the subject for at least about 24 hours.

In some embodiments, the method comprises administering, to a subject, a containing structure comprising a residence structure, such that the containing structure releases the residence structure at a location within the subject, wherein the residence structure has a second configuration within the containing structure, the residence device comprises a loadable polymeric component that comprises an active substance, the residence structure is configured such that the active substance is released from the residence structure at an initial average rate over the first 24 hours of release, and the active substance is released at an average rate of at least about 1% of the initial average rate over a 24 hour period after the first 24 hours of release.

In another aspect, a containing structure is constructed and arranged to be administered, to a subject, the containing structure comprising a residence structure, such that the containing structure releases the residence structure at a location within the subject, wherein the residence structure has a second configuration within the containing structure, wherein, after the residence structure is released from the containing structure, the residence structure obtains a first configuration such that the residence structure is retained at or in proximity to the location within the subject for at least about 24 hours.

In some embodiments, a containing structure is constructed and arranged to be administered, to a subject, the containing structure comprising a residence structure, such that the containing structure releases the residence structure at a location within the subject, wherein the residence structure has a second configuration within the containing structure, the residence device comprises a loadable polymeric component that comprises an active substance, the residence structure is configured such that the active substance is released from the residence structure at an initial average rate over the first 24 hours of release, and the active substance is released at an average rate of at least about 1% of the initial average rate over a 24 hour period after the first 24 hours of release.

In some embodiments, the system comprises at least one residence structure configured to administer the at least one of a therapeutic agent, a diagnostic agent, and an enhancement agent during a residence time period longer than at least twenty-four hours, the at least one residence structure having a first shape configured to maintain an in vivo position relative to an internal orifice during the residence time period, the at least one residence structure comprising at least one enteric elastomer linker positioned such that a level of dissociation of the at least one enteric elastomer linker ends the residence time period and allows the at least one residence structure to pass through the internal orifice.

In some embodiments, the system comprises at least one residence structure configured to at least one of transport and maintain the at least one structure during a residence time period longer than at least twenty-four hours, the at least one residence structure having a first shape configured to maintain an in vivo position relative to an internal orifice during the residence time period, the at least one residence structure comprising at least one enteric elastomer linker positioned such that a level of disassociation of the at least one enteric elastomer linker ends the residence time period and allows the at least one residence structure to pass through the internal orifice.

In some embodiments, the at least one enteric elastomer linker is configured to disassociate at least in part over the retention time period.

In some embodiments, the at least one retention structure is loaded with the at least one of a therapeutic agent, a diagnostic agent, and an enhancement agent before administering the at least one retention structure to the subject.

In some embodiments, after administering the at least one retention structure to the subject, the at least one retention structure is loaded with the at least one of a therapeutic agent, a diagnostic agent, and an enhancement agent in vivo.

In some embodiments, the retention time period is more than at least one of 24 hours, one week, two weeks, four weeks, and one year.

In some embodiments, the system further comprises at least one containing structure, each configured to maintain a retention structure in a second shape configured for packing into a containing structure.

In some embodiments, the at least one containing structure is configured to be at least one of ingested, self-administered, and orally administered.

In some embodiments, the at least one containing structure comprises at least one of a 000 capsule, 00 capsule, 0 capsule, 1 capsule, 2 capsule, 3 capsule, 4 capsule, and 5 capsule.

In some embodiments, the second shape is configured such that the retention structure occupies a volume more than 60% of a cavity defined by the containing structure.

In some embodiments, the retention structure is configured to adopt the first shape upon release from the containing structure.

In some embodiments, prior to release from the containing structure the retention structure is stored in the second shape in the containing structure for more than at least one of 72 hours, one week, two weeks, four weeks, one year, and five years.

In some embodiments, the at least one retention structure further comprises a deformable material, the first shape comprises an elliptical outline in a first plane with a major axis and a minor axis, the second shape comprises a helix such that an axis of the helix is along the minor axis, and at least one enteric elastomer linker is disposed along the minor axis.

In some embodiments, at least one enteric elastomer linker is disposed along the major axis.

In some embodiments, the at least one retention structure further comprises a core and a plurality of radial projections at least one of attached to and incorporated with the core, the first shape comprises the plurality of projections projecting from the core in a plurality of directions, and the second shape comprises the plurality of projections projecting from the core in a substantially parallel direction to each other.

In some embodiments, the at least one enteric elastomer linker comprises a first enteric elastomer linker disposed along a first radial projection in the plurality of radial projections.

In some embodiments, the at least one enteric elastomer linker comprises a first enteric elastomer linker connecting a first radial projection in the plurality of radial projections to the core.

In some embodiments, the core comprises the at least one enteric elastomer linker.

In some embodiments, a first radial projection in the plurality of radial projections has a length corresponding to a maximum dimension of the containing structure.

In some embodiments, the plurality of radial projections are arranged such that the plurality of radial projections define N internal sector angles of approximately 360°/N, where N is the total number of radial projections.

In some embodiments, the at least one retention structure further comprises a deformable material, the first shape comprises a polygon outline in a first plane, the second shape comprises each side of the polygon outline folded, and at least one enteric elastomer linker is positioned at each vertex of the polygon outline.

In some embodiments, a first side of the polygon outline has a length corresponding to the length of the containing structure.

In some embodiments, each of the sides defines an internal sector angle of approximately 360°/N, where N is the total number of sides.

In some embodiments, the at least one retention structure further comprises a deformable material, the first shape comprises a circular ring, the second shape comprises the circular ring folded into quadrants, and at least one enteric elastomer linker is positioned at each vertex of each arc of the quadrants.

In some embodiments, the at least one retention structure further comprises a core and a plurality of small rounded loops at least one of attached to and incorporated with the core, the small rounded loops comprising a shape memory alloy, the core comprising at least one enteric elastomer linker, the first shape comprises the plurality of small rounded loops extending from the core, and the second shape comprises the plurality of small rounded loops folded against the core.

In some embodiments, the first shape is configured to prolong a transit time through at least part of the subject's gastrointestinal tract by at least the retention time period.

In some embodiments, the first shape is configured to maintain the at least one retention structure in a gastric cavity of the subject during at least the retention period.

In some embodiments, the internal orifice is a pyloric orifice.

In some embodiments, the at least one retention structure is loaded with a mass of the at least one of a therapeutic agent, a diagnostic agent, and an enhancement agent formulated for release.

In some embodiments, exposure to at least one of an alkali solution, the at least one enteric elastomer linker accelerates disassociation of at least one enteric elastomer linker.

In some embodiments, exposure to at least one of an alkali solution, the at least one enteric elastomer linker accelerates dissociation of the at least one enteric elastomer linker to the level of dissociation ending the retention time period and allowing the at least one retention structure to pass through the internal orifice.

In some embodiments, the at least one retention structure further comprises at least one material configured for drug loading via at least one of solvent loading, melt loading, physical blending, supercritical carbon dioxide, and conjugation reactions.

In some embodiments, the at least one material configured for drug loading is further configured to administer at least one loaded drug via at least one of diffusion and slow matrix degradation, dissolution, degradation, swelling, diffusion of the at least one loaded drug, an ionic gradient, hydrolysis, and cleavage of the conjugating bonds.

In some embodiments, the at least one enteric elastomer linker is different from the delivery material and configured to at least partially resist drug loading.

In some embodiments, the at least one enteric elastomeric linker comprises an enteric polymer comprising a polymer of an acryloylaminoalkylene acid monomer, or salts thereof.

In some embodiments, the acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminononanoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononanoic acid, methacryloyl-10-aminodecanoic acid, methacryloyl-11-aminoundecanoic acid, methacryloyl-12-aminododecanoic acid, salts thereof, and combinations thereof.

In some embodiments, the at least one enteric elastomeric linker comprises an enteric polymer blend of at least two enteric polymers, comprising a first enteric polymer of claim 37 and a second enteric polymer comprising poly(methacrylic acid-co-alkyl acrylate), or salts thereof.

In some embodiments, the first enteric polymer is a homopolymer of acryloyl-6-aminocaproic acid or salts thereof.

In some embodiments, the first enteric polymer is a copolymer of acryloyl-6-aminocaproic acid or salts thereof.

In some embodiments, the second enteric polymer is poly(methacrylic acid-co-ethyl acrylate) or salts thereof.

In some embodiments, the poly(methacrylic acid-co-ethyl acrylate) has a molar ratio of methacrylic acid monomer units to ethylacrylate monomer units of about 1:1.

In some embodiments, the first enteric polymer is a homopolymer of acryloyl-6-aminocaproic acid.

In some embodiments, the at least one enteric elastomeric linker comprises an enteric polymer composition comprising a first enteric polymer of claim 37, or salts thereof, and optionally a second enteric poly(methacrylic acid-co-ethyl acrylate), or salts thereof, wherein the weight ratio of the first enteric polymer to the second enteric polymer ranges from about 1:0 to about 1:3.

In some embodiments, the weight ratio of the first enteric polymer to the second enteric polymer ranges from 1:0 to about 1:2.

In some embodiments, the enteric polymer blend is in the form of a polymer gel.

In some embodiments, said polymer gel has a water content of less than about 50% by weight.

In some embodiments, the polymer gel as a water content of less than about 40% by weight.

In some embodiments, the enteric polymer blend exhibits reversible elongation when stretched from 50% to 1500% of its initial length.

In some embodiments, said blend dissolves in an aqueous solution at a pH greater than about 6.0, and is insoluble when immersed in an aqueous solution at a pH less than about 3.0, measured at room temperature over a time period of 4-40 days.

In some embodiments, the enteric polymer blend has a Young's modulus of from 0.1 MPa to 100 MPa.

In some embodiments, the enteric polymer blend exhibits reversible elongation when stretched from 50% to 1500% of its initial length.

One aspect of the present invention contemplates a gastric retention device comprising a central elastic polymeric component coupled to between three and eight loadable polymeric components, each loadable polymeric component projecting radially from the central elastic polymeric component to form a star-like cross-sectional shape, wherein each of the loadable polymeric components is coupled to the central elastic polymeric component. A first degradable linker is present in each loadable polymeric component near or at the interface with the elastic polymeric component. by a first degradable linker. In certain embodiments, the loadable polymeric components further comprise a second degradable linker that may be the same as or different from the first degradable linker. In certain embodiments, the loadable polymeric components comprise polycaprolactone, polylactic acid, polylactic co-glycolic acid and/or mixtures thereof and may further comprise excipients, and the degradable linker is a water soluble and/or degradable polymer and blends thereof, including but not limited to, Polyvinylpyrrolidone, polyvinyl alcohol, Kollidon VA 64, polyorthoester, Polyhydroxybutyrate, Eudragits and mixtures thereof. The device may further comprise at least one of a one of a therapeutic agent, a diagnostic agent, and an enhancement agent, wherein the therapeutic agent is selected from a hydrophilic drug, a hydrophobic drug, artemether, ivermectin, risperidone, doxycycline, an anti-malarial agent, an anti-helminth agent, an antipsychotic agent, and an antibiotic.

The devices of these embodiments can be contained within a soluble container such as one composed of gelatin and which may optionally comprise excipients. In certain embodiments, the device has a minimum uncompressed cross-sectional dimension of about 3-5.5 cm, of about 3 cm, of about 4 cm, of about 5 cm, or of about 5.5 cm. Intermediate minimum uncompressed cross-sectional dimensions are also contemplated. In certain embodiments, the loadable polymeric components have a length approximately equal to the length of a soluble container such that the unencapsulated form has a diameter equal to nearly twice the length of the soluble container. In certain embodiments, the loadable polymeric components have a length of between about 1.3 and about 2.7 cm. It is contemplated that the gastric retention devices of the above embodiments may be retained within the gastric cavity for between 24 hours and about 1 month, or between about 24 hours and 10 days.

Another aspect of the invention is a gastric retention device comprising a central elastic polymeric component comprising a polyurethane, wherein the elastic polymeric component is coupled to six loadable polymeric components, each loadable polymeric component projecting radially from the central elastic polymeric component to form a star-like cross-sectional shape, wherein each of the loadable polymeric components is coupled to the central elastic polymeric component by a time-dependent degradable linker, and wherein the loadable polymeric components further comprise an embedded linker comprising an enteric polymer. In certain embodiments, the loadable polymeric components comprise polycaprolactone and may optionally comprise excipients, and the degradable linker is a water soluble and/or degradable polymer and blends thereof, including but not limited to, Polyvinylpyrrolidone, polyvinyl alcohol, Kollidon VA 64, polyorthoester, Polyhydroxybutyrate, Eudragits and mixtures thereof. In certain embodiments, the device is contained within a soluble container that may optionally comprise excipients. The device may further comprise at least one of a one of a therapeutic agent, a diagnostic agent, and an enhancement agent, wherein the therapeutic agent is selected from a hydrophilic drug, a hydrophobic drug, artemether, ivermectin, risperidone, doxycycline, an anti-malarial agent, an anti-helminth agent, an antipsychotic agent, and an antibiotic.

In certain embodiments, the device has a minimum uncompressed cross-sectional dimension of about 3-5.5 cm, of about 3 cm, of about 4 cm, of about 5 cm, or of about 5.5 cm. Intermediate minimum uncompressed cross-sectional dimensions are also contemplated. In certain embodiments, the loadable polymeric components have a length approximately equal to the length of a soluble container such that the unencapsulated form has a diameter equal to nearly twice the length of the soluble container. In certain embodiments, the loadable polymeric components have a length of between about 1.3 and about 2.7 cm.

It is contemplated that the gastric retention devices of these above embodiments may be retained within the gastric cavity for between 24 hours and about 1 month, or between about 24 hours and 10 days. In certain embodiments the linker comprising an enteric polymer degrades in response to a pH greater than about 5, such that the loadable polymeric components break apart.

In some embodiments, the method comprises administering to a subject at least one residence structure configured to administer the at least one of a therapeutic agent, a diagnostic agent, and an enhancement agent during a residence time period longer than at least twenty-four hours, the at least one residence structure having a first shape configured to maintain an in vivo position relative to an internal orifice during the residence time period, the at least one residence structure comprising at least one enteric elastomer linker positioned such that a level of disassociation of the at least one enteric elastomer linker ends the residence time period and allows the at least one residence structure to pass through the internal orifice.

In some embodiments, the method comprises administering to a subject at least one residence structure configured to at least one of transport and maintain the at least one structure during a residence time period longer than at least twenty-four hours, the at least one residence structure having a first shape configured to maintain an in vivo position relative to an internal orifice during the residence time period, the at least one residence structure comprising at least one enteric elastomer linker positioned such that a level of disassociation of the at least one enteric elastomer linker ends the residence time period and allows the at least one residence structure to pass through the internal orifice.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1C are schematic diagrams of a residence structure, according to one set of embodiments;

DETAILED DESCRIPTION

Figure 1A:
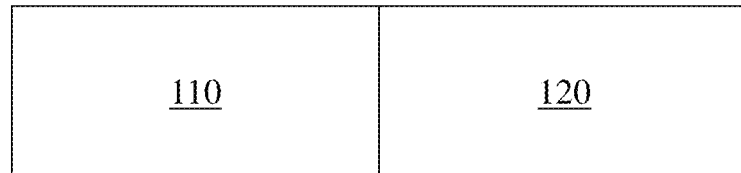

Residence structures, systems, and related methods are generally disclosed. Certain embodiments comprise administering (e.g., orally) a residence structure to a subject (e.g., a patient) such that the residence structure is retained at a location internal to the subject for a particular amount of time (e.g., at least about 24 hours) before being released or partially released. The residence structure may be, in some cases, a gastric residence structure. In some embodiments, the structures and systems described herein comprise one or more materials configured for one or more of (and in any combination) active substance (e.g., a therapeutic agent) loading (in some cases at relatively high levels,) active substance and/or structure stability in acidic environments, mechanical flexibility and strength when contained in an internal cavity (e.g., gastric cavity), easy passage through the GI tract until delivery to a desired internal cavity (e.g., gastric cavity), and/or rapid dissolution/degradation in a physiological environment (e.g., intestinal environment) and/or in response to a chemical stimulant (e.g., ingestion of a solution to induce accelerated dissolution/degradation). In certain embodiments, the structure has a modular design, combining a material configured for controlled release of therapeutic, diagnostic, and/or enhancement agents with a structural material facilitating gastric residence and configured for controlled and/or tunable degradation/dissolution to control the time at which a retention shape integrity is lost to permit the structure to pass out of the gastric cavity. For example, in certain embodiments, the residence structure comprises a first elastic component, a second polymeric component configured to release an active substance (e.g., a therapeutic agent), and, optionally, at least one linker. In some such embodiments, the linker may be configured to degrade such that the residence structure breaks apart and is released from the location internally of the subject after a predetermined amount of time and/or when exposed to a select set of conditions.

In some embodiments, the residence structure has a particular configuration including a particular size and/or shape (e.g., a multi-armed star) in a relaxed state. In certain embodiments, the residence structure may be folded from the relaxed state into a second, compressed configuration. For example, in some cases, the folded/compressed residence structure may be inserted within a capsule or other containment structure in the second configuration such that the residence structure can be delivered orally. The capsule or other containment structure can be, in some cases, configured to dissolve such that the residence structure is released at a particular location internal to the subject (e.g., in the stomach) whereby upon release, it can reversibly revert to the first configuration (e.g. by. recoil). In some embodiments, the structure is configured to adopt a shape and/or size in vivo that slows or prevents further transit in a body (e.g., gastric) cavity (e.g., passage from the body of the stomach through the pylorus.) In some embodiments, the structure adopts a shape and/or size configured for retention (e.g., gastric residence) upon release from a soluble capsule/container and/or soluble retaining structure/element. In some embodiments, the structure is configured for adopting a shape and/or size configured for gastric residence after being stored in its encapsulated shape and/or size for durations greater than 24 hours, including up to about one year. In some embodiments, the mechanical properties of the structure are optimized for safe transient retention of all or a portion of the structure in an internal cavity such as the gastric cavity for durations greater than 24 hours, including up to about one year.

Certain of the structures, systems, and methods described herein can be useful, for example, in achieving gastric residence and/or slowed transit via oral administration for extended in vivo residence and administration of therapeutic, diagnostic, and/or enhancement agents. Certain embodiments of structures and systems described herein may offer certain advantages as compared to traditional compositions and structures and systems configured for internal retention and/or drug release, for example, in their ability to adopt a shape and/or size small enough to be ingested by a subject; adopt a shape and/or size internally that slows or prevents further transit in a body cavity (e.g. the gastric cavity) (e.g., passage from the body of the stomach through the pylorus;) be loaded at high levels (e.g., high mass fraction) with therapeutic, diagnostic, and/or enhancement agents; facilitate controlled release of such therapeutic, diagnostic, and/or enhancement agents with low to no potential for burst release; maintain activity/stability of such therapeutic, diagnostic, and/or enhancement agents in a hostile environment such as the gastric environment for an extended duration; maintain safety with low to no potential for gastric or intestinal obstruction and/or perforation; and/or degrade/dissolve/disassociate into one or more forms configured for passing through a gastrointestinal tract. In certain embodiments, the structures and systems described herein can be configured with durable residence times greater than at least twenty-four hours and lasting up to about one year, or more. In some embodiments, the systems, structures, and methods described herein are compatible with subjects, including, but not limited to, humans and non-human animals. In further embodiments, the systems and structures can be configured to deliver a wide variety of therapeutic, diagnostic, and/or enhancement agents, thus potentially increasing and even maximizing patient treatment therapy adherence rates.

The structures and systems described herein may be modular/multi-component (i.e. formed of multiple interconnected subcomponents.) In some embodiments, the structure comprises one or more polymeric components configured for containing and/or releasing a therapeutic agent, and/or configured for undergoing mechanical deformation such that the component(s) does not permanently deform and/or break, and/or configured to recoil after a particular amount of time such that the structure can be selectively retained at a location internally of a subject. In certain embodiments, the structure comprises two or more polymeric components. For example, in some cases, the structure comprises a first polymeric component and a second polymeric component different than, and in direct contact with, the first polymeric component. As illustrated in FIG. 1A, in some embodiments, structure 100 comprises first polymeric component 110 coupled with second polymeric component 120. In some such embodiments, the first polymeric component may be coupled with the second polymeric component via an adhesive, by chemical interactions (e.g., chemical bonds,) and/or by interpenetrating and/or entangled polymer chains, and/or with other physical, chemical, and/or associative interactions. In some embodiments, the first polymeric component is an elastic polymeric component and the second polymeric component is a loadable polymeric component. Elastic polymeric components and loadable polymeric components are described in more detail, below.

In general, embodiments of the invention may be practiced with any combinations of first, second, third, etc. polymer components, but that for clarity and conciseness, much of the following description is in the context of select embodiments that include an elastic polymeric component and a loadable polymeric component.

In some embodiments, one or more linkers are associated with the one or more polymeric components. For example, in some embodiments, the linker is embedded within and may separate or link two or more portions of an elastic polymeric component.

In certain embodiments, the linker is embedded within and may separate or link two or more portions of a loadable polymeric component. In some cases, the linker is positioned between two or more different polymeric components (e.g., to couple to the two or more different polymeric components). For example, in some embodiments, two elastic polymeric components are coupled by a linker. In certain embodiments, two loadable polymeric components are coupled by a linker. In some cases, an elastic polymeric component is coupled to a loadable polymeric component by a linker. In some embodiments, the structure may comprise a combination of arrangements of polymeric components and linkers.

Figure 1B:
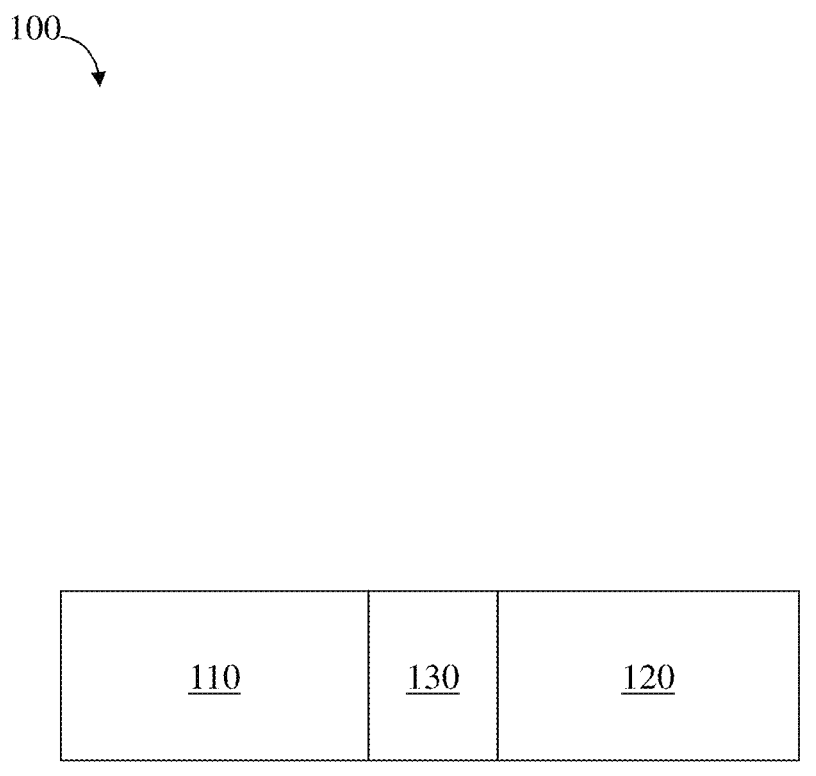

In certain embodiments, a first polymeric component and a second polymeric component are coupled by a linker. For example, as illustrated in FIG. 1B, structure 100 comprises first polymeric component 110 coupled with a second polymeric component 120 via linker 130. Linkers and suitable linker materials are described in more detail, below.

In some embodiments, the linker is embedded within and may separate or link two or more portions of a first polymeric component or a second polymeric component. For example, in certain embodiments, the linker does not couple the first polymeric component and the second polymeric component, but is embedded within the first polymeric component or the second polymeric component and may separate or link two or more portions of such component, such that when the linker degrades the component breaks apart (e.g., such that the structure or a part of the structure is removed).

In some embodiments, the structure is designed such that the mechanism for delivery is different from the mechanism for degradation. For example, linkers (e.g., enteric linkers described below) may be attached to, fused to, bonded with, embedded within, or otherwise associated with a loadable material (e.g., a loadable polymeric component) which comprises the bulk of the structure. Materials may be selected so that when the loadable material/linker composite is exposed to therapeutic, diagnostic, and/or enhancement agents for loading, loading may be selective within the loadable material, with release of therapeutic, diagnostic, and/or enhancement agents from the loadable material occurring via diffusion or slow matrix degradation. In some embodiments, the loadable material has particular mechanical properties such that the loadable material resists brittle breakage but is sufficiently stiff such that it may withstand internal physiological mechanical, chemical, and/or biological challenges to facilitate the ability to maintain residence of the structure or at least the loaded material components of the structure for a desired time interval. In some embodiments, loading of such therapeutic, diagnostic, and/or enhancement agents may be minimized within the separate linker material, and the separate linker material may be configured for control/tuning of degradation/dissolution of the retention/delivery structure and/or certain of the loadable material portions of the retention/delivery structure. By separating the mechanism of delivery (e.g., slow release from relatively stable loadable material portions) from the mechanism of controllable degradation (e.g., more rapid degradation of the linker(s),) the retention/delivery structure may be advantageously configured to prevent burst release of therapeutic, diagnostic, and/or enhancement agents upon degradation/dissolution.

Figure 1C:
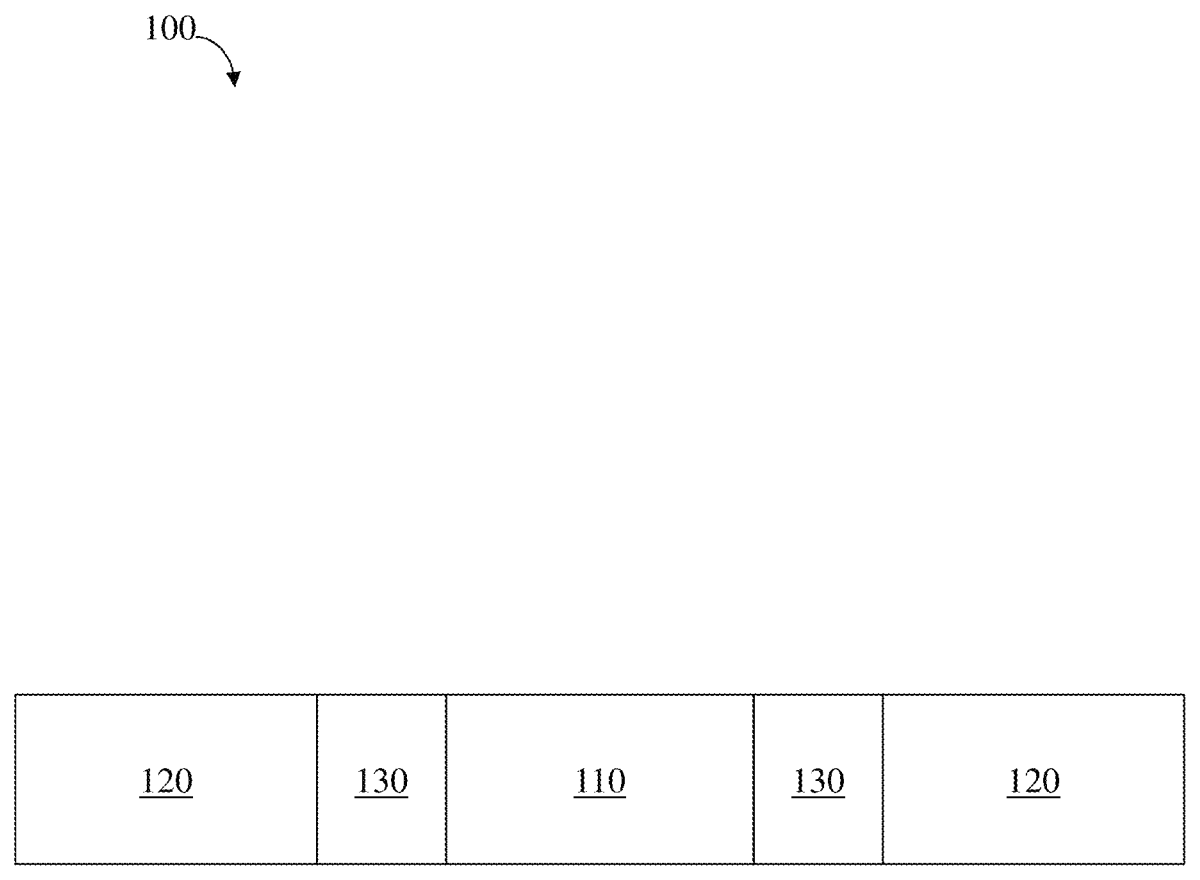

In some embodiments, the structure comprises multiple polymeric components and/or multiple linkers. In certain embodiments, the structure comprises one or more, two or more, three or more, four or more, or five or more polymeric components of a first material. In some embodiments, the structure comprises one or more, two or more, three or more, four or more, or five or more polymeric components of a second material. More complex structures and more types of polymeric materials are possible. In certain embodiments, the structure comprises one or more, two or more, three or more, four or more, or five or more, etc. linkers. In an illustrative embodiment, as illustrated in FIG. 1C, structure 100 comprises a polymeric component 110 of a first type coupled with two polymeric components 120 of a second type via two linkers 130. Those skilled in the art would be capable of selecting additional various arrangements of polymeric components and linkers based upon the teachings of the specification. Additional exemplary arrangements are described in more detail below.

In some embodiments, the retention structure comprises an elastic polymeric component. In certain embodiments, the use of an elastic polymeric component may impart favorable mechanical properties to the structure. For example, in some cases, the structure may be configured for undergoing relatively high compressive forces (e.g., compressive forces present within the stomach and/or intestine of a subject) such that the structure does not break and/or is retained at a location internally of the subject (e.g., at or above an orifice such as the pylorus). In certain embodiments, the structure may be configured for being folded (e.g., without breaking). For example, the elastic polymeric component may be configured for undergoing relatively high levels of bending stresses without breaking and/or without being permanently significantly deformed. In some embodiments, the elastic polymeric component and/or the structure containing it may be configured for substantial recoil. That is to say, after mechanically deforming the elastic polymeric component and/or the structure comprising the elastic polymeric component, the structure may return substantially to its original configuration prior to the mechanical deformation being applied (e.g., the elastic polymeric component may be characterized by substantially minimal creep deformation).

Appropriate screening tests may be used to determine suitable materials for use as the elastic polymeric component. For example, the elastic polymeric component may be tested for the capability of undergoing at least about 45 degrees, at least about 60 degrees, at least about 90 degrees, at least about 120 degrees, at least about 150 degrees, or about 180 degrees of mechanical bending deformation without breaking. In certain embodiments, the elastic polymeric component may be configured for undergoing up to and including about 180 degrees, up to and including about 150 degrees, up to and including about 120 degrees, up to and including about 90 degrees, or up to and including about 60 degrees of mechanical bending deformation without breaking. Any and all closed ranges that have endpoints within any of the above-referenced ranges are also possible (e.g., between about 45 degrees and about 180 degrees, between about 60 degrees and about 180 degrees, between about 60 degrees and about 120 degrees, between about 90 degrees and about 180 degrees). Other ranges are also possible.

In some cases, the elastic polymeric component may be configured for remaining in a deformed configuration (e.g., at least about 45 degrees of mechanical bending deformation) for a relatively prolonged period of time—for example, in some embodiments, the elastic polymer component has a shelf-life in such a deformed configuration of at least about 24 hours, at least about 1 week, at least about 1 month, at least about 1 year, or at least about 2 years—and still be configured for returning (i.e. recoiling) substantially to its pre-deformation configuration. In certain embodiments, the elastic polymer component has a shelf life in a deformed configuration of up to and including about 3 years, up to and including about 2 years, up to and including about 1 year, up to and including about 1 month, or up to and including about 1 week and be configured for returning (i.e. recoiling) substantially to its pre-deformation configuration. Any and all closed ranges that have endpoints within any of the above-referenced ranged are also possible (e.g., between about 24 hours and about 3 years, between about 1 week and 1 year, between about 1 year and 3 years). Other ranges are also possible.

In some embodiments, the elastic polymeric component is relatively flexible. In certain embodiments, the elastic polymeric component may be selected such that it is configured for undergoing large angle deformation for relatively long periods of time without undergoing significant non-elastic deformation. In some such embodiments, the elastic polymeric component may have a strength of recoil sufficient to substantially return the elastic polymeric component to its pre-deformed shape within less than about 30 minutes, within less than about 10 minutes, within less than about 5 minutes, or within less than about 1 minute after release of the mechanical deformation. Those skilled in the art would understand that returning to its pre-deformed shape shall be understood to not require absolute conformance to a mathematical definition of shape, but, rather, shall be understood to indicate conformance to the mathematical definition of shape to the extent possible for the subject matter so characterized as would be understood by one skilled in the art most closely related to such subject matter.

In some embodiments, the elastic polymeric component has a particular elastic modulus. In some embodiments, the elastic modulus of the elastic polymeric component ranges between about 0.1 MPa and about 30 MPa. In some embodiments, the elastic modulus of the elastic polymeric component is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 20 MPa, or at least about 25 MPa. In certain embodiments, the elastic modulus of the elastic polymeric component up to and including about 30 MPa, up to about 25 MPa, up to and including about 20 MPa, up to and including about 10 MPa, up to and including about 5 MPa, up to and including about 2 MPa, up to and including about 1 MPa, up to and including about 0.5 MPa, up to and including about 0.3 MPa, or up to and including about 0.2 MPa. Any and all closed ranges that have endpoints within any of the above referenced ranges are also possible (e.g., between about 0.1 MPa and about 30 MPa, between about 0.3 MPa and about 10 MPa). Other ranges are also possible. Those skilled in the art would be capable of selecting suitable methods for determining the elastic modulus of a polymeric component including, for example, tensile mechanical characterization under ASTM D638 and/or compressive mechanical characterization under ASTM D575.

In some embodiments, the elastic polymeric component undergoes a relatively low amount of creep during mechanical deformation. For example, in certain embodiments, the elastic polymeric component has a minimum creep rate of less than or equal to about 0.3 mm/mm/hr, less than or equal to about 0.2 mm/mm/hr, less than or equal to about 0.1 mm/mm/hr, less than or equal to about 0.08 mm/mm/hr, less than or equal to about 0.05 mm/mm/hr, less than or equal to about 0.03 mm/mm/hr, or less than or equal to about 0.02 mm/mm/hr. In certain embodiments, the elastic polymeric component has a minimum creep rate of at least about 0.01 mm/mm/hr, at least about 0.02 mm/mm/hr, at least about 0.03 mm/mm/hr, at least about 0.05 mm/mm/hr, at least about 0.08 mm/mm/hr, at least about 0.1 mm/mm/hr, or at least about 0.2 mm/mm/hr. Any and all closed ranges that have endpoints within any of the above referenced ranges are also possible (e.g., between about 0.01 mm/mm/hr and about 0.3 mm/mm/hr, between about 0.02 mm/mm/hr and about 0.1 mm/mm/hr, between about 0.02 mm/mm/hr and about 0.05 mm/mm/hr, between about 0.05 mm/mm/hr and about 0.3 mm/mm/hr). Other ranges are also possible. Minimum creep rate can be determined, in some embodiments, according to ASTM D-638. Briefly, a sheet of the elastic polymeric material is prepared, as described below, and cut into a standard dumbbell die. The specimens can be loaded into grips of an Instron testing machine and the gauge length measured using a digital micrometer. A substantially constant stress corresponding to 30% of the ultimate tensile strength of each material may be applied to the specimens for 60 min at constant temperature (e.g., room temperature) and the creep (in mm/mm) versus time (in hours) can be plotted. The minimum creep rate is the slope of the creep vs. time curve prior to secondary creep.

Those skilled in the art given the guidance and teaching of this specification would be capable of determining suitable methods for tuning the mechanical properties (e.g., elastic modulus, creep behavior) of the elastic polymeric component by, for example, varying the molar ratios of monomeric and/or polymeric units (e.g., increasing the amount of high molecular weight polycaprolactone or other polymers used in the elastic polymeric component), varying polymer cross-linking density, varying the concentration of cross-linking agents used in the formation of the polymer, varying the crystallinity of the polymer (e.g., by varying the ratio of crystalline and amorphous regions in the polymer) and/or the use of additional or alternative materials (e.g., incorporating materials such as bis(isocyanatomethyl)-cyclohexane).

In some embodiments, the elastic polymeric component does not substantially swell in the presence of biological fluids such as blood, water, bile, gastric fluids, combinations of these, or the like. In some embodiments, the elastic polymer component swells between about 0.01 vol % and about 10 vol % in a biological fluid as compared to the volume of the elastic polymer component in the dry state (e.g., at atmospheric conditions and room temperature). For example, in certain embodiments, the elastic polymeric component swells by less than about 10 vol %, less than about 5 vol %, less than about 2 vol %, or less than about 1 vol % in a non-stirred, gastric fluid or simulated gastric fluid at physiological temperature as compared to the volume of the elastic polymeric component in the dry state (e.g., at atmospheric conditions and room temperature).

In some cases, the residence structure swells by less than about 10 vol %, less than about 5 vol %, less than about 2 vol %, or less than about 1 vol % in a non-stirred, gastric fluid or simulated gastric fluid at physiological temperature as compared to the volume of the residence structure in the dry state (e.g., at atmospheric conditions and room temperature). Those skilled in the art would be capable of selecting suitable methods for determining the amount of swelling of an elastic polymeric component or structure based upon the teachings of this specification including, for example, measuring the volume of the elastic polymeric component or structure in the dry state at atmospheric conditions and room temperature, submerging the elastic polymeric component or structure in the non-stirred, gastric fluid or simulated gastric fluid at physiological temperature and measuring the percent change in volume of the component after about 60 minutes. The volume of the structure may be determined by, for example, fluid displacement methods known in the art and/or by 3D scanning technology.

The elastic polymeric component is preferably biocompatible. The term "biocompatible," as used in reference to a polymeric component, refers to a polymer that does not invoke a substantial adverse reaction (e.g., deleterious immune response) from an organism (e.g., a mammal), a tissue culture or a collection of cells, or invokes only a reaction that does not exceed an acceptable level. In some embodiments, the elastic polymeric component comprises polymers, networks of polymers, and/or multi-block combinations of polymer segments, that may comprise polymers or polymer segments that are for example: polyesters—such as including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers—such as including but not limited to, poly(ethylene oxide) and poly(propylene oxide); polysiloxanes—such as including but not limited to, poly(dimethylsiloxane); polyamides—such as including but not limited to, poly(caprolactam); polyolefins—such as including but not limited to, polyethylene; polycarbonates—such as including but not limited to poly(propylene oxide); polyketals; polyvinyl alcohols; polyoxetanes; polyacrylates/methacrylates—such as including but not limited to, poly(methyl methacrylate) and poly(ethyl-vinyl acetate); polyanhydrides; and polyurethanes. In some embodiments, the polymer is cross-linked. In some embodiments, the elastic polymeric component comprises a polymer composite comprising two or more chemically similar polymers or two or more chemically distinct polymers. In an exemplary embodiment, the elastic polymeric component comprises an isocyanate cross-linked polyurethane generated from low molecular weight monomers such as polycaprolactone. In some such embodiments, the low molecular weight monomers comprise one or more hydroxyl functional groups (e.g., a diol, a triol)

In certain embodiments, the elastic polymeric component comprises an enteric polymer such as an enteric elastomer. Enteric polymers and enteric elastomers are described in more detail, below.

According to some embodiments, a retention structure is configured to load relatively high levels (e.g., masses) of one or more active substances, such as therapeutic, diagnostic, and/or enhancement agents. In some embodiments, the structure is formed from one or more of a variety of materials which a have desirable properties for controlled active substance loading and release, including, but not limited to polycaprolactone (PCL), poly(ethylene-co-vinyl acetate), and polyethylene glycol (PEG). For example, in some embodiments, the loadable polymeric component is a polymeric component configured to load relatively high levels of the active substances and configured to have desirable properties for controlled active substance loading and release. In some embodiments, the loadable polymeric component comprises a drug-loadable polymer matrix. In an exemplary embodiment, the loadable polymeric component comprises polycaprolactone. Polycaprolactone is a degradable polyester (degradable by hydrolysis of ester linkages under physiological conditions) with a relatively low melting point of around 60° C. In some embodiments, the loadable polymeric component is selectively degradable under a particular set of conditions (e.g., at a particular range of pH and/or temperatures). In certain embodiments, the loadable polymeric component is biodegradable (e.g., in vivo.)

In some embodiments, the loadable polymeric component is configured to load relatively high levels of the active substances and/or comprises a drug loadable polymer matrix. For example, in certain embodiments, the structure comprises the loadable polymeric component in amount of at least about 60 wt %, at least about 70 wt % at least about 80 wt %, at least about 90 wt %, or at least about 93 wt % of the total structure weight. In some embodiments, the structure comprises the loadable polymeric component in an amount of up to and including about 95 wt %, up to and including about 93 wt %, up to and including about 90 wt %, up to and including about 80 wt %, or up to and including about 70 wt % of the total structure weight. Any and all closed ranges that have endpoints within any of the above-referenced ranges are also possible (e.g., between about 60 wt % and about 95 wt %). For example, in some embodiments, between about 60 wt % and about 95 wt % of the structure comprises a polymeric component capable and configured to load relatively high levels of active substances and/or therapeutic agents. The presence of a loadable polymeric component having the ability to load relatively high levels of active substances in an amount greater than about 60 wt % (e.g., greater than about 80 wt %, greater than about 90 wt %) of the overall structure offers several advantages structure including, for example, the ability to release the active substance (e.g., therapeutic agent) over relatively long periods of time (e.g., at least about 24 hours, at least about 48 hours, at least about 7 days, at least about 1 month) from the structure, and/or the ability to tune the release rate and/or duration of release of the active substance.

Several screening tests may be used to select suitable materials for use as the loadable polymeric component. For example, the loadable polymeric component may be selected such that the loadable polymeric component has a flexural moduli greater than about 100 MPa, greater than about 120 MPa, greater than about 150 MPa, or greater than about 200 MPa. In some embodiments, the loadable polymeric component has a flexural modulus less than or equal to about 250 MPa, less than or equal to about 200 MPa, less than or equal to about 150 MPa, or less than or equal to about 120 MPa. Any and all closed ranges that have endpoints within any of the above referenced ranges are also possible (e.g., between about 100 MPa and about 250 MPa). Other ranges are also possible. Those skilled in the art would be capable of selecting suitable methods for determining the flexural moduli of a polymeric component including, for example, plotting the flexural stress versus strain and taking the slope of the linear portion of the curve. The flexural moduli of the loadable polymeric component may be selected to impart desirable features to the structure including, for example, the ability to fold and/or bend such that the structure can be encapsulated without breaking and/or the ability to withstand compressive forces such as those within the gastric cavity.

In certain embodiments, the loadable polymeric component may be selected to have a flexural strength of at least about 10 MPa. For example, in some embodiments, the loadable polymeric component has a flexural strength of at least about 10 MPa, at least about 15 MPa, at least about 20 MPa, at least about 30 MPa, or at least about 40 MPa. In certain embodiments, the loadable polymeric component has a flexural strength of less than or equal to about 50 MPa, less than or equal to about 40 MPa, less than or equal to about 30 MPa, less than or equal to about 20 MPa, or less than or equal to about 15 MPa. Any and all closed ranges that have endpoints within any of the above referenced ranges are also possible (e.g., between about 10 MPa and about 50 MPa). Other ranges are also possible. Those skilled in the art would be capable of selecting suitable methods for determining the flexural strength of the loadable polymeric component including, for example, determining the flexural stress at failure of the polymeric material. The flexural strength of the loadable polymeric component may be selected to impart desirable features to the structure including, for example, the ability to fold and/or bend such that the structure can be encapsulated without breaking and/or the ability to withstand compressive forces such as those within the gastric cavity.

The loadable polymeric component materials may be selected such that they maintain their mechanical properties over a residence time period(e.g., during the release of the active substance and/or during residence in a body cavity). Residence time periods are described in more detail, below. In some embodiments, the loadable polymeric component materials are selected such that the structure may be retained within a cavity located internally of the subject (e.g., a gastric cavity) for at least 24 hours, at least 48 hours, at least one week, at least one month, or at least one year. In certain embodiments, the loadable polymeric component materials are selected such that the structure may be retained within a cavity location internally of the subject for up to and including about 2 years, up to and including about 1 year, up to and including about 1 month, up to and including about 1 week, or up to and including about 48 hours. Any and all closed ranges that have endpoints within any of the above-referenced ranges are also possible (e.g., between about 24 hours and about 2 years, between about 48 hours and about 2 years, between about 1 week and about 1 year). Other ranges are also possible.

In certain embodiments, the loadable polymeric component is selected such that the materials stabilize an active substance (e.g., a therapeutic agent) loaded into the component in physiological environments such as the acidic environment of the stomach for the desired duration of retention.

In some embodiments, one or more polymeric components and/or one or more linkers may comprise a food grade cross-linked (FGC) polymer. For example, in certain embodiments, the loadable polymeric component comprises a food grade catalyst catalyzed polymer. The use of a food grade cross-linked polymer offers several advantages over non-food grade polymers including easier FDA approval, low cytotoxicity, and/or a reduced need (or substantially no need) to remove toxic catalysts after polymerization. In some embodiments, the food grade cross-linked polymer comprises food grade ingredients cross-linked and/or polymerized using a food grade catalyst. Food grade cross-linked polymers generally may have advantageous combinations of properties including mechanical strength, biocompatibility and/or moldability. In some cases, the FGC polymer advantageously can provide controlled release of the therapeutic agent, while comprising little to no potentially harmful auxiliary materials (e.g., solvents, catalysts, excipients) which, in some cases, may be toxic agents. In some embodiments, the FGC polymer is formed by the reaction of one or more monomers in the presence of a food grade catalyst. The use of food grade catalysts to form FGC polymers can offer several advantages including, for example, the formation of components which contain primarily (or only) FDA approved ingredients, and biocompatibility. In certain embodiments, the FGC polymer comprises ester bonds such that, for example, the FGC polymer is degradable under physiological conditions. Advantageously, the FGC polymer may comprise a polymeric material (e.g., a thermoset polymeric material) having the strength and integrity of epoxy resins, the biomedical applicability of hydrogels, and/or the moldability of vitrimers.

In some embodiments, the FGC polymer is cross-linked. In certain embodiments, the FGC polymer is substantially amorphous. In one embodiment, the FGC polymer is useful as a loadable polymeric component of a retention structure and is a derived from oligomeric or polymeric strands or chains which have undergone crosslinking via reactions that do not preclude inclusion of sensitive therapeutics (e.g., active substances may be loaded and released directly into the FGC polymer). The FGC polymer may be softer than conventional hardened resins and may be characterized by a lower Young's modulus and crosslinking density than conventional hardened resins. In certain embodiments, in contrast to a shape memory polymer which generally returns to its original form after it has been stretched or otherwise stressed, the FGC polymer may remain fixed in its new shape after it has been molded into a new position.

In some embodiments, the FGC polymer is formed by the reaction of two or more polyfunctional monomers (e.g., a first polyfunctional monomer and a second polyfunctional monomer). In certain embodiments, the FGC polymer is formed by the reaction of two or more, three or more, four or more, or five or more polyfunctional monomers. In some embodiments, each polyfunctional monomer comprises a reactive functional group. In certain embodiments, two or more reactive functional groups may form a covalent bond with one another. For example, in some cases, the reaction of a first reactive functional group and a second reactive functional group forms a covalent bond between the first reactive functional group and the second reactive functional group. In other embodiments, the reaction between two or more reactive functional groups is a Michael-addition. In other embodiments, the reaction between two or more reactive functional groups is a cycloaddition reaction, especially a Diels-Alder reaction.

In some embodiments, one or more polyfunctional monomers is bifunctional. In certain embodiments, one or more polyfunctional monomers is trifunctional. In some cases, one or more polyfunctional monomers may be tetrafunctional, pentafunctional, hexafunctional, or have higher orders of functionality. In a particular embodiments, the FGC polymer is formed by the reaction of one or more bifunctional monomers and one or more trifunctional monomers.

In one embodiment, the FGC polymer may be represented by Formula (I).

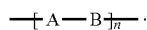

Formula (I)

wherein A is derived from at least one polyfunctional monomer containing at least two reactive functional groups, and B is derived from at least one polyfunctional monomer containing at least two reactive functional groups, and wherein the compound of Formula (I) comprises crosslinked bonds. For example, in a particular embodiment, the FGC polymer comprising the structure as in Formula (I) is formed by the reaction of a first polyfunctional monomer comprising two reactive functional groups and a second polyfunctional comprising three reactive functional groups. In another embodiment, the FGC polymer comprising the structure as in Formula (I) is formed by the reaction of a first polyfunctional monomer comprising two reactive functional groups, a second polyfunctional monomer different than the first polyfunctional monomer comprising two reactive functional groups, and a third polyfunctional monomer comprising three reactive functional groups. In some such embodiments, the reactive functional groups of the first polyfunctional monomer may be the same or different as the reactive functional groups of the second polyfunctional monomer and/or the third polyfunctional monomer. For example, the reactive groups of the first polyfunctional monomer may react with (and form a covalent bond with) the reactive groups of the second polyfunctional monomer and/or the third polyfunctional monomer.

In some embodiments, one or more polyfunctional monomers contain an oligomeric moiety. In certain embodiments, the FGC polymer of Formula (I) is further characterized by the presence of at least two reactive groups capable of forming a crosslink bond.

In certain embodiments, the compound of Formula (I) is prepared by combining two or more polyfunctional monomers, and then incubating the mixture at a temperature sufficient to initiate polymerization to reach the gel point. In some embodiments, the two or more polyfunctional monomers are combined in the presence of a catalyst. In certain embodiments, two or more polyfunctional monomers are combined in the presence of a subunit compound, in the presence of an active substance, or both.

In some embodiments, the polyfunctional monomer has a structure as in Formula (II):

wherein $Q^1$ and $Q^2$ are the same or different and a reactive functional group and L has a structure as in Formula (III):

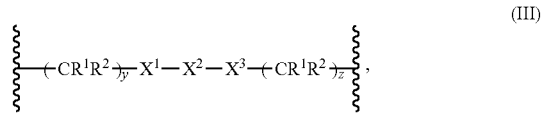

wherein $\xi$ indicates a point of connection to $Q^1$ and $Q^2$.

In some embodiments, the polyfunctional monomer has a structure as in:

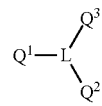

wherein $Q^1$, $Q^2$, and $Q^3$ are the same or different and a reactive functional group and L has a structure as in Formula (III).

In some embodiments, $X^1$, $X^2$, and $X^3$ are the same or different and are absent or selected from the group consisting of $(CR^1R^2)_m$, a heteroatom, an alkenyl, an alkynyl, a cycloalkyl, an aryl, a heterocyclic group, a heteroaryl group, and an oligomeric group. In certain embodiments, $X^1$, $X^2$, and/or $X^3$ are absent.

In certain embodiments, m is zero or any integer. For example, in some embodiments, m is 0. In certain embodiments, m is 1-3, 2-4, 3-6, 4-8, 5-10, 8-16, 12-24, 20-30, 25-50, 40-60, 50-100, 75-150, 125-200, 150-300, 250-500, 400-600, 500-800, or 750-1500. In some cases, m is 1-3. In certain embodiments, m is 2-4. In some cases, m is 4-8. In some embodiments, m is 8-16. The value of m may be selected to impart certain properties in the FGC polymer (e.g., crosslink density, Young's elastic modulus).

In some embodiments, y is zero or any integer. For example, in some embodiments, y is 0. In certain embodiments, y is 1-3, 2-4, 3-6, 4-8, 5-10, 8-16, 12-24, 20-30, 25-50, 40-60, 50-100, 75-150, 125-200, 150-300, 250-500, 400-600, 500-800, or 750-1500. In some cases, y is 1-3. In certain embodiments, y is 2-4. In some cases, y is 4-8. In some embodiments, y is 8-16. The value of y may be selected to impart certain properties in the FGC polymer (e.g., crosslink density, Young's elastic modulus).

In certain embodiments, z is zero or any integer. For example, in some embodiments, z is 0. In certain embodiments, z is 1-3, 2-4, 3-6, 4-8, 5-10, 8-16, 12-24, 20-30, 25-50, 40-60, 50-100, 75-150, 125-200, 150-300, 250-500, 400-600, 500-800, or 750-1500. In some cases, z is 1-3. In certain embodiments, z is 2-4. In some cases, z is 4-8. In some embodiments, z is 8-16. The value of z may be selected to impart certain properties in the FGC polymer (e.g., crosslink density, Young's elastic modulus).

In a particular embodiment, m+y+z is zero. In certain embodiments, m+y+z is 1. In some cases, m+y+z is an integer and is 2 or greater.

In some embodiments, each $R^1$ and $R^2$ are the same or different and are selected from the group consisting of hydrogen, an aliphatic group, a halogen, a hydroxyl, a carbonyl, a thiocarbonyl, an oxo, an alkoxy, an epoxy, a phosphoryl, a phosphate, a phosphonate, a phosphinate, an amino, an amido, an amidine, an imine, a cyano, a nitro, an azido, a thiol, an alkylthio, a sulfate, a sulfonate, a sulfamoyl, a sulfonamido, a sulfonyl, a cycloalkyl, a heterocyclyl, an aralkyl, and an aromatic or heteroaromatic or a Michael acceptor, wherein any two or more $R^1$ and $R^2$ groups may be bonded together so as to form a ring system. In certain embodiments, each $R^1$ and/or $R^2$ may be $Q^3$ (i.e. a reactive functional group).

In an exemplary embodiment, the polyfunctional monomer has the structure as in Formula (IV):

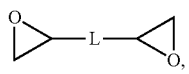

(IV)

wherein L is as described above. In another exemplary embodiments, the polyfunctional monomer has the structure as in:

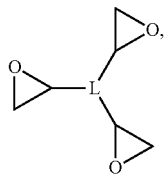

wherein L is as described above. In yet another exemplary embodiment, the polyfunctional monomer has a structure as in Formula (V) or Formula (VI):

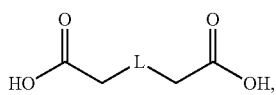

(V)

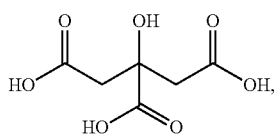

(VI)

wherein L is described above. In some embodiments, the FGC polymer is formed by the reaction of a first polyfunctional monomer having a structure as in Formula (IV) with a second polyfunctional monomer having a structure as in Formula (V) or Formula (VI).

Polyfunctional monomers described herein may comprise at least two, at least three, at least four, or at least five reactive functional groups. For example, in some embodiments, $Q^1$, $Q^2$, and $Q^3$ may be the same or different and an electrophilic functional groups or a nucleophilic functional group.

In some embodiments, one or more reactive groups (e.g., $Q^1$, $Q^2$, and/or $Q^3$) is an electrophilic functional groups. For example, a monomer may comprise at least two, at least three, at least four, or at least five electrophilic functional groups. Non-limiting examples of suitable electrophilic functional groups include alkenes, alkynes, esters (e.g., N-hydroxysuccinimide ester), acrylates, methacrylates, acyl halides, acyl nitriles, alkyl halides, aldehydes, ketones, alkyl sulfonates, anhydrides, epoxides, haloacetamides, aziridines, and diazoalkanes.

In certain embodiments, one or more reactive functional groups (e.g., $Q^1$, $Q^2$, and/or $Q^3$) is a nucleophilic functional groups. For example, a monomer may comprise at least two, at least three, at least four, or at least five nucleophile reactive functional groups. Non-limiting examples of suitable nucleophilic functional groups include alcohols, amines, anilines, phenols, hydrazines, hydoxylamines, carboxylic acids, alkoxide salts, alkenes, thiols, and glycols.

The polyfunctional monomers described herein may comprise at least one electrophilic functional group and at least one nucleophilic functional group. For example, in an exemplary embodiment, the first polyfunctional monomer comprises both an electrophilic functional group and a nucleophilic functional group. In certain embodiments, the first polyfunctional monomer comprises two or more electrophile functional groups and the second polyfunctional monomer comprises two or more nucleophile functional groups.

In some cases, the reaction of an electrophilic functional group and a nucleophilic functional group form a bioresponsive bond such as an ester bond, an ether bond, an amide bond, an amine bond, or a thioether bond. For example, in certain embodiments, the FGC polymer comprises an ester bond formed by the reaction of an electrophilic functional group and a nucleophilic functional group. In some embodiments, the FGC polymer comprises an ether bond formed by the reaction of an electrophilic functional group and a nucleophilic functional group. Other bonds are also possible.

In some embodiments the FGC polymer is formed by the reaction of two or more polyfunctional monomers and an additional monomeric unit. In some embodiments, the additional monomeric unit comprises a compound containing one or more carboxylic acid derivatives. In some embodiments, the additional monomeric unit is a single compound containing at least one ester, amide or thioester group, or a mixture of compounds containing at least one ester, amide or thioester. In certain embodiments, the additional monomeric unit is a compound containing a lactone, lactam or thiolactone group. In certain embodiments, the additional monomeric unit is a naturally occurring lactone or lactam. In another embodiment, the additional monomeric unit lactone-containing or lactam-containing compound selected from the FDA's "Generally Recognized as Safe" Substances database and/or listed in 21 C.F.R. § 182. In certain embodiments, the additional monomeric unit is selected γ-decalactone, δ-decalactone, ω-pentadecalactone, caprolactam, and mixtures thereof.

In certain embodiments of the invention, the additional monomeric unit does not contain a primary or secondary amine moiety.

In some embodiments, the molar ratio of the first polyfunctional monomer (e.g., comprising electrophilic reactive groups) to a mixture of additional polyfunctional monomers (e.g., comprising nucleophilic reactive groups) and/or additional monomeric units ranges between about 10:1 and about 1:10. In an exemplary embodiment, the molar ratio of the first polyfunctional monomer to a mixture of additional polyfunctional monomers and/or monomeric units is about 1:1. In certain embodiments, the molar ratio of first polyfunctional monomer to a mixture of additional polyfunctional monomers and/or monomeric units is at less than about 10:1, less than about 8:1, less than about 6:1, less than about 4:1, less than about 2:1, less than about 1.5:1, less than about 1:1, less than about 1.5:1, less than about 1:2, less than about 1:4, less than about 1:6, or less than about 1:8. In some embodiments, the molar ratio of first polyfunctional monomer to a mixture of additional polyfunctional monomers and/or monomeric units is greater than or equal to about 1:10, greater than or equal to about 1:8, greater than or equal to about 1:6, greater than or equal to about 1:4, greater than or equal to about 1:2, greater than or equal to about 1:1.5, greater than or equal to about 1:1, greater than or equal to about 1.5:1, greater than or equal to about 2:1, greater than or equal to about 4:1, greater than or equal to about 6:1, or greater than or equal to about 8:1. Any and all closed ranges that have endpoints within any of the above-referenced ranges are also possible (e.g., between about 10:1 and about 1:10, between about 1:4 and about 4:1, between about 1:2 and about 2:1).

In some such embodiments, the second polyfunctional monomer is present in the mixture of additional polyfunctional monomers and/or monomeric units in an amount of at least about 10 mol %, at least about 20 mol %, at least about 25 mol %, at least about 50 mol %, at least about 75 mol %, at least about 90 mol %, or at least about 99 mol %. In certain embodiments, the second polyfunctional monomer is present in the mixture of additional polyfunctional monomers and/or monomeric units in an amount of less than or equal to about 99.9 mol %, less than or equal to about 99 mol %, less than or equal to about 90 mol %, less than or equal to about 75 mol %, less than or equal to about 50 mol %, less than or equal to about 25 mol %, or less than or equal to about 20 mol %. Any and all closed ranges that have endpoints within any of the above-referenced ranges are also possible (e.g., between about 25 mol % and about 99.9 mol %). Other ranges are also possible.

As described above, in some embodiments, two or more polyfunctional monomers are combined (i.e. reacted) in the presence of a catalyst.

In some embodiments, the catalyst is a nucleophile. In certain embodiments, the catalyst is a base (e.g., a mild base, a weak base). In certain embodiments, the catalyst is a metal salt. In some embodiments, the catalyst is a sulfate salt of zinc such as $ZnSO_4$ and hydrates thereof.

In some embodiments, the catalyst is selected from catalysts listed in FDA's "Generally Recognized as Safe" Substances database and/or listed in 21 C.F.R. § 182. In certain embodiments, the catalyst is food grade and/or food derived catalyst.

In certain embodiments, the catalyst is an organic amine. In some embodiments, the catalyst is a tertiary amine. In some cases, the tertiary amine catalyst does not contain any amino N—H or $NH_2$ functional groups.

In some embodiments, the catalyst is an alkaloid compound. In certain embodiments, the catalyst is a purine base. Non-limiting examples of purine bases include purine, adenine, guanine, hypoxanthine, xanthine, theobromine, caffeine, uric acid and isoguanine. In an exemplary embodiment, the catalyst is caffeine.

The use of a food grade catalyst such as caffeine may offer certain advantages over traditional catalysts including easier FDA approval, low cytotoxicity, and/or a reduced need (or substantially no need) to remove the catalyst after polymerization.

In some embodiments, the catalyst (e.g., food grade catalyst) is present in the FGC polymer after the formation of the FGC polymer in an amount ranging between 0.01 mol % and about 25 mol %. In some embodiments, the FGC polymer comprises substantially no catalyst after the formation of the FGC polymer. In certain embodiments, the catalyst is present in the FGC polymer after the formation of the FGC polymer in an amount of at least about 0.01 mol %, at least about 0.05 mol %, at least about 0.1 mol %, at least about 0.5 mol %, at least about 1 mol %, at least about 2 mol %, at least about 5 mol %, at least about 10 mol %, or at least about 20 mol %. In certain embodiments, the catalyst is present in the FGC polymer after the formation of the FGC polymer in an amount of less than or equal to about 25 mol %, less than or equal to about 20 mol %, less than or equal to about 10 mol %, less than or equal to about 5 mol %, less than or equal to about 2 mol %, less than or equal to about 1 mol %, less than or equal to about 0.5 mol %, less than or equal to about 0.1 mol %, or less than or equal to about 0.05 mol %. Any and all closed ranges that have endpoints within any of the above-referenced ranges are also possible (e.g., between 1 mol % and 25 mol %, between 0.01 mol % and 5 mol %). Other ranges are also possible.

As described above, in some embodiments, the FGC polymer may be formed using three or more polyfunctional monomers. In an exemplary reaction, polypropylene oxide is reacted with citric acid, mercaptosuccinic acid, and PPO-dimethacrylate in the presence of caffeine via Michael addition to form a branched FGC polymer.

In some embodiments, the structure (e.g., the loadable polymeric component) is pre-loaded with an active substance such as a therapeutic, diagnostic, and/or enhancement agents. In other embodiments, the structure (e.g., the loadable polymeric component) is loaded with therapeutic, diagnostic, and/or enhancement agents after it is already retained at a location internal to a subject, such as a gastric cavity. In some embodiments, a structure is configured to maintain stability of therapeutic, diagnostic, and/or enhancement agents in a hostile physiological environment (e.g., the gastric environment) for an extended duration. In further embodiments, the structure is configured to control release of therapeutic, diagnostic, and/or enhancement agents with low to no potential for burst release. In some embodiments, the structure (e.g., the loadable polymeric component) is pre-loaded and/or loaded with a combination of active substances. For example, in certain embodiments, the structure comprises one or more, two or more, three or more, or four or more active substances.

Therapeutic, diagnostic, and/or enhancement agents can be loaded into polymeric materials and other drug delivery materials via standard methods including, but not limited to, powder mixing, direct addition, solvent loading, melt loading, physical blending, supercritical carbon dioxide assisted, and conjugation reactions such as ester linkages and amide linkages. Release of therapeutic, diagnostic, and/or enhancement agents can then be accomplished through methods including, but not limited to, dissolution of the loadable polymeric component comprising a polymeric matrix material, degradation of the matrix material, swelling of the matrix material, diffusion of an agent, hydrolysis, and chemical or enzymatic cleavage of conjugating bonds. In some embodiments, the active substance is covalently bound to the polymer matrix of the polymeric component (e.g., and is released as the polymer matrix degrades).

In certain embodiments, the structure is constructed and arranged to release the active substance from the loadable polymeric component(s). In certain embodiments, the active substance is designed for release from the loadable polymeric component. Such embodiments may be useful in the context of drug delivery. In other embodiments, the active substance is permanently affixed to the loadable polymeric component. Such embodiments may be useful in molecular recognition and purification contexts. In certain embodiments, the active substance is embedded within the loadable polymeric component. In some embodiments, the active substance is associated with the loadable polymeric component via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups.

According to some embodiments, the systems, structures, and methods described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. The active substance may be entrapped within the polymeric matrix or may be directly attached to one or more atoms in the polymeric matrix through a chemical bond. In certain embodiments, the active substance is covalently bonded to the polymeric matrix. In some embodiments, the active substance is bonded to the polymeric matrix through a carboxylic acid derivative. In some cases, the carboxylic acid derivative may form an ester bond with the active substance.

Agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, non-steroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, antiviral agents like entecavir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In some embodiments, the active substance is a radiopaque material such as tungsten carbide or barium sulfate.

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. § § 330.5, 331 through 361, and 440 through 460, incorporated herein by reference; drugs for veterinary use are listed by the FDA under 21 C.F.R. § § 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, prostaglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

Active substances that contain a carboxylic acid group may be directly incorporated into polymeric matrices that contain ester and hydroxyl groups without further modification. Active substances containing an alcohol may first be derivatized as a succinic or fumaric acid monoester and then incorporated into the polymeric matrix. Active substances that contain a thiol may be incorporated into olefin or acetylene-containing matrices through a sulfur-ene reaction. In other embodiments, the one or more agents are non-covalently associated with the polymeric matrices (e.g., dispersed or encapsulated within).

In other embodiments, the active substance is a protein or other biological macromolecule. Such substances may be covalently bound to the polymeric matrix through ester bonds using available carboxylate containing amino acids, or may be incorporated into polymeric material containing olefinic or acetylenic moieties using a thiol-ene type reaction. In some cases, the active substance comprises an amine functional group capable of reacting with an epoxide functional group to form an amide or ester bond. In other embodiments, the active substance is non-covalently associated with the polymeric matrix. In some such embodiments, the active substance may be dispersed or encapsulated within by hydrophilic and/or hydrophobic forces.

In some cases, the partition coefficient of the active substance in the loadable polymeric component material can be tuned. For example, if the active substance is hydrophobic, a hydrophobic polymeric material backbone may, in some cases, slow the release into aqueous solution, however, a hydrophilic polymeric material backbone should accelerate it. Additionally, a hydrophilic polymeric material backbone may, in some cases, increase the rate of water absorption into the material, expanding (e.g., swelling) the polymeric material and accelerating release rate. The expansion and dissolution of the material may be increased, in some embodiments, under conditions when free reactive groups contain ionizable moieties that become charged in the presence of aqueous media. In some such embodiments, as the material disintegrates due to ionic repulsion, the rate of release of contents may be increased via diffusion and/or better access to cleavable bonds may be imparted. Those skilled in the art would be capable of selecting suitable methods for determining the partition coefficient of the active substance including, for example, high performance liquid chromatography (HPLC).

The active substance may be associated with the polymeric matrix and/or present in the loadable polymeric component in any suitable amount. In some embodiments, the active substance is present in the loadable polymeric component an amount ranging between about 0.01 wt % and about 50 wt % versus the total loadable polymeric component weight. In some embodiments, the active substance is present in the loadable polymeric component in an amount of at least about 0.01 wt %, at least about 0.05 wt %, at least about 0.1 wt %, at least about 0.5 wt %, at least about 1 wt %, at least about 2 wt %, at least about 3 wt %, at least about 5 wt %, at least about 10 wt %, at least about 20 wt %, at least about 30 wt %, at least about 40 wt % of the total loadable polymeric component weight. In certain embodiments, the active substance is present in the loadable polymeric component in an amount of less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, or less than or equal to about 0.05 wt %. Any and all closed ranges that have endpoints within any of the above-referenced ranges are also possible (e.g., between about 0.01 wt % and about 50 wt %). Other ranges are also possible.

Advantageously, certain embodiments of the loadable polymeric components described herein may permit higher concentrations (weight percent) of active substances such as therapeutic agents to be incorporated as compared to other polymers such as certain conventional hydrogels. In some embodiments, the active substance (e.g., the active substance) may be released from the loadable polymeric component. In certain embodiments, the active substance is released by diffusion out of the loadable polymeric component. In some embodiments, the active substance is released by degradation of the loadable polymeric component (e.g., biodegradation, enzymatic degradation, hydrolysis). In some embodiments, the active substance is released from the loadable polymeric component at a particular rate. Those skilled in the art would understand that the rate of release may be dependent, in some embodiments, on the solubility of the active substance in the medium in which the loadable polymeric component is exposed, such as a physiological fluid such as gastric fluid. The ranges and description included related to the release and/or rate of release of the active substance is generally in reference to hydrophilic, hydrophobic, and/or lipophilic active substances in simulated gastric fluid (e.g., as defined in the United States Pharmacopeia (USP)). Simulated gastric fluids are known in the art and those skilled in the art would be capable of selecting suitable simulated gastric fluids based on the teachings of this specification.

In some embodiments, between 0.05 wt % to 99 wt % of the active substance initially contained in a loadable polymeric component is released (e.g., in vivo) between 24 hours and 1 year. In some embodiments, between about 0.05 wt % and about 99.0 wt % of the active substance is released (e.g., in vivo) from the loadable polymeric component after a certain amount of time. In some embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the active substance associated with the loadable polymeric component is released from the component (e.g., in vivo) within about 24 hours, within 36 hours, within 72 hours, within 96 hours, or within 192 hours. In certain embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the active substance associated with the polymeric component is released from the component (e.g., in vivo) within 1 day, within 5 days, within 30 days, within 60 days, within 120 days, or within 365 days. For example, in some cases, at least about 90 wt % of the active substance associated with the polymeric component is released from the component (e.g., in vivo) within 120 days.

In some embodiments, the active substance is released from the loadable polymeric material at a particular initial average rate as determined over the first 24 hours of release (the "initial rate") (e.g., release of the active substance at the desired location internally of the subject, such as an internal cavity). In certain embodiments, the active substance is released at an average rate of at least about 1%, at least about 2%, at least about 5%, least about 10%, at least about 20%, at least about 30%, least about 50%, at least about 75%, at least about 80%, at least about 90%, at least about 95%, or at least about 98% of the initial average rate over a 24 hour period after the first 24 hours of release. In some embodiments, the active substance is released at an average rate of less than or equal to about 99%, less than or equal to about 98%, less than or equal to about 95%, less than or equal to about 90%, less than or equal to about 80%, less than or equal to about 75%, less than or equal to about 50%, less than or equal to about %, less than or equal to about 30%, less than or equal to about 20%, less than or equal to about 10%, less than or equal to about 5%, or less than or equal to about 2% of the initial average rate over a 24 hour period after the first 24 hours of release. Any and all closed ranges that have endpoints within any of the above referenced ranges are also possible (e.g., between about 1% and about 99%, between about 1% and about 98%, between about 2% and about 95%, between about 10% and about 30%, between about 20% and about 50%, between about 30% and about 80%, between about 50% and about 99%). Other ranges are also possible.

The active substance may be released at an average rate over at least one selected continuous 24 hour period at a rate of between about 1% and about 99% of the initial rate between 48 hours and about 1 year (e.g., between 48 hours and 1 week, between 3 days and 1 month, between 1 week and 1 month, between 1 month and 6 months, between 3 months and 1 year, between 6 months and 2 years) after the initial release.

For example, in some cases, the active substance may be released at a rate of between about 1% and about 99% of the initial rate on the second day of release, the third day of release, the fourth day of release, the fifth day of release, the sixth day of release, and/or the seventh day of release.

In certain embodiments, burst release of an active substance from the loadable polymeric component is generally avoided. In an illustrative embodiment, in which at least about 0.05 wt % of the active substance is released from the loadable polymeric component within 24 hours, between about 0.05 wt % and about 99 wt % is released during the first day of release (e.g., at the location internally of the subject), and between about 0.05 wt % and about 99 wt % is released during the second day of release. Those skilled in the art would understand that the active substance may be further released in similar amounts during a third day, a fourth day, a fifth day, etc. depending on the properties of the loadable polymeric component and/or the active substance.

In certain embodiments, the active substance may be released with a pulse release profile. For example, in some embodiments, the active substance may be released on the first day after administration and during another 24 hour period such as starting during the third day, the fourth day, or the fifth day, but is not substantially released on other days. Those skilled in the art would understand that other days and/or combinations of pulsing and continuous release are also possible.

The active substance may be released at a relatively constant average rate (e.g., a substantially zero-order average release rate) over a time period of at least about 24 hours. In certain embodiments, the active substance is released at a first-order release rate (e.g., the rate of release of the active substance is generally proportional to the concentration of the active substance) of a time period of at least about 24 hours.

In some embodiments, at least a portion of the active substance loaded into the structure is released continuously (e.g., at varying rates) over the residence time period of the structure. Residence time periods are described in more detail, below.

As described above, in some embodiments, the one or more polymeric components are coupled together via one or more linkers. Those skilled in the art would understand that the term coupled generally refers to a physical linkage (which may, for example, be effected by physical and/or chemical bond forces) connecting two or more components. In some embodiments, the first (elastic) polymeric component may be coupled with the second (loadable) polymeric component via an adhesive, by chemical interactions, and/or by interpenetrating (e.g., entangled) polymer chains. For example, in some embodiments, a polymer backbone of the first polymeric component and a polymer backbone the second polymeric component are coupled via a bond such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds. The hydrogen bond may be, for example, between hydroxyl, amine, carboxyl, thiol, and/or similar functional groups.

In certain embodiments, the elastic polymeric component and the loadable polymeric component are coupled via an adhesive (e.g., a biocompatible adhesive). Non-limiting examples of suitable adhesives include biocompatible polyurethanes, cyanoacrylates, or the like.

In some embodiments, the polymer material of the elastic polymeric component and polymer material of the loadable polymeric component may interpenetrate and/or entangle such that the elastic polymeric component and the loadable polymeric component are coupled.

In some embodiments, the elastic polymeric component and a loadable polymeric component are coupled via a linker. According to some embodiments, the structure is configured to degrade, dissolve, and/or disassociate into one or more forms configured for passing through a gastrointestinal tract. In some embodiments, the structure comprises one or more linkers designed for controlled and/or tunable degradation. According to some embodiments, one or more linkers are attached to and/or incorporated into a structure to separate in a modular fashion the function of delivering therapeutic, diagnostic, and/or enhancement agents from controlling (e.g., triggering) and/or tuning degradation. Referring again to FIGS. 1B-1C, a first polymeric component 110 and a second polymeric component 120 are coupled via linker 130. In certain embodiments, two or more elastic polymeric components are coupled together via a linker. In some embodiments, two or more loadable polymeric components are coupled together via a linker. In some embodiments, the linker is embedded within a polymeric component. For example, in certain embodiments, the linker is embedded within an elastic polymeric component. In some cases, the linker may be embedded within a loadable polymeric component. In some such embodiments, the linker may degrade at a desired time and/or under desired conditions such that the elastic polymeric component or loadable polymeric component breaks apart.

The structure may comprise one or more, two or more, or three or more types of linkers. For example, in an illustrative embodiment, the structure comprises a first linker configured for degradation at a first average degradation rate and a second linker configured for degradation at a second average degradation rate under the same conditions. In certain embodiments, the linker degradation is pH dependent. In another illustrative embodiment, the structure comprises a first linker configured for degradation under a first set of physiological conditions (e.g., in (1) acidic pH such as in the stomach or, (2) alternatively, in relatively neutral pH such as in the intestines, etc.) and a second linker configured for degradation under a second set of physiological conditions different than the first set of physiological conditions (e.g., (1) in relatively neutral pH such as in the intestines, or, alternatively, (2) acidic pH such as in the stomach, etc.). In some embodiments, the second linker is not configured for substantial degradation under the first set of conditions, thereby enabling selectable and partial degradation of the structure under select condition and/or in select locations within a subject (e.g., different positions along the G.I. track.) For example, in some cases, the second linker is not substantially degradable at a first physiological condition (e.g., in acidic pH such as in the stomach) and is configured for degradation at a second physiological condition different than the first set of physiological conditions.

The term physiological condition generally refers to a set of conditions of the external or internal milieu that occurs in an organism or cellular system (e.g., in contrast to laboratory conditions). For example, in some cases, a physiological condition ranges in temperature between about 20° C. and about 40° C. (e.g., between about 35° C. and about 38° C.) and/or atmospheric pressure of about 1 atm. In certain embodiments, the physiological conditions are that of an internal organ such as the stomach, intestines, bladder, lungs, and/or heart. The linker may be selected such that the linker dissolves, degrades, mechanically weakens, and/or mechanically separates from at least one of the one or more polymeric components after a particular residence time period. The term residence time period generally refers to the length of time during which the structure (or a component of the structure) described herein is resided at a location internally of a subject as measured from the time initially present in the location internally of the subject to the time at which the structure (or such component of the structure being referenced) no longer resides at the location internally of the subject due to, for example, degradation, dissolution, and/or exit of the structure or such component(s) of the structure being referenced structure from the location internally of the subject. In an illustrative embodiment, the structure may be orally administered such that the structure resides at a location internally of the subject such as the stomach above the pylorus and exits through the pylorus into the intestine (e.g., after degradation of at least a portion of the structure), where the residence time period is measured as the length of time between when the structure initially resides in the stomach and when the structure (or a component of the structure being referenced) exits through the pylorus.

In some embodiments, the residence time period of at least a portion of the structure is at least about 24 hours, at least about 48 hours, at least about 3 days, at 7 days, at least about 1 month, at least about 6 months, or at least about 1 year. In certain embodiments, the residence time period is less than or equal to about 2 years, less than or equal to about 1 year, less than or equal to about 6 months, less than or equal to about 1 month, less than or equal to about 7 days, less than or equal to about 3 days, or less than or equal to about 48 hours. Any and all closed ranges that have endpoints within any of the above-referenced ranges are also possible (e.g., between about 24 hours and about 2 years, between about 24 hours and about 1 year, between about 48 hours and about 7 days, between about 3 days and about 1 month, between about 7 days and about 6 months, between about 1 month and about 1 year). Other ranges are also possible. The linker is preferably biocompatible.

In an exemplary embodiment, the one or more linkers are selected to mediate disassembly of the structure after, for example, delivery of an active substance for over a desired residence time period (e.g., within 24 hours, within 48 hours, within one week, within one month), and facilitate safe passage through the lower intestinal tract of the subject. Exit from an orifice such as the gastric cavity may be achieved through changes in the mechanical properties of the linker (e.g., via biodegradation) such that the ability to resist passage through an orifice (e.g., through the pylorus) is compromised, through breakage in the structure through designed linker failure, etc.

Several screening tests may be used to determine suitable materials for use as linkers, including but not limited to the ability to interface (e.g., couple) with at least a surface of the one or more of the polymeric components of the structure, possession of mechanical strength sufficient to survive encapsulation, possession of mechanical strength sufficient to undergo the compressive forces present in physiological environments such as the gastric environment, and/or selective degradation under desired times and/or conditions (e.g., pH). In some embodiments, the linker is stable within a physiological environment such as the gastric environment for a period of time (e.g., a residence time period) of at least about 24 hours, at least about 48 hours, at least about one week, at least about one month, or least about one year.

In certain embodiments, the linker comprises a material such that, under relatively neutral pH physiological conditions (e.g., such as those in the duodenum), the linker can be mechanically broken (i.e. mechanical failure) by a tensile force less than or equal to about 2 N within less than or equal to about 48 hours, or within less than or equal to about 24 hours under said neutral pH physiological conditions. In some embodiments, the mechanical failure occurs within the linker material itself, and not at the interface between the linker and the one or more polymeric components.

Non-limiting examples of suitable linker materials include polyesters—such as including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers—such as including but not limited to, poly(ethylene oxide) and poly(propylene oxide); polyamides—such as including but not limited to, poly(caprolactam); polyvinyl alcohols; polyoxetanes; polyacrylates/methacrylates—such as including but not limited to, poly(methyl methacrylate) and poly(ethylene-co-vinyl acetate); polyanhydrides; and polyurethanes.

In certain embodiments, the linker comprises an ethyl acrylate, a methyl methacrylate and/or a low content of methacrylic acid ester with quaternary ammonium groups. In some embodiments, the linker comprises a water soluble polymer such as vinylpyrrolidone-vinyl acetate copolymers (e.g., KOLLIDON® VA 64 (BASF) and KOLLIDON® SR), polyvinylpyrrolidone, cellulose acetate, hydroxypropyl methyl cellulose, or polyvinyl alcohol.

In some embodiments, the linker comprises a blend of polymers. In an exemplary embodiment, the linker comprises an isocyanate crosslinked polyurethane generated from low-molecular weight polycaprolactone monomers.

In certain embodiments, the linker comprises an enteric polymer. In some embodiments, the linker comprises an enteric elastomer. Enteric polymers and enteric elastomers are described in more detail, below.

In some embodiments, the linker and/or elastic polymeric component comprises an enteric polymer. The term enteric is generally used to describe materials that are stable at relatively highly acidic pH conditions (e.g., pH of less than about 5.5) and susceptible to dissolution at relatively alkaline pH conditions (e.g., pH of between about 6 and about 9). In some embodiments, the enteric polymer includes, but is not limited to, cellulose acetate phthalate (CAP), hypromellose (INN) hydroxypropyl methylcellulose (HPMC), and/or poly(methacrylic acid-co-ethyl acrylate) (e.g., EUDRAGIT® a available from Evonik Industries AG (Essen, Germany)).

In some embodiments, the dissolution of an enteric polymer can be triggered by, for example, ingestion of an alkali solution. In some embodiments, the enteric polymer has the capacity for dissolution between pH 4-8. According to some embodiments, the enteric polymer is selected such that the enteric polymer is stable in an acidic gastric environment (i.e., having a pH1 to pH4) but dissolves in a more alkali region of the gastrointestinal tract distal to the pylorus (i.e., having a pH greater than 5.5) and can serve as a linker.

For example, in certain embodiments, the enteric polymer does not substantially degrade at a pH ranging between about 1 and about 5. In some embodiments, the enteric polymer does not substantially degrade at a pH of at least about 1, at least about 2, at least about 3, at least about 4, or at least about 4.5. In certain embodiments, the enteric polymer does not substantially degrade at a pH of less than or equal to about 5, less than or equal to about 4.5, less than or equal to about 4, less than or equal to about 3, or less than or equal to about 2. Any and all closed ranges that have endpoints within any of the above reference ranges are also possible (e.g., between about 1 and about 4.5, between about 1 and about 5, between about 1 and 4). Other ranges are also possible.

In certain embodiments, the enteric polymer degrades substantially at a pH ranging between about 4 and about 8. In some embodiments, the enteric polymer degrades substantially at a pH of at least about 4, at least about 5, at least about 6, at least about 6.5, at least about 7, or at least about 7.5. In certain embodiments, the enteric polymer degrades substantially at a pH of less than or equal to about 8, less than or equal to about 7.5, less than or equal to about 7, less than or equal to about 6.5, less than or equal to about 6, or less than or equal to about 5. Any and all closed ranges that have endpoints within any of the above reference ranges are also possible (e.g., between about 4 and about 8, between about 5 and about 8, between about 6.5 and about 7.5). Other ranges are also possible.

Those skilled in the art would be capable of selecting suitable methods for determining degradation of the enteric polymers based upon the teachings of the specification including, determining the solubility of the enteric polymer in an aqueous solution having a pH of less than about 3 and/or dissolving the enteric polymer in aqueous solution having a pH of greater than or equal to about 6, measured at body temperature (e.g., between about 35° C. and about 38° C.) over time period of between about 2 and about 40 days. In some embodiments, the enteric polymer that does not substantially degrade behaves such that less than about 10%, less than about 5%, or less than about 2% of the enteric polymer dissociates from the rest of enteric polymer. In certain embodiments, the enteric polymer that substantially degrades behaves such that at least about 1%, at least about 2%, or at least about 5% of the enteric polymer dissociates from the remainder of the polymeric composite.

According to some embodiments, a structure is configured to maintain safety with low to no potential for intestinal obstruction and/or perforation. Controlled degradation is important, in some cases, for mitigating the risk of gastrointestinal obstruction. In some embodiments, the linker is designed to dissolve distal to the pylorus. In some embodiments, a linker is attached to and/or incorporated into a structure so that upon degradation/dissolution of the linker, the structure breaks into smaller structures configured for passing through a gastrointestinal tract (e.g., traversing the ileocecal valve) without obstruction. In an illustrative embodiment, the linker does not substantially dissolve and/or degrade when located in the stomach of a subject (e.g., having a pH ranging between about 1 and about 5) and substantially dissolves when located (e.g., after passing through the pylorus) in the intestines (e.g., having a pH ranging between about 6.7 and about 7.4).

In some embodiments, the enteric polymer is an enteric elastomer. For example, in some embodiments, the linker comprises a material selected such that it has both enteric and elastic properties. For example, in some embodiments, the linker comprises an enteric elastomer that has an elastic modulus between about 0.1 MPa and about 100 MPa at relatively highly acidic pH conditions (e.g., pH of less than about 5.5) and is susceptible to dissolution at relatively alkaline pH conditions.

In certain embodiments, at least one dimension of the enteric elastomer exhibits reversible elongation when the dimension is deformed from its initial length to a length that is less than about 50% of its original length and/or when the dimension is deformed from its initial length to a length that is at least about 1500% of its initial length. That is to say, in some embodiments, the enteric elastomer has difference in average length after deformation versus before deformation (e.g., stretching) of less than about 10%, less than about 5%, less than about 2%, or less than about 1%. For example, in some embodiments, the enteric elastomer is capable of exhibiting reversible elongation when stretched from at least about 50%, at least about 100%, at least about 200%, at least about 400%, at least about 500%, at least about 1000%, at least about 1200%, or at least about 1400% of its initial length. In certain embodiment, the enteric elastomer is capable of exhibiting reversible elongation when stretched from less than or equal to about 1500%, less than or equal to about 1400%, less than or equal to about 1200%, less than or equal to about 1000%, less than or equal to about 500%, less than or equal to about 400%, less than or equal to about 200%, or less than or equal to about 100% of its initial length. Any and all closed ranges that have endpoints within any of the above referenced ranges are also possible (e.g., between about 50% and about 1500%, between about hundred percent and about 1500%, between about 200% and about 1000%, between about 500% and about 1400%). Other ranges are also possible.

In certain embodiments, the enteric elastomer has an elastic modulus ranging between about 0.1 MPa and about 100 MPa. In some embodiments, the elastic modulus of the enteric elastomer is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 25 MPa, or at least about 50 MPa. In certain embodiments, the elastic modulus of the enteric elastomer is less than or equal to about 100 MPa, less than or equal to about 50 MPa, less than or equal to about 25 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Any and all closed ranges that have endpoints within any of the above referenced ranges are also possible (e.g., between about 0.1 MPa and about 100 MPa, between about 0.3 MPa and about 10 MPa). Other ranges are also possible. Those skilled in the art would be capable of selecting suitable methods for determining the elastic modulus of an enteric elastomer including, for example, tensile mechanical characterization under ASTM D638 and/or compressive mechanical characterization under ASTM D575.

In certain embodiments, the enteric elastomer comprises a polymeric mixture of varying ratios of poly(acryloyl-6-aminocaproic acid) and poly(methacrylic acid-co-ethyl acrylate).

In some embodiments, the enteric elastomer comprises a polymer of a acryloylaminoalkylene acid monomer, or salts thereof. In some embodiments, the enteric elastomer comprises a polymer of an acryloylaminoalkylene acid monomer, a (meth)acryloylaminoalkylene acid monomer, or salts thereof. In certain embodiments, the acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminononanoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononanoic acid, methacryloyl-10-aminodecanoic acid, methacryloyl-11-aminoundecanoic acid, methacryloyl-12-aminododecanoic acid, salts thereof, and combinations thereof.

In certain embodiments, the enteric elastomer comprises a homopolymer of acryloyl-6-aminocaproic acid or salts thereof. In some embodiments, the enteric elastomer comprises a copolymer of acryloyl-6-aminocaproic acid or salts thereof. In certain embodiments, enteric elastomer comprises poly(methacrylic acid-co-ethyl acrylate) or salts thereof. In some cases, the poly(methacrylic acid-co-ethyl acrylate) has a molar ratio of methacrylic acid monomer units to ethylacrylate monomer units of about 1:1.

In some embodiments, the enteric elastomer is a blend. For example, in certain embodiments, the enteric elastomer comprises a first enteric polymer (e.g., poly(acryloyl-6-aminocaproic acid)) and a second enteric polymer (e.g., poly(methacrylic acid-co-ethyl acrylate)). In some such embodiments, the weight ratio of the first polymer to the second polymer ranges from about 1:6 to about 6:1. In certain embodiments, the weight ratio of the first polymer to the second polymer is at least about 1:6, at least about 1:5, at least about 1:4, at least about 1:3, at least about 1:2, at least about 1:1, at least about 2:1, at least about 3:1, at least about 4:1, or at least about 5:1. In some embodiments, the weight ratio of the first polymer to the second polymer is less than or equal to about 6:1, less than or equal to about 5:1, less than or equal to about 4:1, 3:1, less than or equal to about 2:1, less than or equal to about 1:1, less than or equal to about 1:2, less than or equal to about 1:3, less than or equal to about 1:4, or less than or equal to about 1:5. Combinations of the above referenced ranges are also possible (e.g., between about 1:6 and about 6:1, between about 1:4 and about 4:1, between about 1:3 and about 3:1, between about 1:2 and about 2:1, between about 1:3 and about 1:1, between about 1:1 and about 3:1). Other ranges are also possible.

In some embodiments, the enteric elastomer is a polymer gel with water content no greater than 40%. For example, in some embodiments, the enteric elastomer has a water content of less than or equal to about 40 wt %, less than or equal to about 30 wt %, less than or equal to about 20 wt %, or less than or equal to about 10 wt %. In some embodiments, the enteric elastomer has a water content greater than about 5 wt %, greater than about 10 wt %, greater than about 20 wt %, or greater than about 30 wt %. Combinations of the above-referenced ranges are also possible (e.g., between about 5 wt % and about 40 wt %).

The enteric elastomer can be used as a material platform. In some embodiments, this material platform features tunable elastomeric properties, is stable in an acidic environment, and/or dissolvable in a more alkali environment. Thus, the enteric elastomer material platform is compatible with the acidic gastric environment and has the capacity for targeted dissolution in the small intestinal/colonic environment. According to some embodiments, the enteric elastomer material platform is useful for many applications, including, but not limited to, gastrointestinal structure manufacturing, and gastrointestinal-specific drug delivery with targeted release beyond the pylorus.

For example, one or more enteric elastomer linkers attached to and/or incorporated into a structure in a gastric cavity can mitigate the risk of accidental passage of the macrostructure, which could induce obstruction and/or penetration, because the rapid dissolution of the one or more linkers upon passage through the pylorus would reduce the macrostructure to smaller, previously-linked portions.

A structure bonded with an enteric elastomer can be subject to dissolution in the presence of an alkali environment. Thus, in the case of a gastric structure resident in vivo and comprising an enteric elastomer, passage of the structure can be induced if the subject ingests an alkali solution (e.g., sodium bicarbonate) to induce the dissolution of the enteric elastomer to enable breakdown of the structure in accordance with some embodiments.

In some embodiments, the enteric elastomer linker has substantial flexibility. Flexibility can enable packing and/or folding of a structure to, for example, fit into a confined/predefined vessel such as capsule for oral administration or a catheter for endoscopic deployment, as described herein. In some embodiments, the enteric elastomer has flexibility to 180 degrees to enable tight and/or maximal packing and/or folding (e.g., for use as an elastic polymeric component, as described above).

In some embodiments, the structure (e.g., comprising one or more polymeric components) comprises one or more configurations. For example, in certain embodiments, the structure has a particular configuration such as a defined shape, size, orientation, and/or volume. The structure may comprise any suitable configuration. In some embodiments, the structure has a particular shape as defined by a cross-sectional area of the structure. Non-limiting examples of suitable cross-sectional shapes include square, circles, ovals, polygons (e.g., pentagons, hexagons, heptagons, octagons, nonagons, dodecagons, or the like), tubes, rings, star or star-like/stellate (e.g, 3-armed stars, 4-armed stars, 5-armed stars, 6-armed stars, 7-armed stars, 8-armed stars), or the like. Those skilled in the art would be capable of selecting suitable shapes depending on the application (e.g., a stellate shape for gastric retention structures) and based upon the teachings of this specification.

The structure may, in some cases, have an original configuration which may be modified (e.g., deformed) such that the structure obtains a new configuration, different than the original configuration. For example, in some embodiments, the structure has a first configuration and a second configuration, different than the first configuration, e.g., when compressed.

In certain embodiments, the configuration of the structure may be characterized by a largest cross-sectional dimension. In some embodiments, the largest cross-sectional dimension of the first configuration may be at least about 10% less, at least about 20% less, at least about 40% less, at least about 60% less, or at least about 80% less than the largest cross-sectional dimension of the second configuration. In certain embodiments, the largest cross-sectional dimension of the second configuration may be at least about 10% less, at least about 20% less, at least about 40% less, at least about 60% less, or at least about 80% less than the largest cross-sectional dimension of the first configuration. Any and all closed ranges that have endpoints within any of the above referenced ranges are also possible (e.g., between about 10% and about 80%, between about 10% and about 40%, between about 20% and about 60%, between about 40% and about 80%). Other ranges are also possible.

Figure 1D:
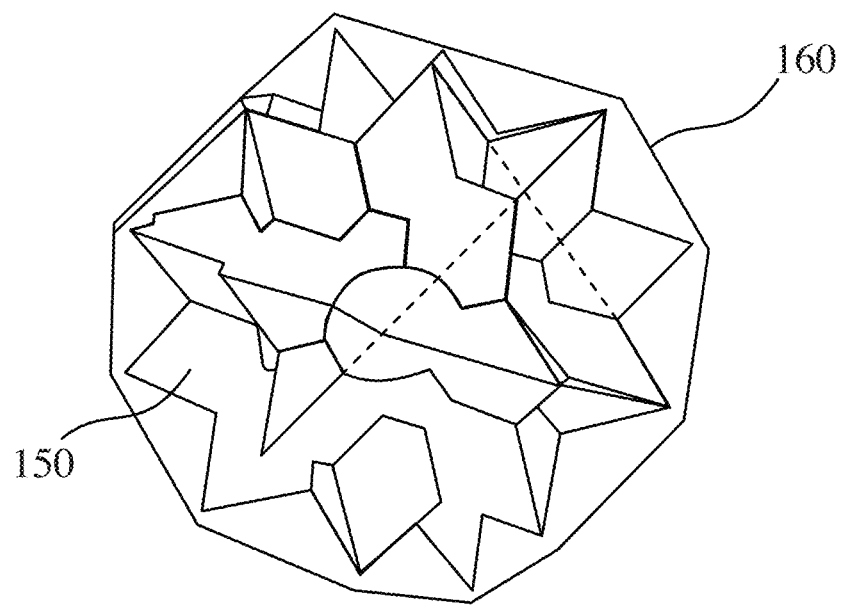
FIG. 1D is a schematic diagram illustrating the convex hull volume of a structure, according to one set of embodiments.

In some embodiments, the configuration of the structure may be characterized by a convex hull volume of the structure. The term convex hull volume is known in the art and generally refers to a set of surfaces defined by the periphery of a 3-D object such that the surfaces define a particular volume. For example, as illustrated in FIG. 1D, a 3D star-like object 150 has a convex hull volume as defined by convex hull 160. In some embodiments, the convex hull volume of the first configuration may be at least about 10% less, at least about 20% less, at least about 40% less, at least about 60% less, or at least about 80% less than the convex hull volume of the second configuration. In certain embodiments, the convex hull volume of the second configuration may be at least about 10% less, at least about 20% less, at least about 40% less, at least about 60% less, or at least about 80% less than the convex hull volume of the first configuration. Any and all closed ranges that have endpoints within any of the above referenced ranges are also possible (e.g., between about 10% and about 80%, between about 10% and about 40%, between about 20% and about 60%, between about 40% and about 80%). Other ranges are also possible.

Those skilled in the art would understand that the differences between the first configuration and the second configuration do not refer to a swelling or a shrinking of the structure (e.g., in the presence of a solvent), but instead refers to a change in shape and/or orientation of at least a portion of the structure (e.g., in the presence of a stimulus such as heat and/or mechanical pressure/compression), although some degree of swelling or shrinking may occur between the two configurations.

In some embodiments, the first configuration is constructed and arranged such that a structure is retained at a location internal of a subject, and the second configuration is constructed and arranged such that the structure may be encapsulated (e.g., for oral delivery of the structure within a capsule). In some cases, the first configuration is sufficiently large such that the structure is retained at a location internal of the subject and the second configuration is sufficiently small such that the structure may fit within a particular size capsule suitable for oral delivery to a subject.

In certain embodiments, the structure may be polymerized and/or cast in a first configuration, mechanically deformed such that the structure obtains a second configuration, and placed in a capsule or restrained by some other containment structure. The structure may be mechanically deformed using any suitable method including, for example, bending, twisting, folding, molding (e.g., pressing the material into a mold having a new shape), expanding (e.g., applying a tensile force to the material), compressing, and/or wrinkling the structure. The structure may maintain the second configuration for any suitable duration prior to stimulation/release. Advantageously, certain embodiments of the structures described herein may be relatively stable in the first and/or second configurations such that the structure may be stored for long periods of time without significant degradation of mechanical properties of the one or more components and/or one or more linkers. In some embodiments, the structure may be stable under ambient conditions (e.g., room temperature, atmospheric pressure and relative humidity) and/or physiological conditions (e.g., at or about 37° C., in physiologic fluids) for at least about 1 day, at least about 3 days, at least about 7 days, at least about 2 weeks, at least about 1 month, at least about 2 months, at least about 6 months, at least about 1 year, or at least about 2 years. In certain embodiments, the structure has a shelf life of less than or equal to about 3 years, less than or equal to about 2 years, less than or equal to about 1 year, less than or equal to about 1 month, less than or equal to about 1 week, or less than or equal to about 3 days. Any and all closed ranges that have endpoints within any of the above-referenced ranged are also possible (e.g., between about 24 hours and about 3 years, between about 1 week and 1 year, between about 1 year and 3 years). Other ranges are also possible.

In some embodiments, the structure in the second configuration may recoil such that the structure reverts to the first configuration. For example, in some embodiments, the structure in the second configuration is contained within a capsule and delivered orally to a subject. In some such embodiments, the structure may travel to the stomach and the capsule may release the structure from the capsule, upon which the structure obtains (e.g., recoils to) the first configuration.

As described herein, in some embodiments, the structure may comprise one or more linkers and/or one or more components with particular mechanical properties (e.g., elastic polymeric components) such that the structure will substantially recoil after being mechanically deformed. The structure may be characterized, in some cases, by a folding force. The term folding force generally refers to the force required to compress the structure into a cavity having a cross-sectional area of less than about 2 cm (e.g., such as the pylorus). In some embodiments, the folding force of the structure is at least about 0.2 N, at least about 0.5 N, at least about 0.7 N, at least about 1 N, at least about 1.5 N, at least about 2 N, at least about 2.5 N, or at least about 3 N. In certain embodiments, the folding force of the structure is less than or equal to about 5 N, less than or equal to about 3 N, less than or equal to about 2.5 N, less than or equal to about 2 N, less than or equal to about 1.5 N, less than or equal to about 1 N, less than or equal to about 0.7 N, or less than or equal to about 0.5 N. Any and all closed ranges that have endpoints within any of the above-referenced ranges are also possible (e.g., between about 0.2 N and about 3 N, between about 0.2 N and about 2.5 N, between about 0.5 N and about 1.5N, between about 1 N and about 3 N). Other ranges are also possible. The folding force may be determined by, for example, by placing the structure in a funnel (shown in FIG. 13A) having a 20 cm upper diameter and a 2 cm lower diameter (e.g., simulating the pyloric sphincter) and measuring the forces required to move the structure through the 2 cm lower diameter. A plunger may be attached to the tension cross-head of an tensile loading machine and the funnel to a clamp, and the structure pushed through the funnel at a rate of, for example, 10 mm/min, which measuring the force and displacement. The folding force is generally determined by measuring the force at which the structure folds and enters the 2 cm lower diameter tube.

In certain embodiments, the structure in the first configuration has an uncompressed cross-sectional dimension. The uncompressed cross-sectional dimension is generally selected such that the structure is retained at a location internally to a subject for a relatively long period of time (e.g., at least about 24 hours) even under physiological compressive forces (e.g., such as those in the digestive tract).

In some embodiments, the uncompressed cross-sectional dimension of the first configuration is at least about 2 cm, at least about 4 cm, at least about 5 cm, or at least about 10 cm. In certain embodiments, the uncompressed cross-sectional dimension of the first configuration is less than or equal to about 15 cm, less than or equal to about 10 cm, less than or equal to about 5 cm, or less than or equal to about 4 cm. Any and all closed ranges that have endpoints within any of the above-referenced ranges are also possible (e.g., between about 2 cm and about 15 cm). Those skilled in the art would be capable of selecting suitable uncompressed cross-sectional dimensions for structures based upon the teachings of this specification for specific orifices of a subject such that the structure is retained.

As described herein, in some embodiments, the one or more polymeric components of the structure may be cast, molded, and/or cut to have a particular shape, size, and/or volume. For example, in an exemplary embodiment, one or more elastic polymeric components, one or more loadable polymeric components, and/or one or more linkers are polymerized independently into sheets and cut into desired shapes and/or sizes. The cut components and linkers may then be assembled (e.g., in a mold) and treated such that the one or more components and linkers are coupled. In certain embodiments, one or more elastic polymeric components, one or more loadable polymeric components, and/or one or more linkers are polymerized independently in molds of desired shapes. In some embodiments, the one or more components and/or linkers are adhered via an adhesive. In certain embodiments, the one or more components and/or linkers are heated such that the one or more components and/or linkers are coupled (e.g., via bonding and/or entanglement), as described herein.

In an exemplary embodiment, a shape configured for residence such as gastric residence comprises a three-dimensional elliptical ring structure (i.e., an elliptical outline when projected onto a flat surface). In some embodiments, the elliptical ring structure has a minor axis diameter comparable to the major axis of a capsule. In some embodiments, the elliptical ring structure comprises a loadable polymeric component and one or more linkers configured to degrade in a controlled manner attached to and/or incorporated into the elliptical ring structure. In some embodiments, one or more linkers are incorporated into the elliptical ring structure at one or more points along the minor axis. In further embodiments, one or more controlled degradation linkers are incorporated into the elliptical ring structure at one or more points along the major axis. According to some embodiments, the elliptical ring structure may be twisted into a form similar to a double helix for packing into a soluble container and/or binding with a retention element. In some embodiments, the elliptical ring structure is twisted such that the axis of the helix is along the minor axis of the elliptical ring structure to avoid bending the helix to pack it into a soluble container.

In some embodiments, a shape configured for residence (e.g., being retained in an orifice at a particular location internal to a subject) such as gastric residence comprises a three-dimensional structure having a plurality of projections (i.e. arms). In some embodiments, the structure with projections comprises a flexible material configured for elastic (non-plastic) deformation. The projections themselves may be flexible or rigid with flexible connections to a core. In some embodiments, one or more controlled degradation linkers (e.g., enteric elastomers) are attached to and/or incorporated into the structure, for example, along one or more projections, such as near or at the connection to a core. In some embodiments, each projection has a length equal to just less than the length of a soluble container such that the unencapsulated final form has a diameter equal to nearly twice the soluble container length. In some embodiments, the projections each may have a length of about 0.5 cm to about 2.5 cm (e.g., such that the structure has an uncompressed cross-sectional dimension of at least about 2 cm).

In certain embodiments, the projections are arranged based on bio-inspired flower bud designs in which a number (N) of radial spokes or petals project from a central linking core. In some embodiments, these radial projections each have an internal sector angle of approximately 360°/N, where N is the total number of radial projections. In some cases, this enhances the packing volume of the encapsulated structure, thus increasing drug carrying capacity. In some embodiments, the projections are formed of a material with a relatively high elastic modulus to increase the resistance to compression and duration of gastric residence, as described herein.

Figure 1E:
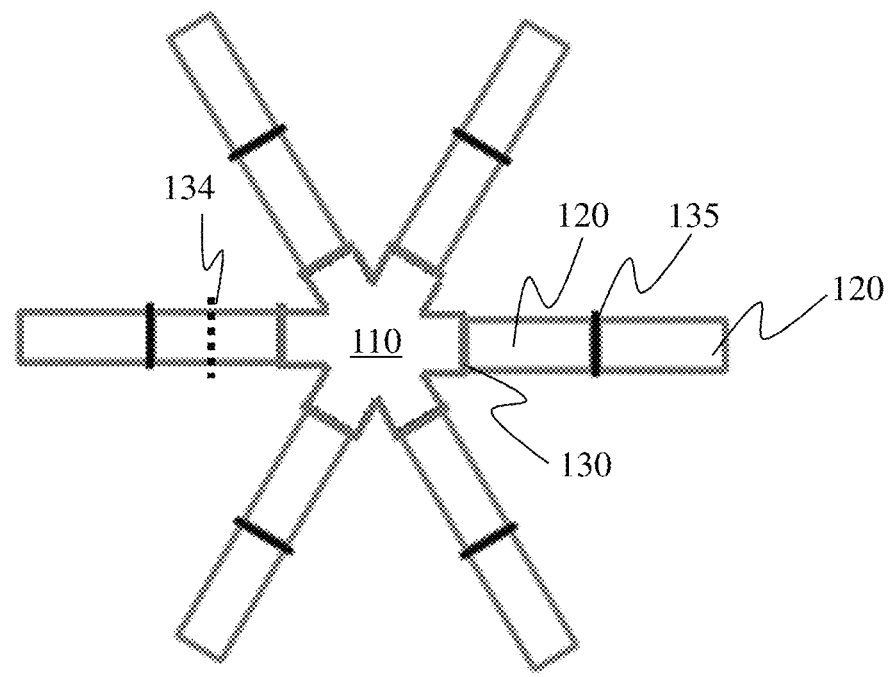
FIGS. 1E-1F are schematic diagrams of exemplary configurations of a residence structure, according to one set of embodiments.

In some embodiments, the one or more linkers are attached to and/or incorporated into the structure. For example, as illustrated in FIG. 1E, structure 102 comprises a first configuration comprising a 6-armed star-like shape. While a 6-armed star-like shape is shown here, those skilled in the art would understand that FIG. 1E is meant to be non-limiting and that the structure could have 3, 4, 5, 6, 7, 8, 9, 10, or more arms, as described herein, and each could vary in length, number of components, and/or linkers.

Structure 102 comprises elastic polymeric component 110 coupled with loadable polymeric components 120. For example, loadable polymeric component 120 may be coupled with elastic polymeric component 110 via optional first linkers 130. In certain embodiments, elastic polymeric component 110 comprises an enteric elastomer. Additional loadable polymeric components 120 may be coupled together via optional second linker 135, different than optional linker 130. The number and/or location of linkers may be chosen as part of certain design parameters (e.g., such that the structure has certain degradation properties and/or configurations). The location of the linkers may also vary. For example, as shown by optional linker 134 (dashed), the linkers may be embedded within one or more loadable polymeric components 120.

Figure 1F:
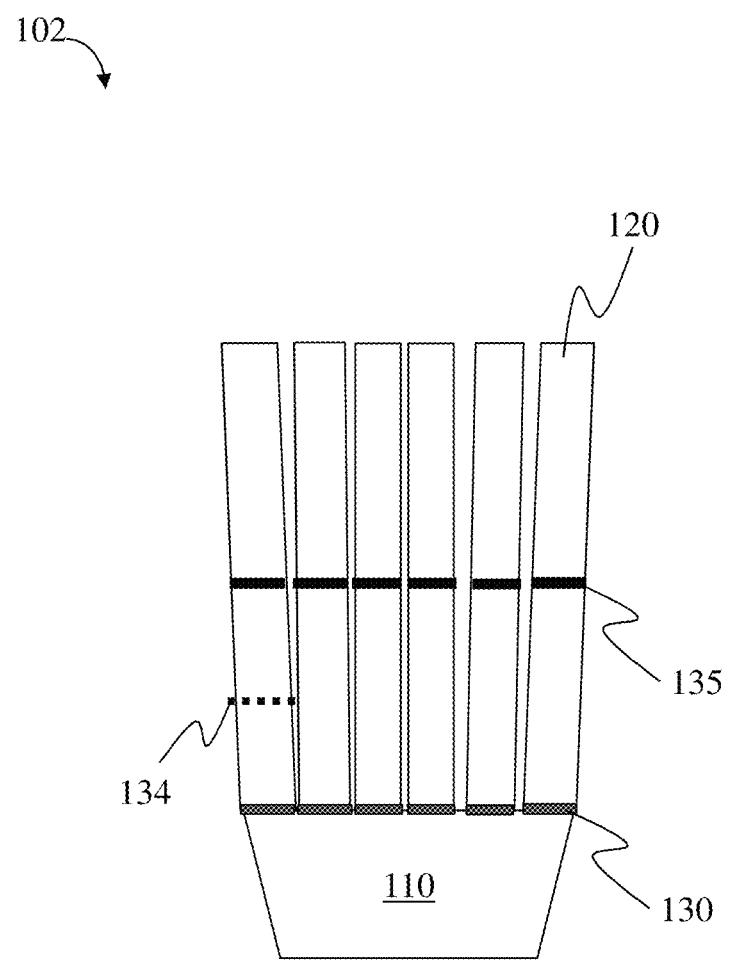

Structure 102 may be folded into a second configuration, as illustrated in FIG. 1F, such that the structure may be encapsulated. Those skilled in the art would understand that FIG. 1F is meant to be non-limiting, and the structure shown in FIG. 1E could be folded into additional configurations.

According to some embodiments, a shape configured for residence (e.g., being retained in an orifice at a particular location internal to a subject) such as a gastric residence comprises a three-dimensional structure forming a polygon outline with, for example, 3, 4, 6, 8, 10, 12, 14, 16, 18, or 20 sides, when projected onto a flat surface. In some embodiments, each side has a length equal to just less than the length of a soluble container. In some embodiments, the structure comprises a flexible material configured for elastic (non-plastic) deformation such that the structure is configured for bending at its vertices and packing into a soluble container. Materials with low elastic moduli, with low creep deformation and/or good recoil, and configured for large elastic deformation may be used at the vertices to facilitate stable packing. In some embodiments, individual sides each have an internal sector angle of approximately 360°/N, where N is the total number of sides, to obtain maximal packing.

In some embodiments, one or more linkers are attached to and/or incorporated into the structure. In certain embodiments, a flexible linker configured for high degree of elastic deformation and controlled degradation (e.g., comprising an enteric elastomer) is located at each of the vertices between the sides of the polygon.

Figure 1G:
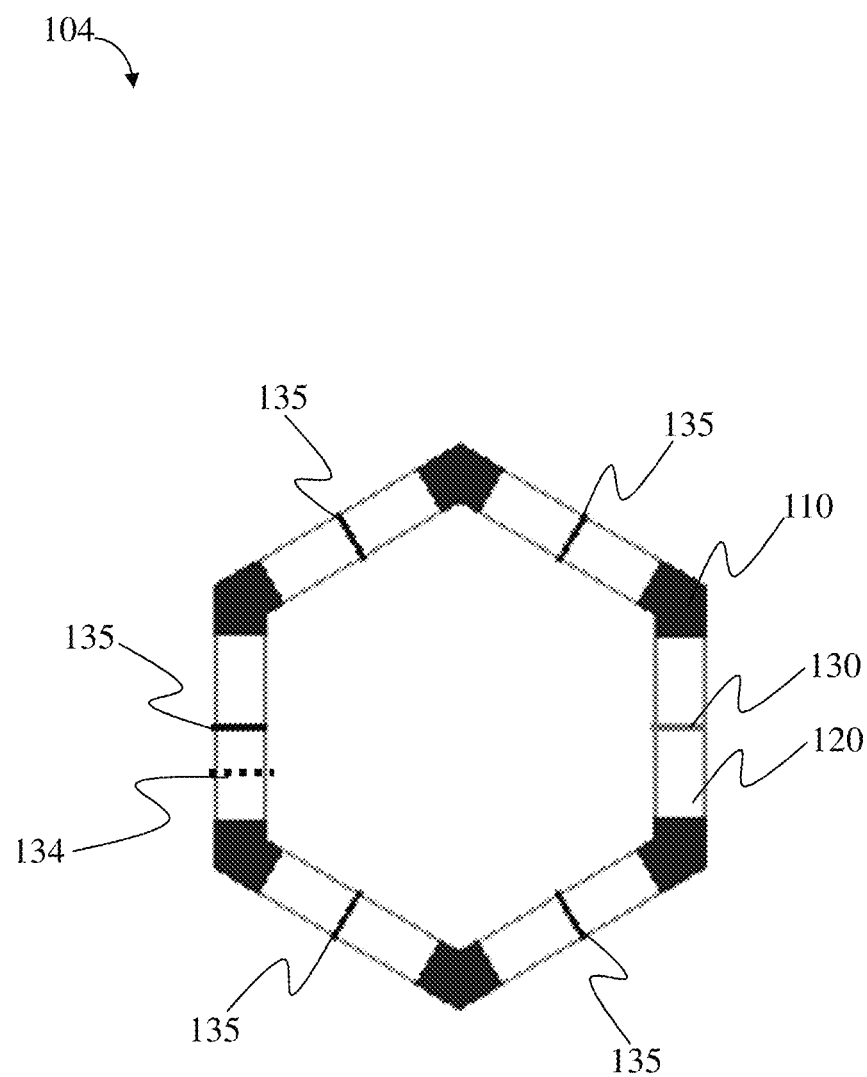
FIGS. 1G-1H are schematic diagrams of other exemplary configurations of a residence structure, according to one set of embodiments.

For example, as illustrated in FIG. 1G, structure 104 comprises a first configuration comprising a hexagon. While a hexagonal shape is shown here, those skilled in the art would understand that FIG. 1G is meant to be non-limiting and that the structure could have 4, 6, 8, 10, 12, or more sides, as described herein, and each could vary in length, number of components, and/or linkers.

Structure 104 comprises elastic polymeric component 110 coupled with loadable polymeric components 120. For example, elastic polymeric component 110 and loadable polymeric component 120 may be coupled with elastic polymeric component 110 via optional linkers 130 or 135, different than optional linker 130. In some embodiments, elastic polymeric component 110 comprises an enteric elastomer. The number and/or location of linkers may be chosen as part of certain design parameters (e.g., such that the structure has certain degradation properties and/or configurations). The location of the linkers may also vary. For example, as shown by optional linker 134 (dashed), the linkers may be embedded within one or more loadable polymeric components 120.

Figure 1H:
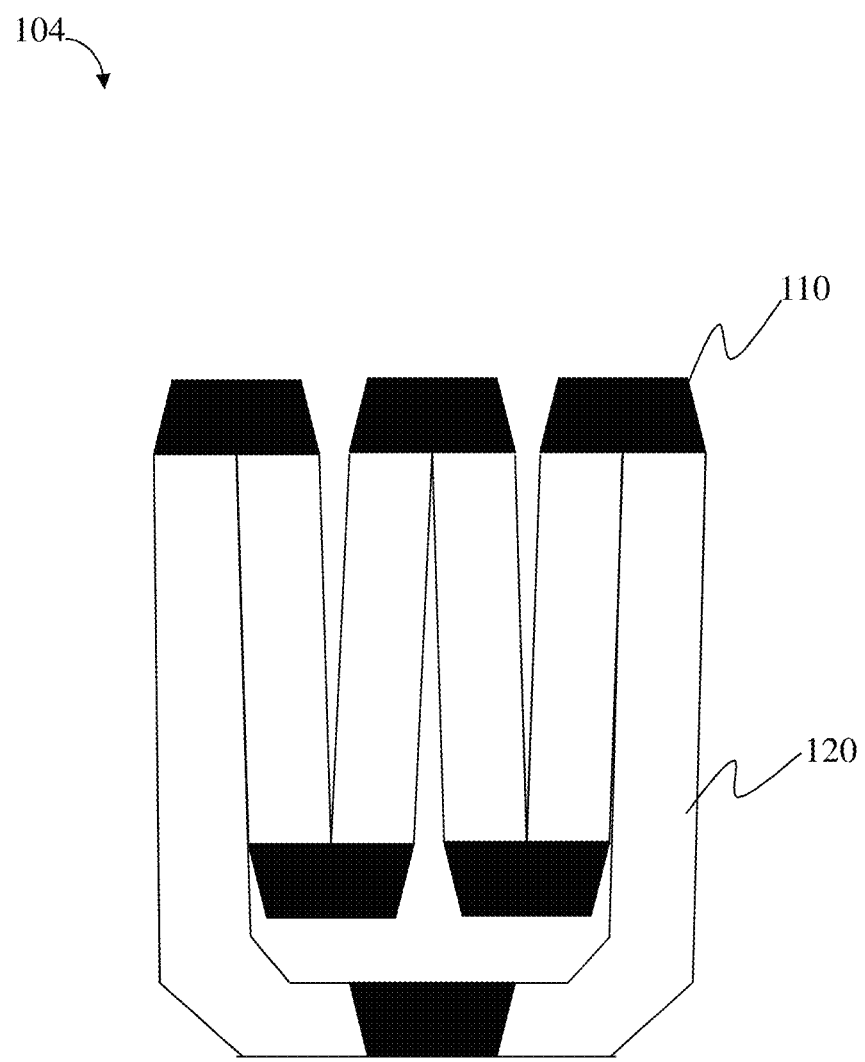

Structure 104 may be folded into a second configuration, as illustrated in FIG. 1H, for encapsulation. Those skilled in the art would understand that FIG. 1H is meant to be non-limiting, and the structure shown in FIG. 1G could be folded into additional configurations.

In an exemplary embodiment, the linkers coupling the elastic polymeric component and the loadable polymeric component (optional linker 130) may be time-dependent degradable linkers (e.g., such that the arms of the structure detach after a particular length of time). In certain embodiments, the linkers coupling and/or embedded within the loadable polymer components together (optional linkers 135 and 134) may comprise enteric polymers, such that the loadable polymer components decouple when exposed to pH greater than about 5. For example, the structures illustrated in FIGS. 1E-1H may be delivered (e.g., orally administered) to a subject via a capsule (containing the structure in the second configuration) and released (obtaining the first configuration), and retained, at a location internal to the subject such as the stomach before the pylorus. After a particular length of time (e.g., the residence time period such as at least about 24 hours), the time-dependent degradable linker may degrade and the structure separates into several units, which pass through the pylorus. Upon entry into the intestines (e.g., at pH greater than about 5), the linkers comprising an enteric polymer degrade and the arms further separate into smaller, more easily removed, units.

In some cases, the active substance may be loaded into beads and/or particles comprising the loadable polymeric material embedded within an elastic polymer such as an elastic degradable linker (e.g., comprising an enteric elastomer). In some embodiments, the loadable polymeric component comprises beads and/or particles dispersed/embedded within one or more elastic polymer components and/or one or more linkers. For example, in certain embodiments, the loadable polymeric component beads/particles may be coupled with the elastic polymer component and/or additional loadable polymeric component beads/particles via a linker (e.g., where the linker is physically attached the loadable polymeric component or at least partially encapsulates the loadable polymeric component).

Figure 2:
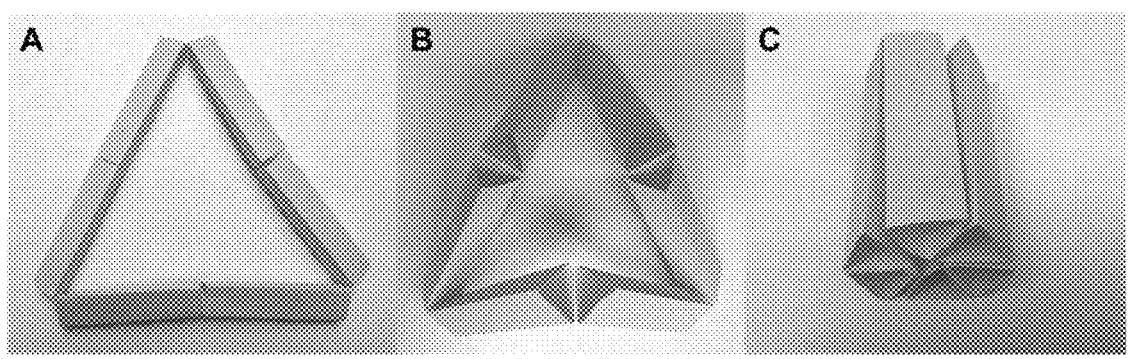
FIG. 2 is a reproduction of a photograph of an exemplary residence structure and a strategy for folding the structure, according to one set of embodiments.
Figure 3A:
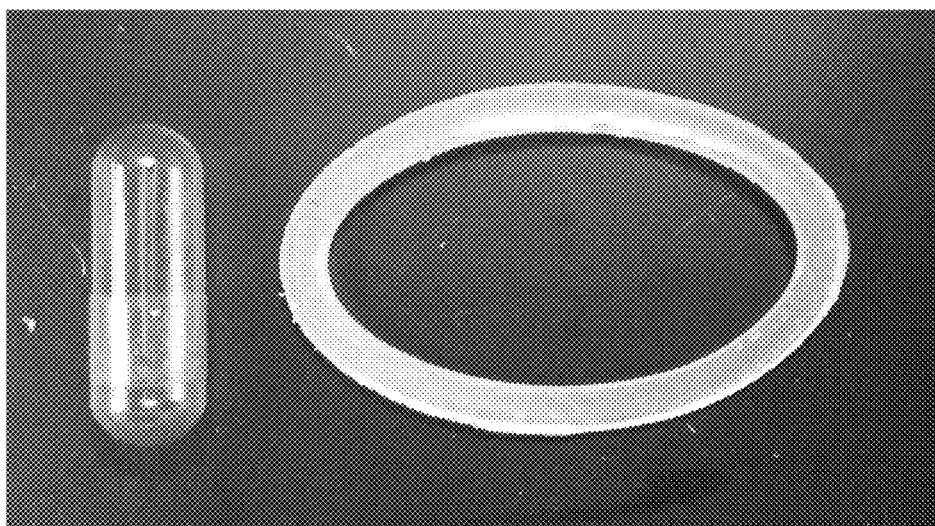
FIGS. 3A-3E are reproductions of photographs of an exemplary residence system and structure, showing (A) an exemplary structure and an encapsulating structure; (B) the exemplary structure folded within the encapsulating structure; (C) another view of an exemplary structure; (D) the exemplary structure twisted; and (E) the exemplary structure of (D) twisted within the encapsulating structure, according to one set of embodiments.
Figure 3B:
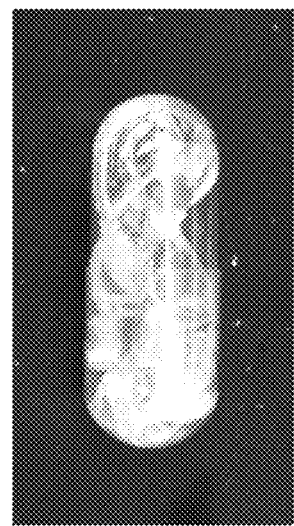
Figure 3C:
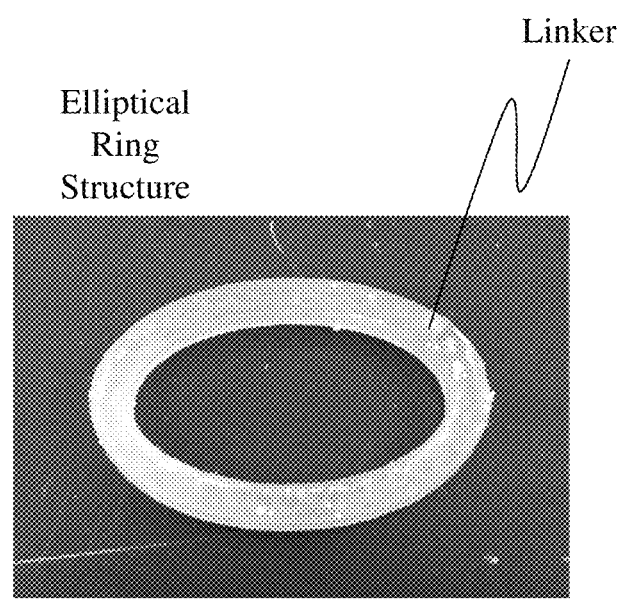
Figure 3D:
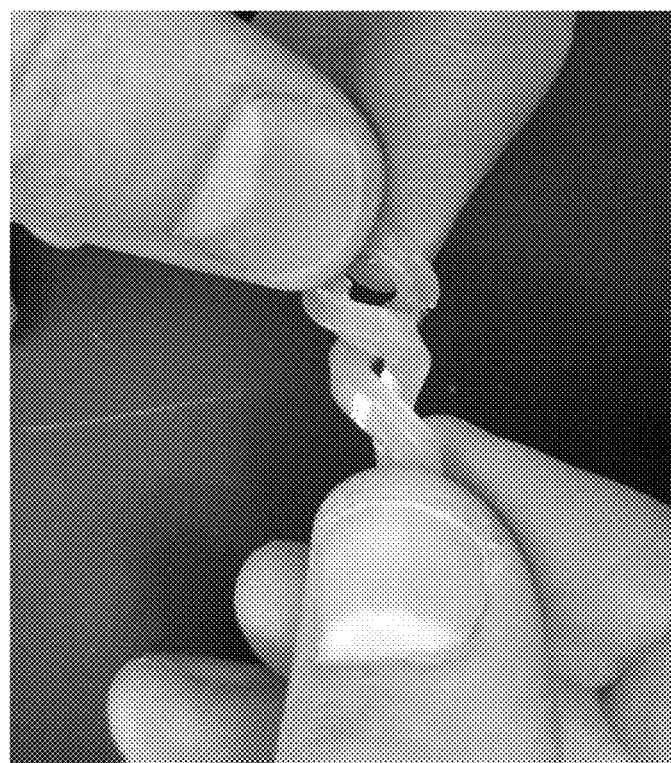
Figure 3E:

Various packing/folding strategies can be used to minimize the size of a structure for encapsulation and/or maximize the size of a structure for gastric residence in accordance with some embodiments. In some embodiments, a polygonal structure with a triangular cross-section forms a triangle when projected onto a plane as shown in FIG. 2. According to this embodiment, each side of the three sides of the triangle is configured to fold in half at a hinge which results in high packing density with six total sides once folded.

Typical residence structures known in the art such as intragastric balloons generally result in at least partial gastric outlet obstruction in subjects. Advantageously, in some embodiments, the structure comprises a shape with sufficient void space (or fenestrations) to allow the passage of food material including indigestible substances thereby avoiding partial or complete gastric outlet obstruction, when located in or at an orifice internally of the subject.

In some embodiments, the structure is fenestrated. In an exemplary embodiment, referring again to FIG. 1G, the structure has a polygonal cross-sectional area defined by an external surface of the structure. In some such embodiments, the structure comprising one or more polymeric components and linkers has an internal cross-sectional area that comprises one or more voids (i.e. does not comprise one or more polymeric components and linkers), such that food and other substances may pass through the structure.

In another exemplary embodiment, referring again to FIG. 1E, the structure has a star-like configuration such that food and other substances may pass between the arms of the structure (e.g., when resident in a location internally of a subject).

As described above, in some embodiments, the initial (undeformed) configuration of the structure may be characterized by a convex hull volume. In some embodiments, the structure comprising one or more polymeric components and linkers (i.e. the solid components of the structure as opposed to void space) occupies between about 10 vol % and about 90 vol % of the total convex hull volume of the initial configuration. For example, in certain embodiments, the structure occupies less than or equal to about 90 vol %, less than or equal to about 80 vol %, less than or equal to about 70 vol %, less than or equal to about 60 vol %, less than or equal to about 50 vol %, less than or equal to about 40 vol %, less than or equal to about 30 vol %, or less than or equal to about 20 vol % of the convex hull volume of the initial configuration. In some embodiments, the structure occupies at least about 10 vol %, at least about 20 vol %, at least about 30 vol %, at least about 40 vol %, at least about 50 vol %, at least about 60 vol %, at least about 70 vol %, or at least about 80 vol % of the convex hull volume of the initial configuration. Any and all closed ranges that have endpoints within any of the above referenced ranges are also possible (e.g., between about 10 vol % and about 90 vol %, between about 30 vol % and about 90 vol %, between about 20 vol % and about 50 vol %, between about 40 vol % and about 60 vol %, between about 40 vol % and about 90 vol %). Other ranges are also possible.

As described herein, in some embodiments, the structure is configured to adopt a shape and/or size compatible with oral administration to and/or ingestion by a subject. In some embodiments, the structure has a shape with a capacity for folding and/or packing into stable encapsulated forms. For example, in some embodiments the structure is designed to maximally pack and fill a capsule or other soluble container (e.g., a containing structure). In some embodiments, the structure has a shape that maximally fills and/or packs into a capsule or other soluble container.

In some embodiments, the system comprises the structure and a containing structure. In some embodiments, the structure comprises more than 60 vol % of the containing structure. Based on the application, a capsule may be manufactured to particular specifications or a standard size, including, but not limited to, a 000, 00, 0, 1, 2, 3, 4, and 5, as well as larger veterinary capsules Su07, 7, 10, 12e1, 11, 12, 13, 110 ml, 90 ml, and 36 ml. In some embodiments, the structure may be provided in capsules, coated or not. The capsule material may be either hard or soft, and as will be appreciated by those skilled in the art, typically comprises a tasteless, easily administered and water soluble compound such as gelatin, starch or a cellulosic material.

In other embodiments, the structure is retained in a packed shape by a soluble retaining element, such as a band or surgical thread. In some embodiments, the structure comprises optimal combinations of materials with high and low elastic moduli, giving the structure the capacity to alter its shape and/or size once the soluble container and/or soluble retaining element is removed.

For example, consider a human patient with hypothyroidism, who is prescribed levothyroxine with the dosing level held stable at 125 μg per day for six months (e.g., between checks of thyroid-stimulating hormone). During those six months, the patient should undergo 168 drug administration events, each event involving an administration dose of 125 μg. According to some embodiments, a structure configured for controllable gastric residence is loaded with in excess of 21 mg of levothyroxine (i.e., 125 μg per day for 168 days), and configured to release about 125 μg per day. Thus, the patient undergoes one drug administration versus 168 drug administration events over the same time period with comparable efficacy.

Similarly, consider a human patient infected with hepatitis B, treated with daily doses of entecavir. According to some embodiments, a structure configured for controllable gastric residence is loaded with about 84 mg of entecavir (i.e., 0.5 mg per day for 168 days) so that the patient undergoes one drug administration versus 168 drug administration events over the same time period with the same results. In another case, consider a human patient with at least one of Barrett's esophagus, a gastric ulcer, and gastroesophageal reflux disease, treated with omeprazole. According to some embodiments, a structure configured for controllable gastric residence is loaded with about 3,360 mg of omeprazole (i.e., 20 mg per day for 168 days) so that the patient undergoes one drug administration versus 168 drug administration events over the same time period with comparable efficacy.

In another example, consider a human patient with an exacerbation or flare of at least one of chronic obstructive pulmonary disease, ulcerative colitis, asthma, and gout. The patient, is prescribed prednisone with an initial daily dosing level held stable for two weeks then tapered off over an additional number of days, for example, 23 or more total days of prednisone treatment. During treatment, the patient should undergo 23 drug administration events, each event involving one of at least two predetermined administration doses. According to some embodiments, a structure configured for controllable gastric residence is loaded with about 770 mg of prednisone and configured to release a first predetermined administration dose each day for two weeks followed by lower predetermined administration doses on the days after. Thus, the patient undergoes one drug administration versus 23 or more drug administration events over the same time period with the same results. Further, the patient will not have to be vigilant as to the dose change(s) because the structure is preconfigured to automatically taper the dosage.

In another case, consider a human patient with coronary artery disease undergoing dual antiplatelet therapy. The patient, is prescribed either clopidogrel or prasugrel with a daily dosing level held stable for at least three months. During treatment, the patient should undergo about 90 drug administration events. According to some embodiments, a structure configured for controllable gastric residence is loaded with about 6,750 mg of clopidogrel (i.e., 75 mg per day for 90 days) or 900 mg of prasugrel (i.e., 10 mg per day for 90 days) so that the patient undergoes one drug administration versus 90 drug administration events over the same time period with comparable efficacy. In another example, consider a human patient with at least one of hyperlipidemia and coronary artery disease, treated with rosuvastatin. According to some embodiments, a structure configured for controllable gastric residence is loaded with about 1,800 mg of rosuvastatin (i.e., 10 mg per day for 180 days) so that the patient undergoes one drug administration versus 180 drug administration events over the same time period with comparable efficacy.

Any terms as used herein related to shape, orientation, alignment, and/or geometric relationship of or between, for example, one or more articles, compositions, structures, materials and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

The term "subject," as used herein, refers to an individual organism such as a human or an animal. In some embodiments, the subject is a mammal (e.g., a human, a non-human primate, or a non-human mammal), a vertebrate, a laboratory animal, a domesticated animal, an agricultural animal, or a companion animal. In some embodiments, the subject is a human. In some embodiments, the subject is a rodent, a mouse, a rat, a hamster, a rabbit, a dog, a cat, a cow, a goat, a sheep, or a pig.

The term "electrophile," as used herein, refers to a functionality which is attracted to an electron and which participates in a chemical reaction by accepting an electron pair in order to bond to a nucleophile.

The term "nucleophile" as used herein, refers to a functionality which donates an electron pair to an electrophile in order to bond to a electrophile.

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s). A "stable, isolable compound" refers to isolated reaction products and does not refer to unstable intermediates or transition states.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. In one embodiment, the alkyl group is a C1-C8 alkyl. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. In one embodiment, the alkenyl group is a C2-C8 alkenyl group and in one embodiment the alkynyl group is a C2-C8 alkynyl group. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. In one embodiment, the aryl group is a C6-C10 aryl group. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R''') wherein R', R", and R''' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

As used herein, the term "network" refers to a three dimensional substance having oligomeric or polymeric strands interconnected to one another by crosslinks.

As used herein, the term "strand" refers to an oligomeric or polymeric chain of one monomer unit, or an oligomeric or polymeric chain of two or more different monomer units.

As used herein, the term "backbone" refers to the atoms and bonds through which the monomer units are bound together. As used herein, the term "prepolymer" refers to oligomeric or polymeric strands which have not undergone crosslinking to form a network.

As used herein, the term "crosslink" refers to a connection between two strands. The crosslink may either be a chemical bond, a single atom, or multiple atoms. The crosslink may be formed by reaction of a pendant group in one strand with the backbone of a different strand, or by reaction of one pendant group with another pendant group. Crosslinks may exist between separate strand molecules, and may also exist between different points of the same strand.

As used herein, the term "active substance" refers to a compound or mixture of compounds which causes a change in a biological substrate. Exemplary classes of active substances in the medical and biological arts include therapeutic, prophylactic and diagnostic agents. The active substance may be a small molecule drug, a vitamin, a nutrient, a biologic drug, a vaccine, a protein, an antibody or other biological macromolecule. The active substance may be a mixture of any of the above listed types of compounds.

"Immunosuppressive agent" refers to an agent that inhibits or prevents an immune response to a foreign material in a subject. Immunosuppressive agents generally act by inhibiting T-cell activation, disrupting proliferation, or suppressing inflammation.

As used herein, the terms "oligomer" and "polymers" each refer to a compound of a repeating monomeric subunit. Generally speaking, an "oligomer" contains fewer monomeric units than a "polymer." Those of skill in the art will appreciate that whether a particular compound is designated an oligomer or polymer is dependent on both the identity of the compound and the context in which it is used.

One of ordinary skill will appreciate that many oligomeric and polymeric compounds are composed of a plurality of compounds having differing numbers of monomers. Such mixtures are often designated by the average molecular weight of the oligomeric or polymeric compounds in the mixture. As used herein, the use of the singular "compound" in reference to an oligomeric or polymeric compound includes such mixtures.

As used herein, reference to any oligomeric or polymeric material without further modifiers includes said oligomeric or polymeric material having any average molecular weight. For instance, the terms "polyethylene glycol" and "polypropylene glycol," when used without further modifiers, includes polyethylene glycols and polypropylene glycols of any average molecular weight.

As used herein, the term "Michael acceptor" refers to a functional group having a carbon-carbon double or triple bond in which at least one of the carbon atoms is further bonded to a carbonyl group or carbonyl analogs such as imine, oxime, and thiocarbonyl. The reaction between a Michael acceptor and nucleophile results in the formation of a covalent bond between the nucleophile and the carbon atom not directly connected to the carbonyl group or carbonyl analog. The reaction between a Michael acceptor and a nucleophile may be called a "Michael addition."

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group. In one embodiment, alkyl groups are C1-C8 alkyl groups. In one embodiment, alkenyl groups are C2-C8 alkenyl groups. In one embodiment, alkynyl groups are C2-C8 alkynyl groups.

The term "alkoxy" refers to an alkyl group, as defined above, having an oxygen atom attached thereto. In one embodiment, alkoxy groups are —O C1 C8 alkyl groups. Representative alkoxy groups include methoxy, ethoxy, propyloxy, and tert-butoxy. An "ether" is two hydrocarbons covalently linked by an oxygen.

The term "alkylthio" refers to an alkyl group, as defined above, having a sulfur atom attached thereto. In some embodiments, the "alkylthio" moiety is represented by one of —S-alkyl, —S-alkenyl, and —S-alkynyl. In some embodiments, the "alkylthio" moiety is represented by one of —S—C1-C8 alkyl, —S—C2-C8 alkenyl, and —S—C2-C8 alkynyl. Representative alkylthio groups include methylthio and ethylthio.

The term "amido" is art-recognized as an amino substituted by a carbonyl group.

The term "aralkyl", as used herein, refers to an alkyl group substituted with an aryl group. The term "heteroaralkyl", as used herein, refers to an alkyl group substituted with a heteroaryl group.

The term "heteroatom" as used herein means an atom of any element other than carbon or hydrogen. Examplary heteroatoms are nitrogen, oxygen, and sulfur.

As used herein, the term "thiol" means —SH; the term "hydroxyl" means —OH; and the term "sulfonyl" means —SO$_2$—.

As used herein the term "oxo" refers to a carbonyl oxygen atom.

As used herein, the term "alkaloid" refers to a naturally occurring organic compound containing at least one non-peptidic nitrogen atom.

EXAMPLES

The following examples are intended to illustrate certain embodiments of the present invention, but do not exemplify the full scope of the invention.

Example 1—Elliptical Ring Design

Polycaprolactone (PCL) was chosen as the loadable polymeric component of the structures due to its mechanical and physicochemical properties, unless otherwise stated. PCL is a degradable polyester with a low melting point of around 60° C. allowing multiple processing technologies. It is slowly degraded by hydrolysis of its ester linkages in physiological conditions, making it an appropriate material for the preparation of certain embodiments of long-term in vivo resident structures. It has been used for controlled release and targeted delivery of a variety of drugs.

Various flexible materials were tested for use as a flexible linker. Properties assessed included the ability to undergo 180 degree deformation without breaking, ability to remain in the deformed state for a prolonged period of time such as would occur in a stored pill, and ability to recoil nearly 100% to the original shape. To maximize the mechanical properties while maintaining biocompatibility, an isocyanate crosslinked polyurethane generated from low-molecular weight polycaprolactone monomers was used.

One such implementation consisted of addition of a 6:1.3:0.027:9.5 molar ratio of polycaprolactone diol (MW 530 g/mol): polycaprolactone triol (MW 900 g/mol): linear high molecular weight polycaprolactone (MW 45,000 g/mol): hexamethylene di-isocyanate. The first three ingredients were first mixed at 70 degrees Celsius until well mixed. The mixture was sonicated to remove entrapped air bubbles. The isocyanate as added and mixed for about 30 minutes while maintaining the temperature between 70-75 degrees Celcius. While maintaining temperature, the pre-polymer solution was gently pipetted into PDMS molds of the desired shape. The thermoset was set at 70-75 degrees Celsius for 48 hours at which point the shape is firmly set and minimal residual free isocyanate is present.

FIG. 3 shows an elliptical ring structure configured for gastric residence. The elliptical ring structure comprises a loadable polymeric component and one or more linkers configured for controlled degradation incorporated into the elliptical ring structure. FIG. 3A shows an elliptical ring structure next to a 000-size capsule. The elliptical ring structure has a major axis diameter greater than about 40 mm and a minor axis diameter comparable to the major axis of the 000-size capsule (i.e., about 26 mm). In FIG. 3B, the elliptical ring structure is shown packed into (and bent within) the 000-size capsule. In FIGS. 3C-3D, controlled degradation linkers, which are incorporated into the elliptical ring structure at points along the minor axis, are visible. In FIG. 3D, the elliptical ring structure is twisted such that the axis of the helix is along the minor axis of the elliptical ring structure. The gains of packing efficiency can be seen in FIG. 3E as compared to FIG. 3B.

Example 2—Multi-armed Star Design

Design constraints were addressed by using a combination of relatively rigid elements (loadable polymeric components) as drug matrix that provide mechanical stability and flexible recoil elements (elastic polymeric components.) As shown in FIGS. 4A-5B, two geometric families of rigid and flexible elements were studied in greater detail, a "polygon" family of alternating rigid and flexible elements which fold on itself and a "stellate" family in which rigid elements project from a central flexible element. Designs which could be efficiently encapsulated into a standard size 000 gelatin capsule were generated in Inventor CAD software, 3D printed, and used as positives to make PDMS negative molds. Versions optimized for capsules of other sizes, including larger veterinary capsules, as well as smaller capsules for more ready human consumption including 00-EL, 0-EL were also developed.

Figure 4A:
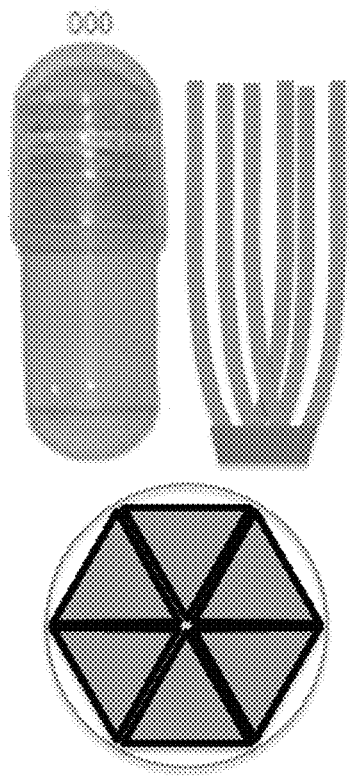
FIGS. 4A-4C are illustrations of (A) an exemplary residence structure comprising projections, and a capsule for containment according to one set of embodiments, (B) illustrations of various exemplary residence structures comprising projections, and (C) reproductions of photographs of exemplary residence structures.
Figure 4B:
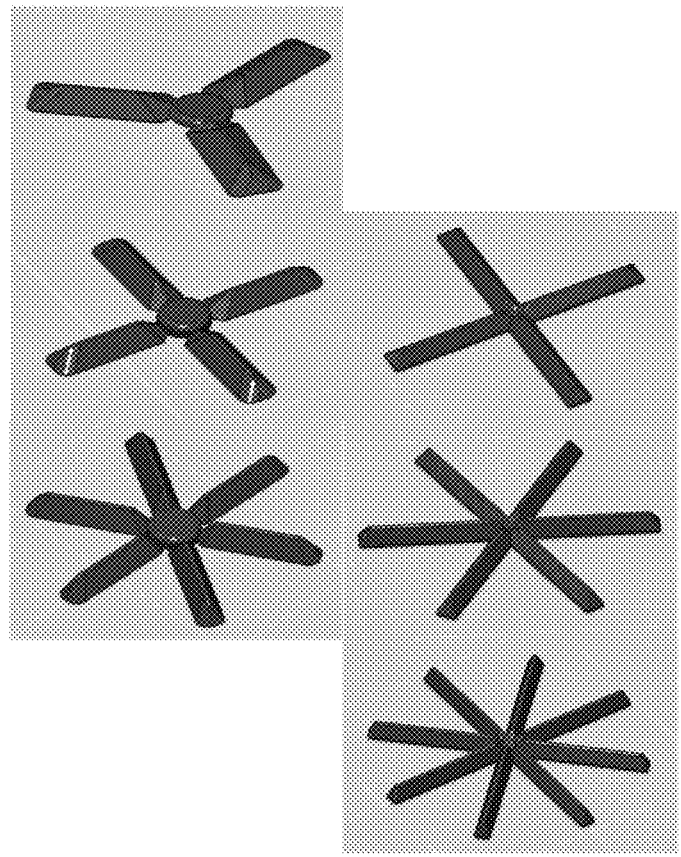
Figure 4C:
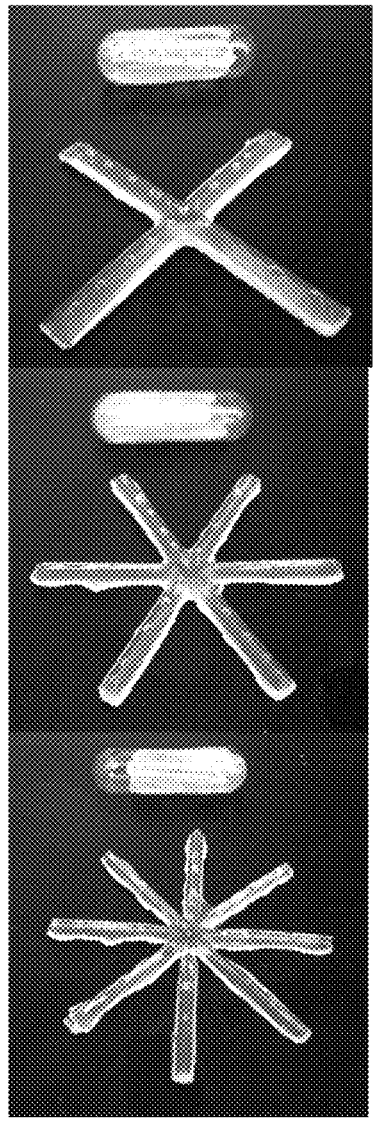

In FIG. 4A, the structure comprises a central core and six radial projections, shown next to a 000-size capsule. The central core comprises an elastic polymeric component comprising elastic PCL, and the projections comprise a rigid loadable polymeric component. Each projection has a length equal to just less than the length of the capsule such that the unencapsulated final form has a circumscribing diameter equal to nearly twice the capsule length. In FIG. 4B, various structures with radial projections having sector shapes with internal sector angles equal to approximately 360°/N are shown. Each structure has projections of 20-mm length within a circumscribing diameter of about 44 mm. For a structure with three radial projections, the design surface was 915 mm² and the design volume was 438 mm³. For a structure with four radial projections, the design surface was 1047 mm² and the design volume was 723 mm³. For a structure with six radial projections, the design surface was 1410 mm² and the design volume was 954 mm³. For a structure with eight radial projections, the design surface was 1658 mm² and the design volume was 1015 mm³. In FIG. 4C, three structures with four, six, and eight radial projections, respectively, are shown packed in capsules and in their unencapsulated forms. The projections are formed from at least one material with a high elastic modulus to increase the resistance to compression and duration of gastric residence.

Table 1 summarized the various sizes of the structures.

TABLE 1

| N = Arms | capsule length (mm) | a = edge length (mm) | capsule width (mm) | w = folded structure width (mm) | Circumscribing radius (mm) = R | Design volume (mm^3) | Design surface (mm^2) |
|---|---|---|---|---|---|---|---|
| 3 | 26 | 20 | 9.9 | 8.5 | ~44 | 438 | 915 |
| 4 | 26 | 20 | 9.9 | 8.5 | ~44 | 723 | 1047 |
| 5 | 26 | 20 | 9.9 | 8.5 | ~44 | | |
| 6 | 26 | 20 | 9.9 | 8.5 | ~44 | 954 | 1410 |
| 7 | 26 | 20 | 9.9 | 8.5 | ~44 | | |
| 8 | 26 | 20 | 9.9 | 8.5 | ~44 | 1015 | 1658 |

Example 3—Polygonal Design

Figure 5A:
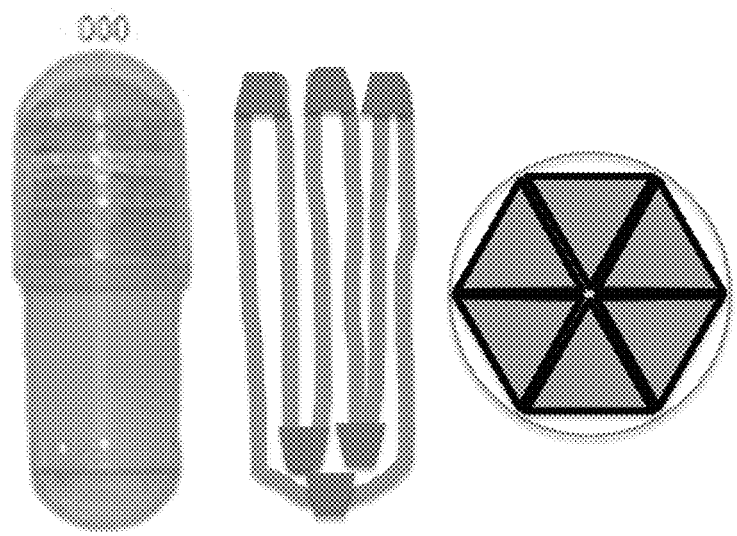
FIGS. 5A-5B are illustrations and photographs of an exemplary polygonal residence structure, according to one set of embodiments.
Figure 5B:
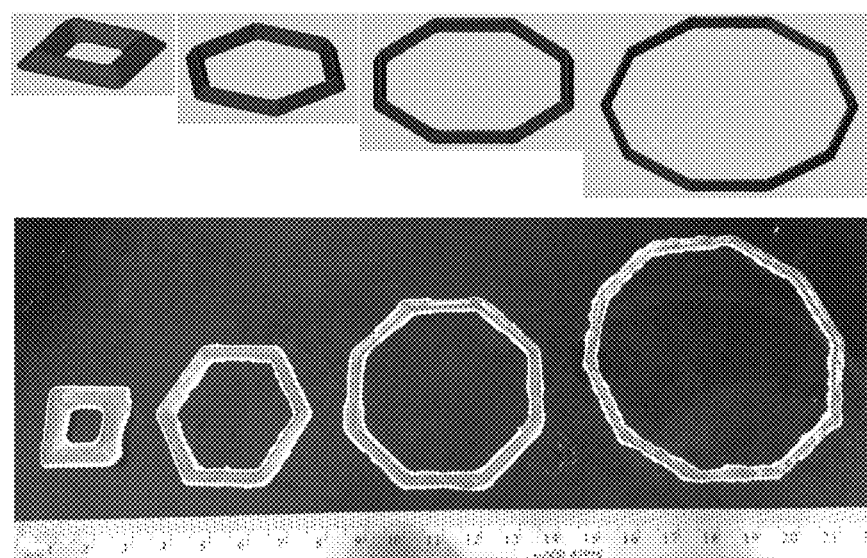

In FIG. 5A, an embodiment with a hexagonal structure is shown next to a 000-size capsule. The vertices of the hexagon comprise elastic polymeric components, and the sides of the hexagon comprise rigid loadable polymeric components. Each side has a length equal to just less than the length of the capsule such that the unencapsulated final form has a circumscribing diameter equal to nearly twice the capsule length. FIG. 5B, various structures with radial projections having sector shapes with internal sector angles equal to approximately 360°/N are illustrated. Four embodiments with square, hexagonal, octahedral, and dodecahedral structures, respectively, are shown in their unencapsulated forms. The shapes are formed from at least one material with a high elastic modulus to increase the resistance to compression and duration of gastric residence.

Each side of each polygon is about 22-mm long, and each folded polygonal structure has a width of about 8.5 mm. For a structure with four sides, the circumscribing diameter was about 15.6 mm, the design surface was about 964 mm$^2$, and the design volume was about 640 mm$^3$. For a structure with six sides, the circumscribing diameter was about 22.0 mm, the design surface was about 1451 mm$^2$, and the design volume was about 998 mm$^3$. For a structure with eight sides, the circumscribing diameter was about 28.8 mm, the design surface was about 1806 mm$^2$, and the design volume was about 1125 mm$^3$. For a structure with ten sides, the circumscribing diameter was about 35.6 mm, the design surface was about 2052 mm$^2$, and the design volume was about 1148 mm$^3$. For a structure with twelve sides, the circumscribing diameter was about 42.5 mm, the design surface was about 2389 mm$^2$, and the design volume was about 1208 mm$^3$. The sizes are summarized in Table 2.

TABLE 2

| N = Edges | capsule length (mm) | a = edge length (mm) | capsule width (mm) | w = folded structure width (mm) | Implied polygon circumscribing radius (mm) R = a/2sin (pL/N) | Design volume (mm^3) | Design surface (mm^2) |
| --- | --- | --- | --- | --- | --- | --- | --- |
| 4 | 26 | 22 | 9.9 | 8.5 | 15.6 | 640 | 964 |
| 6 | 26 | 22 | 9.9 | 8.5 | 22 | 998 | 1451 |
| 8 | 26 | 22 | 9.9 | 8.5 | 28.8 | 1125 | 1806 |
| 10 | 26 | 22 | 9.9 | 8.5 | 35.6 | 1148 | 2052 |
| 12 | 26 | 22 | 9.9 | 8.5 | 42.5 | 1208 | 2389 |

Example 4—Ingestion of Structures

Figure 6:
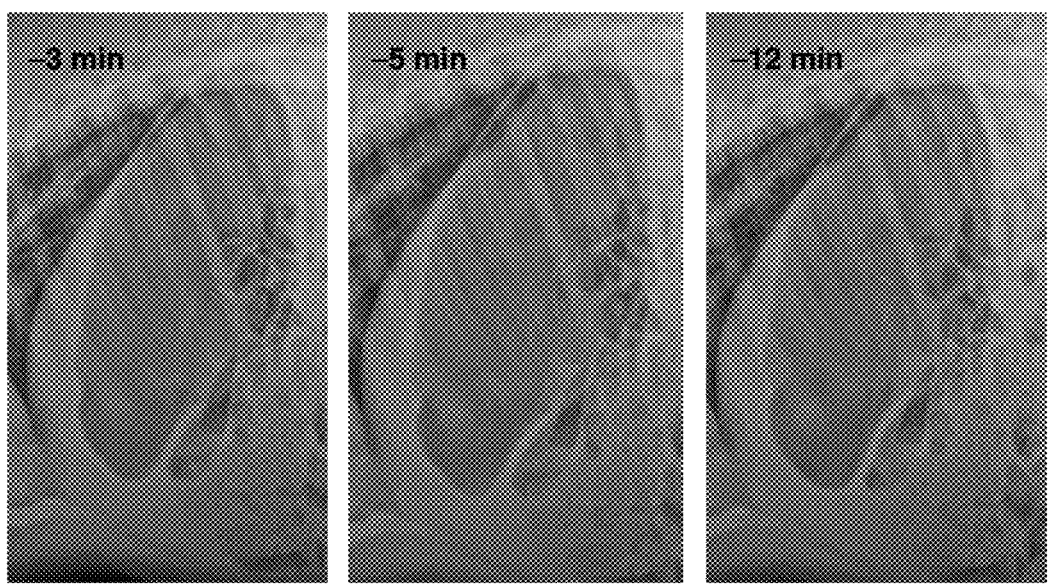
FIG. 6 is a series of X-ray images obtained in a large animal model with a residence structure, according to one set of embodiments.

FIG. 6 is a series of chest/abdominal X-ray images obtained in a large animal model at 3 minutes, 5 minutes, and 12 minutes respectively after ingestion, demonstrating deployment of a multi-armed structure from a capsule and in vivo adoption by the structure of the native conformation over about 12 minutes.

Figure 7:
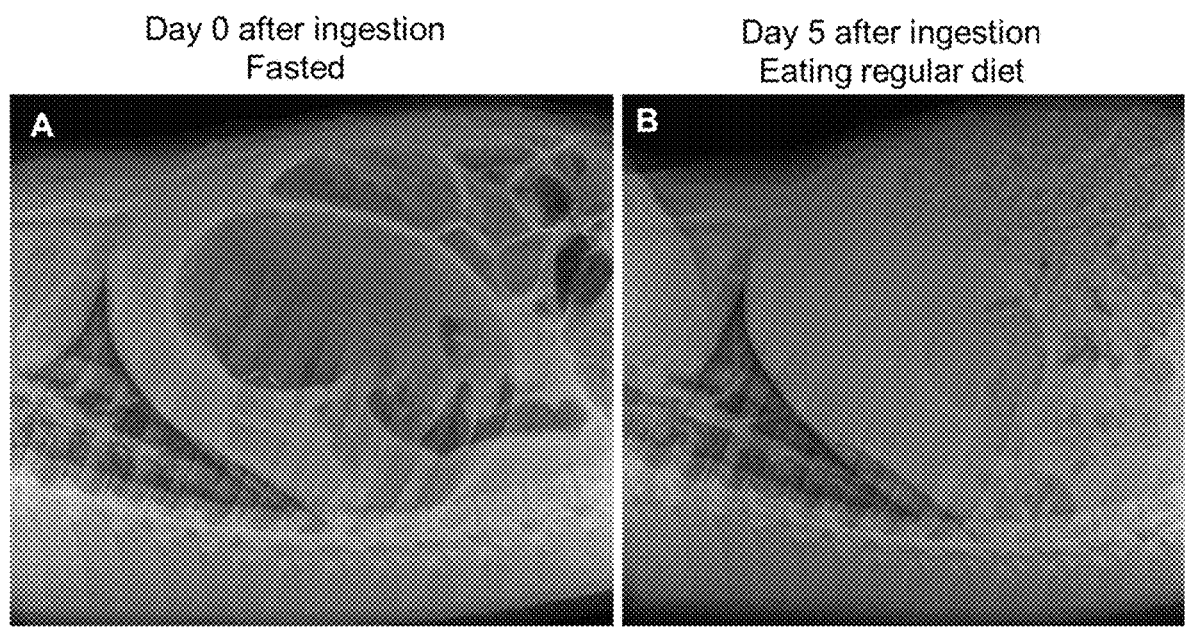
FIG. 7 is a series of X-ray images obtained in a large animal model with a residence structure, according to one set of embodiments.

Similarly, FIG. 7 includes a series of chest/abdominal X-ray images obtained in a large animal model after ingestion of a hexagonal retention/delivery structure, the sides formed with polycaprolactone and the vertices comprising enteric elastomer linkers, in accordance with some embodiments. Each retention/delivery structure was packed tightly into a 000 capsule and expanded to its native shape after reaching a gastric cavity. FIG. 7A is an image taken after ingestion when the subject was fasting, and FIG. 7B is an image taken five days after ingestion when the subject was eating a regular diet. Table 3 presents the results of eight trials in six different pigs using the hexagonal retention/delivery structure according to some embodiments. As shown in the table in FIG. 7, the structure was successfully retained in the gastric cavity in all cases on Day 0 and Day 2, and in three cases, on Day 5. In the five other cases on Day 5, the enteric elastomer linkers degraded, and the structure passed safely through the gastrointestinal tract.

TABLE 3

|  | Day 0 | Day 2 | Day 5 |
| --- | --- | --- | --- |
| Gastric cavity retention | 8/8 | 8/8 | 3/8 |
| Dissolution of linker and safe passage | 0/8 | 0/8 | 5/8 |
| Adverse events | 0/8 | 0/8 | 0/8 |

8 Trials in 6 Different Pigs of a Hexagonal Structure with Enteric Linkers

Example 5—Enteric Elastomers

Figure 8A:
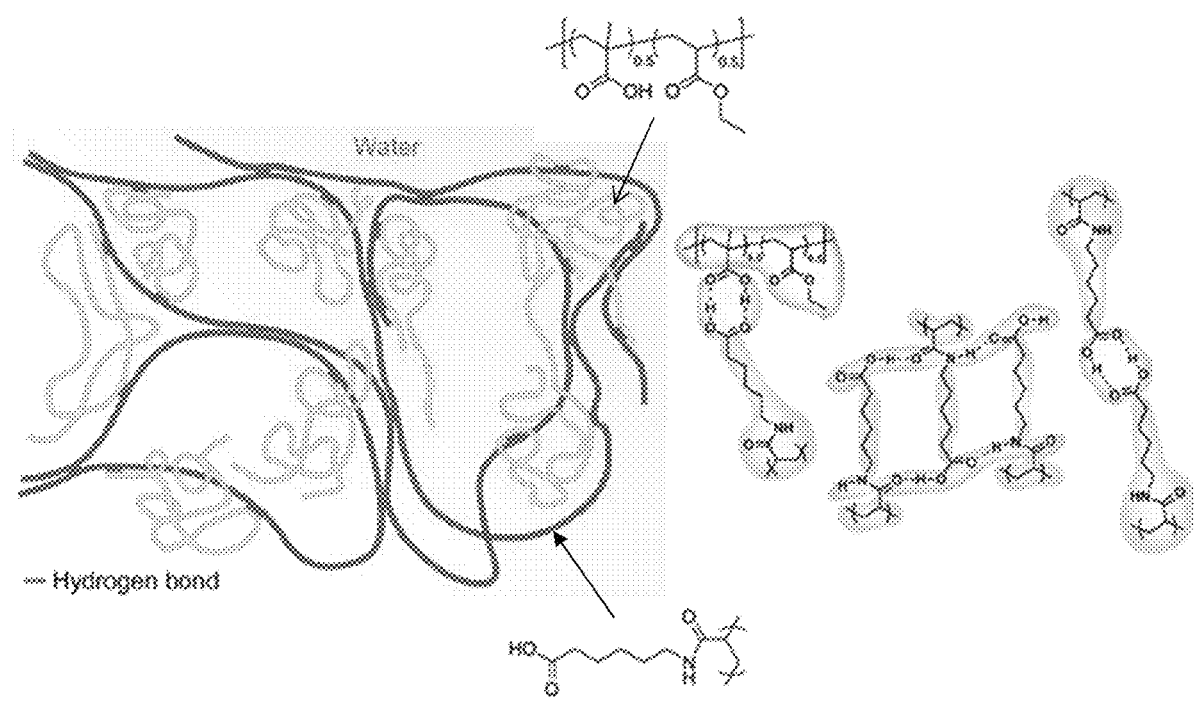
FIG. 8A is an illustration of an enteric elastomer for use in a residence structure, according to one set of embodiments.
Figure 8B:
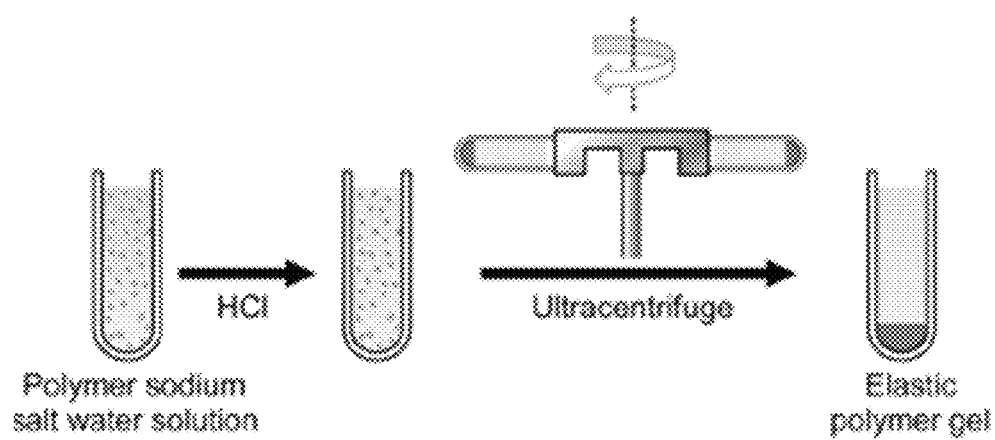
FIG. 8B is an illustration of the preparation of an enteric elastomer for use in a residence structure, according to one set of embodiments.

FIG. 8 is a schematic representation of an enteric elastomer and a method of preparing an enteric elastomer in accordance with some embodiments. In FIG. 8A, a polymer gel network is illustrated with a first set of lines representing synthesized poly(acryloyl-6-aminocaproic acid); a second set of lines representing linear poly(methacrylic acid-co-ethyl acrylate) (e.g., EUDRAGIT® L 100-55, available from Evonik Industries AG (Essen, Germany)); a plurality of boxes representing hydrogen bonds between polymer chains; and spots representing water molecules. In FIG. 8B, a manufacturing process flow is illustrated. From the left of FIG. 8B, a poly(acryloyl-6-aminocaproic acid) sodium salt water solution and a poly(methacrylic acid-co-ethyl acrylate) sodium salt water solution were mixed with one of various ratios (including, but not limited to 1:0, 1:1, and 1:2), into a homogeneous polymer sodium salt water solution. Then, two polymers were co-precipitated upon the addition of HCl solution. Precipitates of polymer complexes were transformed into an enteric, elastic polymer gel, recovered at the bottom of the centrifuge tube. The formed enteric elastomer could be cut and/or pressure molded into various shapes for the construction of structures, mechanical characterizations, etc.

Figure 8C:
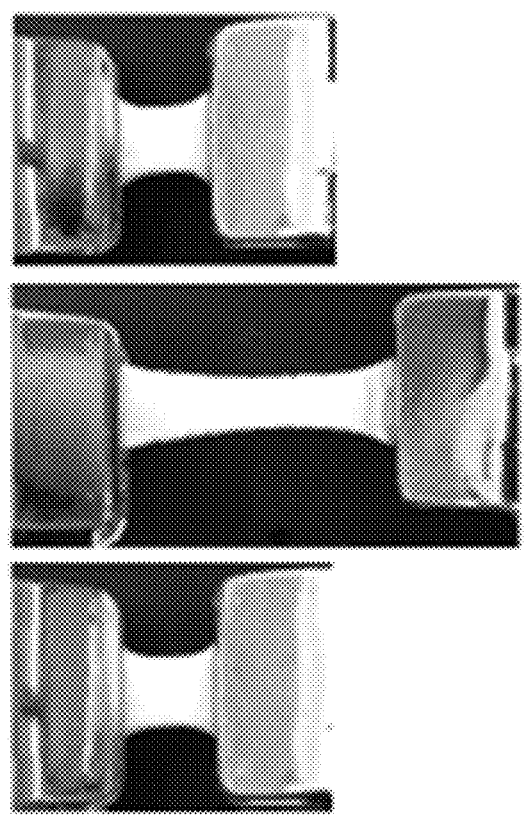
FIG. 8C is a series of reproductions of photographs obtained during mechanical testing of an enteric elastomer, according to one set of embodiments.

In FIG. 8C, three optical images of stretch testing of an enteric elastomer are shown. The enteric elastomer had a 1:2 ratio of poly(acryloyl-6-aminocaproic acid) to poly(methacrylic acid-co-ethyl acrylate). The top image shows an enteric elastomer, 1.5 cm long before stretching. The middle image shows the enteric elastomer stretched to three times its initial length. The bottom image shows the enteric elastomer five minutes after the external force was removed and the enteric elastomer had returned to its initial length.

FIG. 9 illustrates the morphology, mechanical, dissolution, and cytotoxicity characterizations of three formulations of enteric elastomers in accordance with some embodiments. In FIG. 9A, a series of scanning electron microscope (SEM) images show the morphology of dried enteric elastomers with three different ratios of poly(acryloyl-6-aminocaproic acid) (PA6ACA) to EUDRAGIT® L 100-55 (L 100-55), 1:0, 1:1, and 1:2 respectively. The scale bar in the images is equal to 50 μm. All three formulations of enteric elastomers have porous structures, but higher concentrations of EUDRAGIT® L 100-55 correlated with decreasing pore size. The formulations were dried by lyophilization for 48 hours to measure their water content. The water content decreased from 31.6 wt % in pure poly(acryloyl-6-aminocaproic acid), to 27.7 wt % of the enteric elastomer with the 1:1 ratio, and to 26.4 wt % of the enteric elastomer with the 1:2 ratio, consistent with the SEM observations.

Figure 9A:
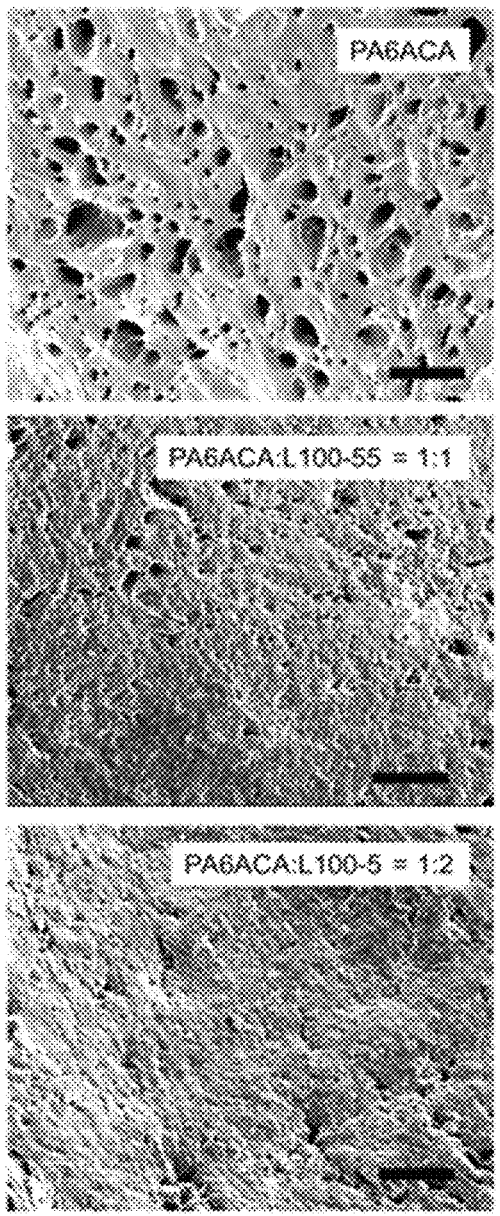
FIG. 9A is illustrates materials tested and results obtained for the mechanical characterization of several exemplary enteric elastomers, according to one set of embodiments.
Figure 9A:
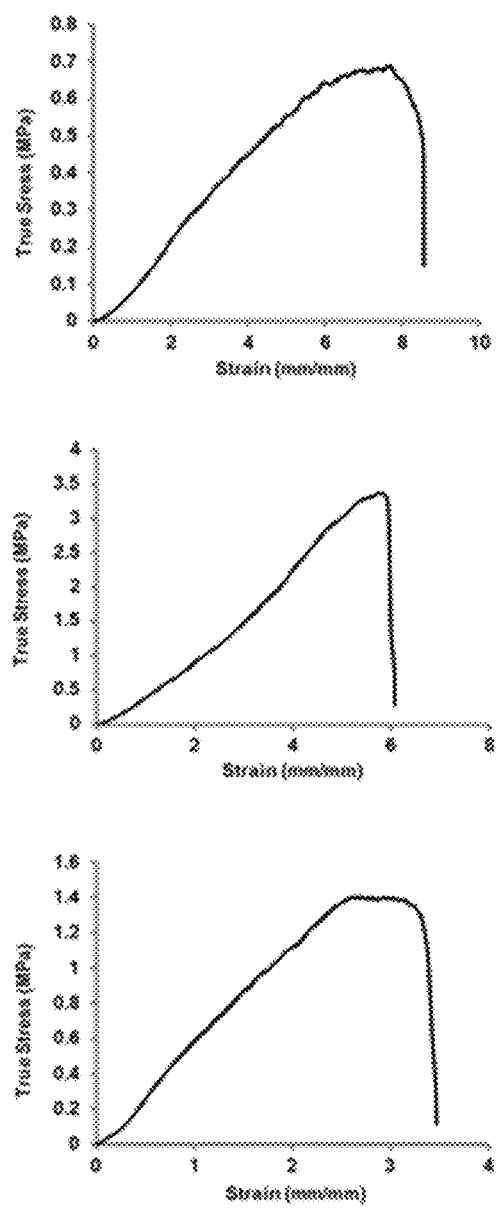

To test the elastic properties of the enteric elastomers, tensile stress testing was conducted. In FIG. 9A, a series of corresponding true stress-true strain plots for the enteric elastomers are presented. The Young's modulus and tensile strength increases with increasing amounts of EUDRAGIT® L 100-55, while the strain reduces from 857% of poly(acryloyl-6-aminocaproic acid) itself to 341% of the enteric elastomer with the ratio 1:2.

Figure 9B:
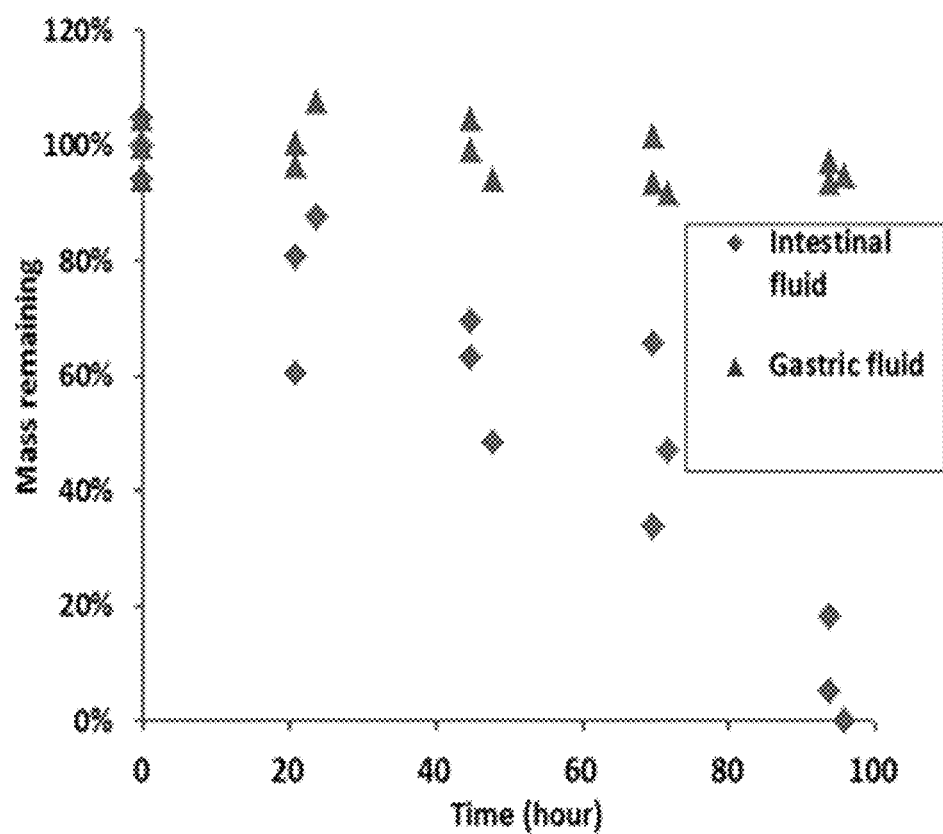
FIG. 9B is a plot showing the dissolution characterization of an enteric elastomer, according to one set of embodiments.

After demonstrating the elastic properties of the enteric elastomers, their enteric ability was evaluated by dissolution testing in simulated gastric fluid and simulated intestinal fluid. In FIG. 9B, a plot compares the results of corresponding dissolution tests of the enteric elastomers in simulated gastric fluid and simulated intestinal fluid. Poly(acryloyl-6-aminocaproic acid) showed long-term stability in simulated gastric fluid without distinguishable mass loss for over 4 days. In contrast, within the same period of time, poly (acryloyl-6-aminocaproic acid) dissolved in simulated intestinal fluid with pH of 6.8.

Figure 9C:
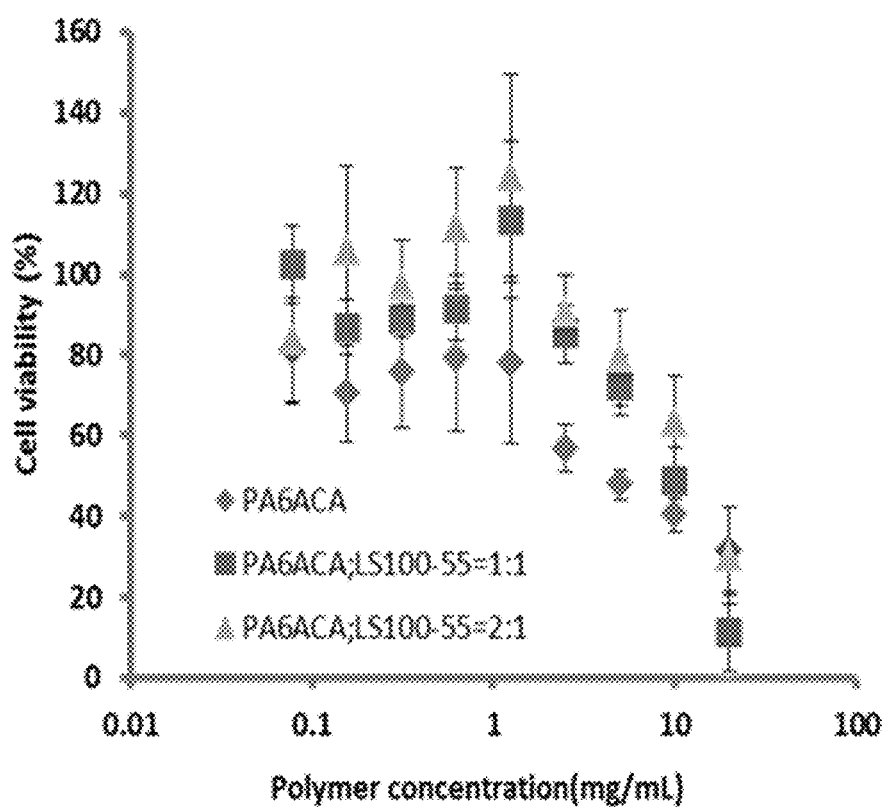
FIG. 9C is a plot of cell viability (i.e. cytotoxicity) of an enteric elastomer, according to one set of embodiments.

To demonstrate the biocompatibility and safety of poly (acryloyl-6-aminocaproic acid) after being dissolved, the poly(acryloyl-6-aminocaproic acid) sodium salt was tested for cytotoxicity in HeLa cells at a range of concentrations. In FIG. 9C, a plot compares the results of corresponding cytotoxicity studies of the enteric elastomer formulations in the HeLa cells. After a 24-hour incubation, no significant cytotoxicity was observed for poly(acryloyl-6-aminocaproic acid) over a range of concentrations from 0.0001 mg/mL to 5 mg/mL. The observed cytotoxicity at high concentration (above 5 mg/mL) may be due to a change in pH of the cell culture medium after dissolving the polymer sodium salt. Therefore, poly(acryloyl-6-aminocaproic acid) can be biocompatible.

Figure 10:
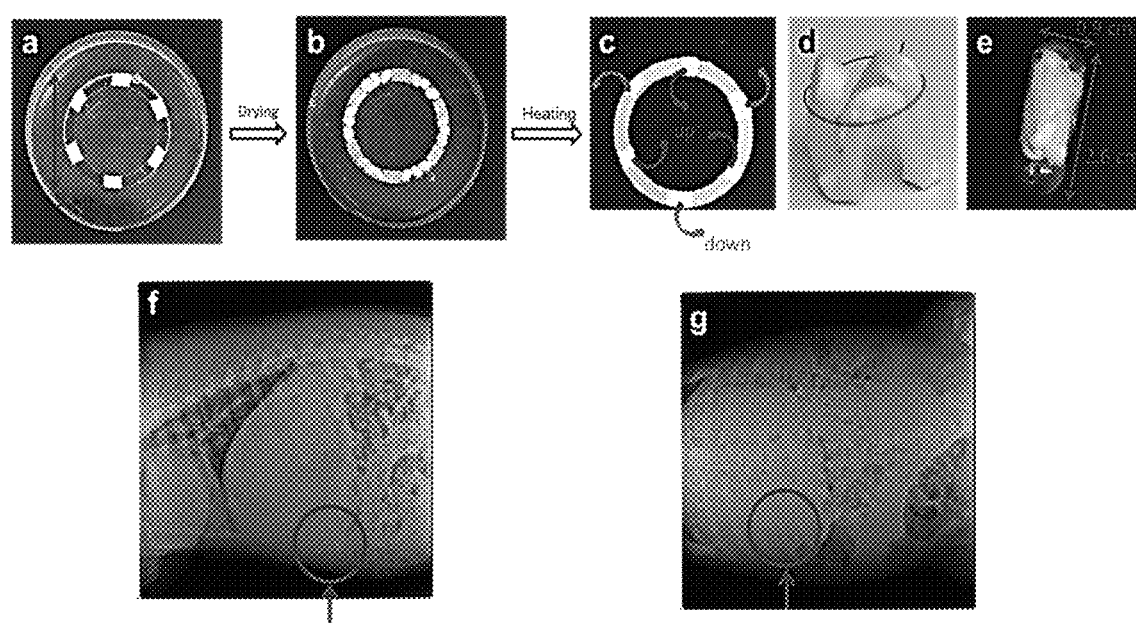
FIG. 10 are illustrations showing the construction and in vivo evaluation of the ring-shaped residence structure, according to one set of embodiments.

In order to evaluate the stability of an enteric elastomer in vivo, a circle composed of polycaprolactone (PCL) arcs with intervening enteric elastomer linkers was made according to some embodiments. FIG. 10 illustrates the construction and in vivo evaluation of the ring-shaped gastric residence structure in accordance with some embodiments. In FIG. 10A, six pieces of enteric elastomer were fitted into a ring shaped polydimethylsiloxane (PDMS) mold with an outer diameter of 3.0 cm, inner diameter of 2.8 cm, and depth of 0.2 cm. After the elastic enteric polymer gels were dried by vacuum, FIG. 10B shows the placement of a polycaprolactone (PCL) beads in between the six pieces of enteric elastomer. After PCL was melted and solidified, FIG. 10C shows a ring-shaped structure removed from the mold and illustrates a method of folding the structure to reach the result shown in FIG. 10D. In FIG. 10E, the folded structure has been packed into a gelatin capsule with a length of 2.6 cm and diameter of 0.9 cm. FIGS. 10F-G are lateral and anteroposterior X-ray images, respectively, of a pig after administering the gelatin capsule containing the ring-shaped structure (radiopaque metal balls were embedded in the PCL segments for imaging). After the ring shaped structure in the capsule was delivered to a pig through its esophagus, the capsule was dissolved in the stomach and the ring-shaped structure was released and recovered its shape.

Example 6—Formation of Linkers

Enteric linker elements were formed by compressive molding. In one embodiment, Eudragit L100-55 (Evonik), an enteric material known to the art to have a pH-dependent dissolution profile, was blended with a plasticizer (triacetin) in a ratio of between 60:40 and 80:20. 3 g of the resulting mixture was placed between two 6×6 inch Teflon sheets and placed on a hot press at 110-120 degrees Celsius and compressed to 5000 psi for 20 minutes. The Teflon sheets were removed from the press and quenched in room temperature tap water briefly for 10 seconds, after which the Eudragit film was removed.

Linkers with other dissolution profiles were generated in a similar fashion. Eudragit RS PO (Evonik), a water soluble polymer with a time dependent dissolution profile, was blended with a plasticizer (triacetin) at ratios of 70:30 to 85:15, and compressively molded in a similar fashion on a hot press at 100-110 degrees Celsius and 3000 psi for 10-20 minutes.

In some cases, other water soluble polymers such as vinylpyrrolidone-vinyl acetate copolymers (e.g., KOLLIDON® VA 64 (BASF) and KOLLIDON® SR), polyvinylpyrrolidone, cellulose acetate, hydroxypropyl methyl cellulose, or polyvinyl alcohol were compressively molded or cast into films by solvent (for example, water) evaporation to generate sheets of material for use as linkers.

The time- or pH-dependent linkers can be interfaced with the drug loaded polycaprolactone matrix. Several strategies to achieve this were contemplated. In one case, films of the elastic PCL prepolymer solution were painted onto both sides of the dissolution film and cured. In the case of Eudragit L100-55, this provided covalent crosslinking of the elastic PCL to the dissolvable linker via urethane linkage formation with available reactive groups. The multilayer film produced in this way had an outer interface of elastic PCL and could be interfaced with linear PCL through a final application of heat for a period of time in a constraining mold.

In another example, biocompatible adhesives were used to interface the dissolution linkers with polycaprolactone. In one case, sheets of polycaprolactone film are generated to facilitate interfacing. Using a plasticizer (Pluronic P407) at 10% w/w ratio with polycaprolactone generally improved the flexibility and reduced brittleness of the polycaprolactone films. Films of polycaprolactone were adhered on either side of the pre-formed dissolution film using biomedical adhesives such as a urethane (e.g., Loctite® M-11FL™ Hysol® Medical Structure Urethane Adhesive) or a cyanoacrylate (e.g., Loctite® 3981 Hysol® Epoxy Structural Adhesive).

Linkers with appropriate geometry were then cut from the multilayered films whose exposed outer layers are polycaprolactone. These could be interfaced with the drug loaded polycaprolactone matrix readily with an application of heat at the interface.

Example 7—Mechanical Characterization of Elastic Polymers

The PCL elastomer was mechanically characterized using tension, compression, and creep loading. Mechanical characterization was conducted according to ASTM standards D638 (tension), D575 (compression), and D2990 (Creep).

Tension

Figure 11A:
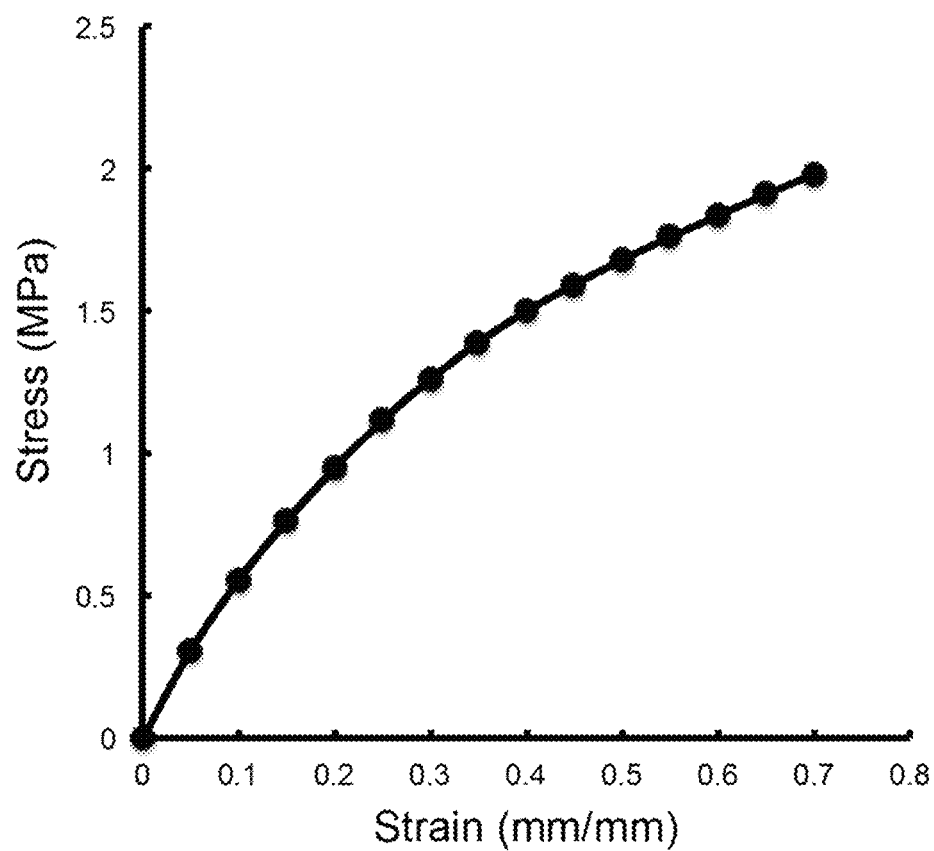
FIG. 11A is a plot of stress (MPa) vs. strain (mm/mm) for an elastic polymeric component of an exemplary structure, according to one set of embodiments.

The PCL elastomer was cured into a polymer sheet 2 mm in thickness. The sheet was allowed to cool and a standard dumbbell die (ASTM D-638) was used to cut specimens from the sheet. Specimens were loaded into grips of an Instron testing machine and the gauge length measured using a digital micrometer. Displacement was applied to the specimen at a rate of 10 mm/min until samples ruptured. Force was converted into normal stress (F/A) and displacement into strain (ΔL/L) and is plotted in FIG. 11A.

Compression

Figure 11B:
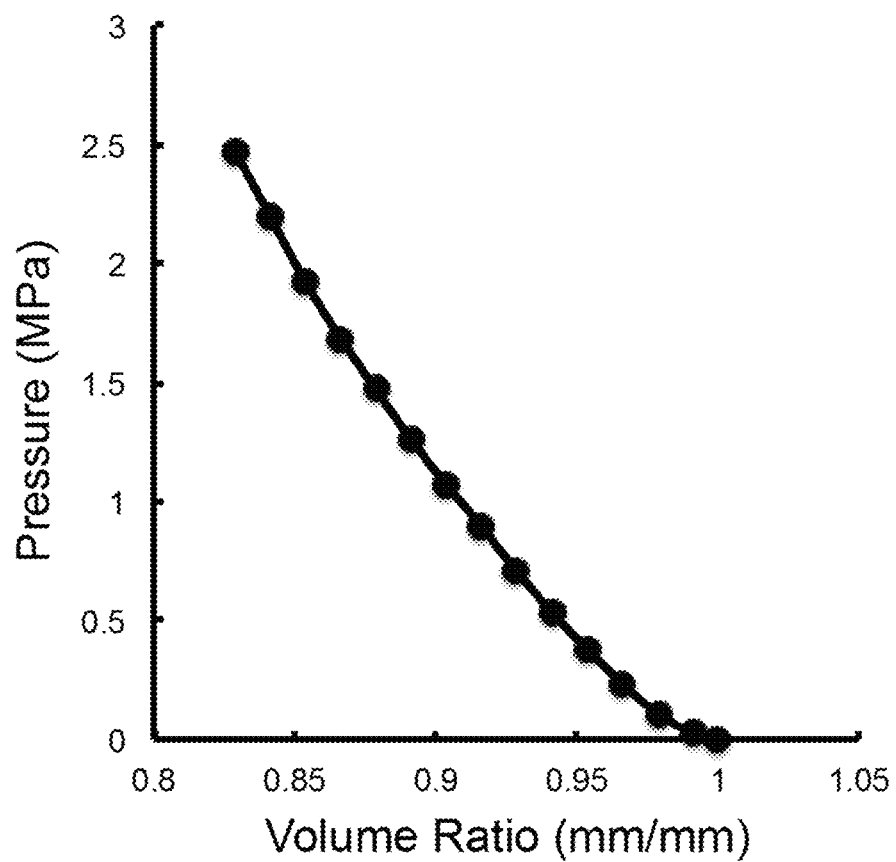
FIG. 11B is a plot of pressure (MPa) vs. strain (mm/mm) for an elastic polymeric component of an exemplary structure, according to one set of embodiments.

The PCL elastomer was cured into a slab 13 mm in thickness. The slab was allowed to cool and a rotating hollow drill bit was used to cut a 28 mm diameter specimen from the slab. Specimens were placed into a constrained loading compression jig and subjected to displacement at 12 mm/min. Specimens were tested until reaching 30% compression strain. Force was converted into pressure (F/A) and displacement into a volume ratio (ΔV/V) and is plotted in FIG. 11B.

Creep

Figure 11C:
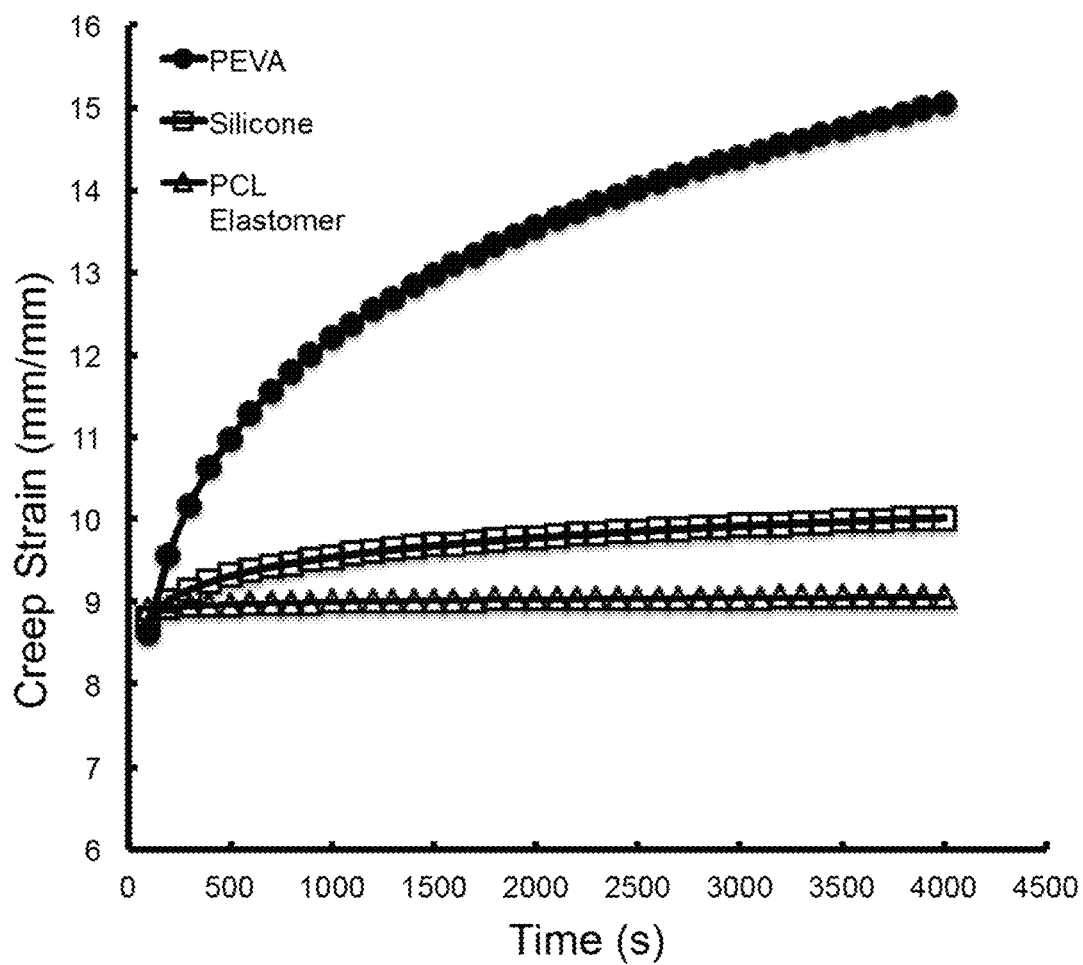
FIG. 11C is a plot of creep strain (mm/mm) vs. time (sec) for various elastic polymeric components of an exemplary structure, according to one set of embodiments.

PCL elastomer, polydimethylsiloxane (silicone), and poly ethylene vinyl acetate (PEVA) were cured into a polymer sheets 2 mm in thickness. The sheets were allowed to cool and a standard dumbbell die (ASTM D-638) was used to cut specimens from the sheets. Specimens were loaded into grips of an Instron testing machine and the gauge length measured using a digital micrometer. A constant stress corresponding to 30% of the ultimate tensile strength of each material was applied to the specimens for 60 min. The force and displacement were calculated throughout the test and converted into normal stress (F/A) and strain (ΔL/L) and is plotted in FIG. 11C.

Example 8—Finite Element Analysis of Retention Structure

Figure 12:
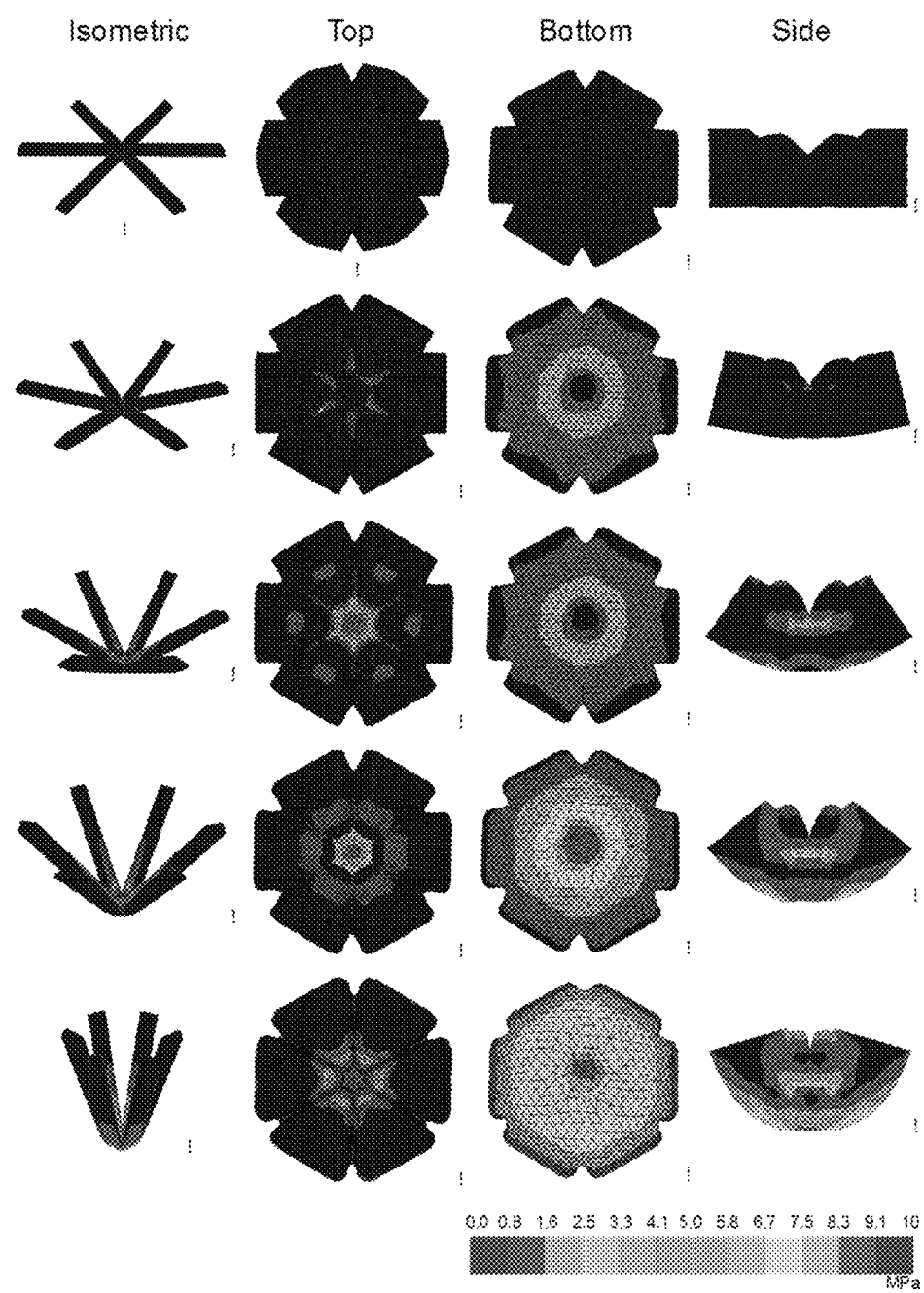
FIG. 12 are isometric, top, bottom, and side views of a finite element modeling simulation of a residence structure undergoing deformation, according to one set of embodiments.

The finite element method was used to analyze the stress and strain profiles of structures in SIMULIA Abaqus FEA software. The geometry of structures was imported into Abaqus from AutoDesk Inventor. The material properties of the PCL elastomer were defined using the Mooney-Rivlin hyperelastic model from tension and compression tests mentioned above. The linear PCL arms were assumed to be linear elastic and the modulus was derived from flexural tests described above. The model was meshed using C3D4 elements and the PCL elastomer and linear PCL were bonded at interfaces. A 1mm diameter plate was introduced to the bottom of the PCL elastomer to hold the structure in place throughout deformation. Force was perpendicularly applied to the top of each arm to simulate folding of the structure into a capsule. Following computation the von Misses, maximum principle, longitudinal, and laterial stresses were analyzed. Results of the finite element modelling are shown in FIG. 12.

Example 9—Simulated Pyloric Exit of Retention Structure

Figure 13A:
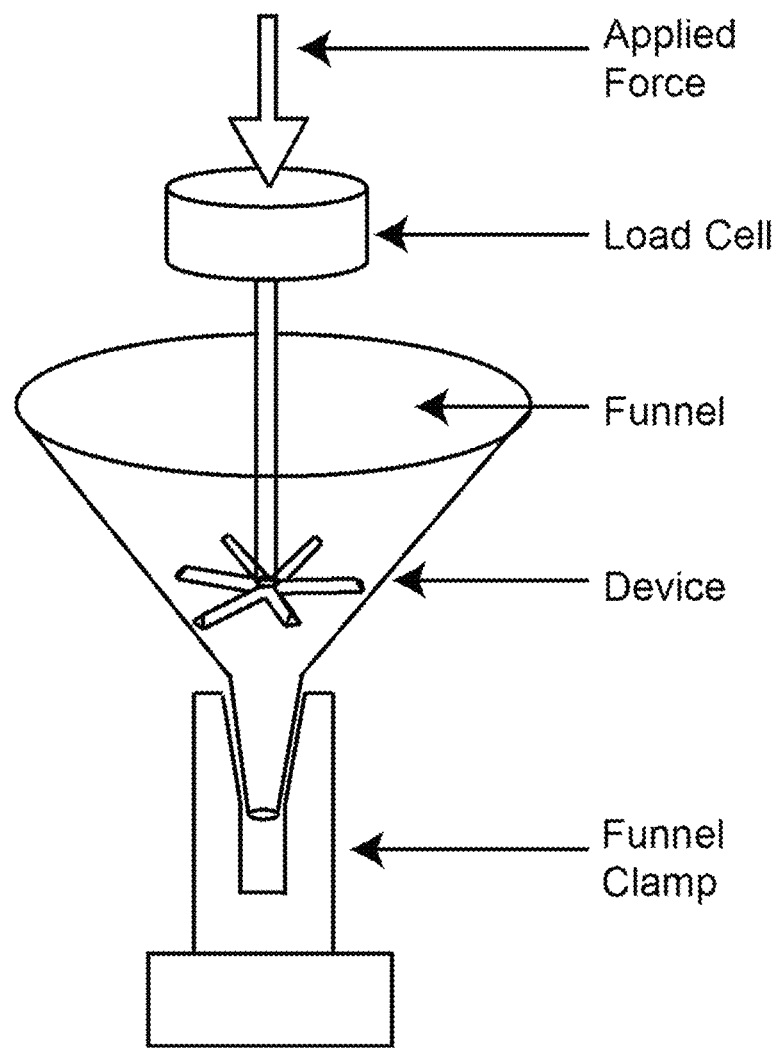
FIG. 13A is a schematic illustration of a residence structure testing apparatus, according to one set of embodiments.
Figure 13B:
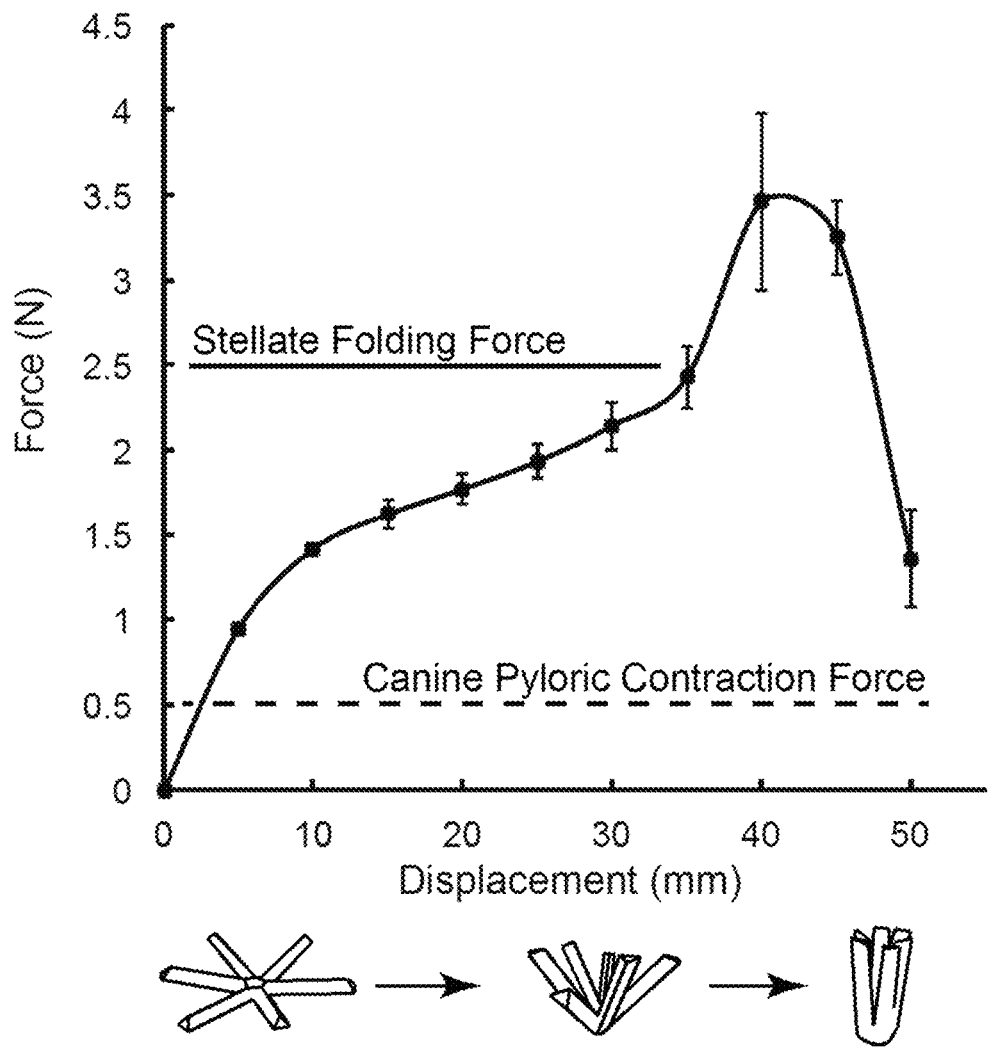
FIG. 13B is a plot of force vs. displacement for a residence structure using the testing apparatus of FIG. 13A, according to one set of embodiments.

A custom experimental setup was developed to better understand transit of retention structures through the pylorus. A schematic of the experimental setup is shown in FIG. 13A. A 20 cm upper diameter by 2 cm lower diameter polypropylene funnel was used to simulate the pyloric sphincter. Structures having a stellate shape as described above were placed into the funnel and a custom-designed plunger was used to push the structure through the 2 cm spout. The plunger was attached to the tension cross-head of an Instron testing machine and the funnel to a clamp. The structure was pushed through the funnel at a rate of 10 mm/min and the force and displacement were captured throughout the test, and is shown in FIG. 13B.

Example 10—Evaluation of Gastric Retention in vivo

To assess particular formulations that were developed for ability to achieve gastric retention, the structures (e.g., hexagonal and stellate) as described above were administered to a large animal model, 35-50 kg Yorkshire pigs. This model was chosen as it is known to have gastric anatomy similar to humans and is widely used in evaluating structures in the gastrointestinal space. The prolongation of food bolus passage in the pig is generally measured in hours, and as such, for evaluation of retention on the order of days this should introduce no more than a small error while providing a good model of gastric anatomy and gastric exit.

Pigs were sedated with Telazol and Xylazine, or in some cases with ketamine, or in some cases isoflurane, and an endoscopic overtube was placed in the esophagus under endoscopic visual guidance during esophageal intubation. Gelatin capsules containing the structures were administered via overtube into the esophagus and/or stomach and the overtube was removed. Serial x-rays were obtained immediately afterwards to document the process of deployment from the gelatin capsule. Blood samples, if necessary, were obtained via cannulation of a mammary vein on the ventral surface of the pig at indicated time points, most often time 0 (prior to administration of the pill), 5 min, 15 min, 30 min, 2 hours, 6 hours, and then daily for a minimum of 5 days and then three times per week. Three times per week, chest and abdominal radiographs were obtained from a minimum of 5 views including anteriorposterior, left lateral and right lateral positions of the chest, upper abdomen, and lower abdomen and rectum. Between 3 and 5×1 mm steel fiducials were embedded via melt casting into the drug delivery PCL arms. These could be tracked radiographically to assess deployment and intactness of the delivery system (configuration), as well as location in the gastric cavity or upper or lower abdomen. Radiographs were also assessed for presence of evidence of complication including pneumoperitoneum or intestinal obstruction. Exemplary radiographs are shown in FIGS. 6 and 7).

Example 11—Evaluation in vitro of Drug Stability and Release

Stability of drugs in the gastric environment was evaluated using HPLC and LC-MS/MS analysis. Hydrophilic drugs were dissolved in simulated gastric fluid (SGF, 0.2% (w/v) NaCl, 0.83% (v/v) HCL, pH=1) in centrifuge tubes. Hydrophobic drugs were dissolved in IAW (isopropanol 70%, acetonitrile 20%, water 10%) with pH adjusted to 1 using HCL. As a control, drugs were dissolved in the same solvents with pH adjusted to 6.0 (using 1M NaOH). After vortexing for 1 min and sonication for 10 min, tubes were placed in a shaking incubator (150 rpm, 37° C.). Samples were collected at defined time points for up to two weeks and analyzed by HPLC and LC-MS/MS to quantify the stability of drugs.

Stability of drugs loaded into PCL based delivery matrices were also studied. Loading of drugs is described below in Examples 16 and 17. Drug loaded structures were kept at acidic conditions (pH=1, 37° C.) and at defined intervals, drug was extracted from the PCL matrix and analyzed by HPLC and/or LC-MS/MS. In order to extract drugs, structures were sonicated in SGF (hydrophilic drugs) or isopropanol (hydrophobic drugs) for 10 min. Fresh drug in SGF or Isopropanol was prepared immediately before analysis as controls.

Stability of Doxycycline (hydrophilic) in SGF (pH=1, 37° C.)

Figure 14:
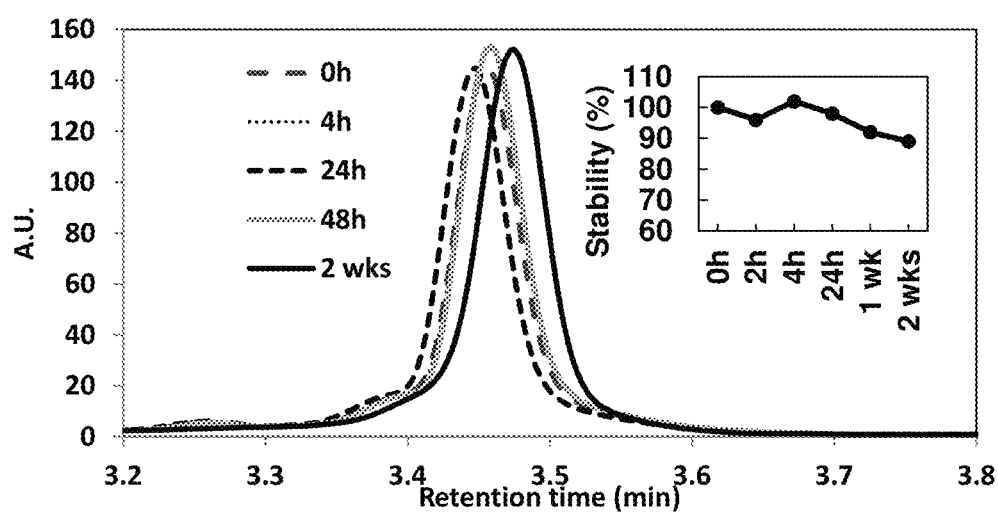
FIG. 14 is a plot of the stability of Doxycycline in SGF (pH=1, 37° C.) over two weeks as analyzed by High Performance Liquid Chromatography (HPLC,) according to one set of embodiments.

Stability of Doxycycline in SGF (pH=1, 37° C.) over two weeks analyzed by HPLC is shown in FIG. 14. An Agilent 1260 infinity model HPLC system equipped with an autosampler and a C8 reversed phase column (4.6×150-mm, i.d., 5-um particle size) was used. The mobile phase was ACN/water+0.1% formic acid pH 3.5 (60/40). 20 μl of samples was injected to the column at a mobile phase flow rate of 1 mL/min and the UV absorption at 350 nm was recorded over 10 min.

Stability of Artemether (hydrophobic) in IAW (pH=1, 37° C.)

Figure 15:
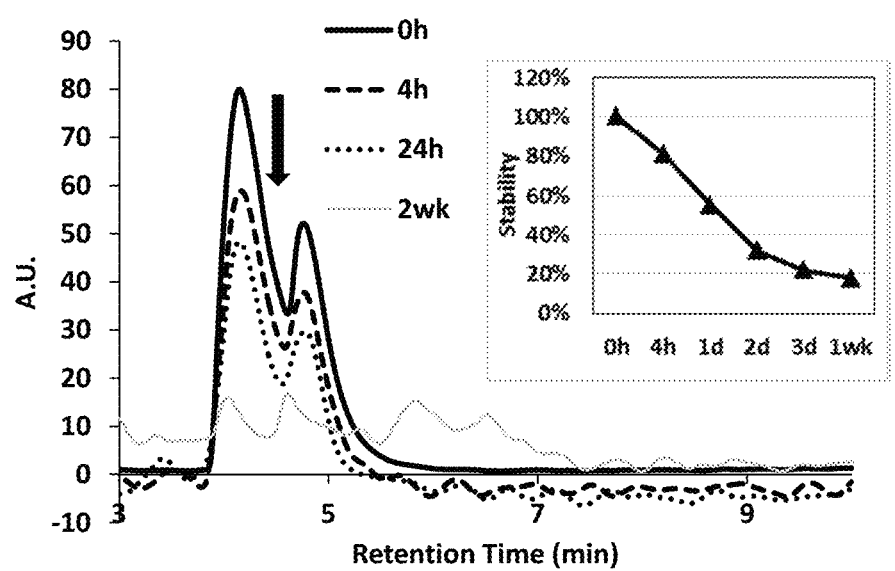
FIG. 15 is a plot of the stability of Artemether in isopropanol 70%, acetonitrile 20%, water 10% (IAW) (pH=1, 37° C.) over two weeks as analyzed by HPLC, according to one set of embodiments.

Stability of Artemether in IAW (pH=1, 37° C.) over two weeks analyzed by HPLC is shown in FIG. 15. The area under curve (AUC) associated with the drug was used to quantify the stability percentage.

Stability of Ivermectin in solution or in PCL structures in acidic conditions (pH=1, 37° C.)

Figure 16A:
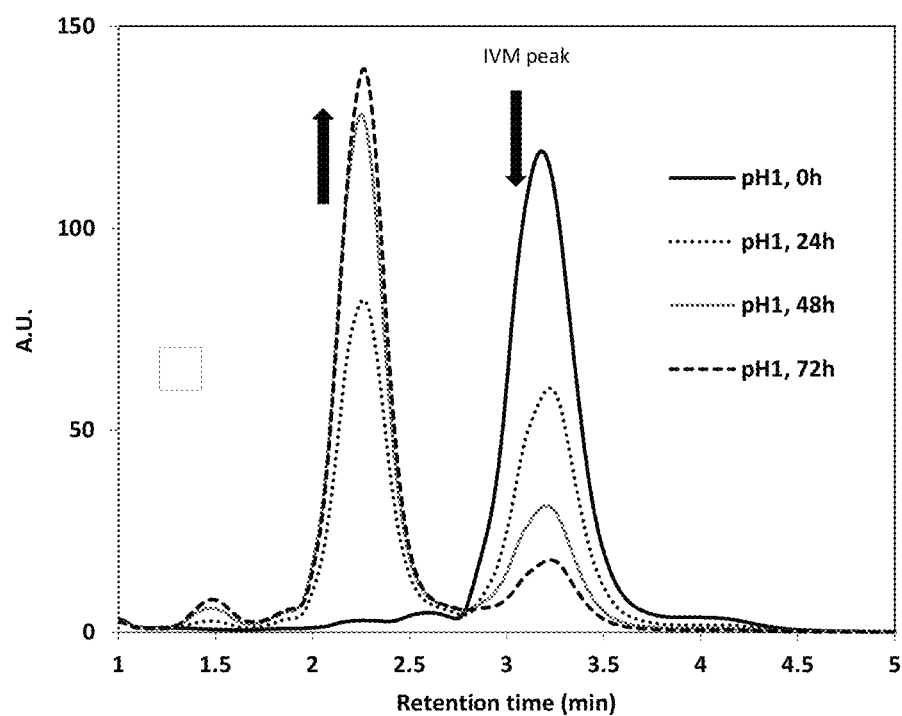
FIGS. 16A-B are plots of the stability of Ivermectin (A) in solution or (B) in polycaprolactone (PCL) structures in acidic conditions (pH=1, 37° C.), according to one set of embodiments.
Figure 16B:
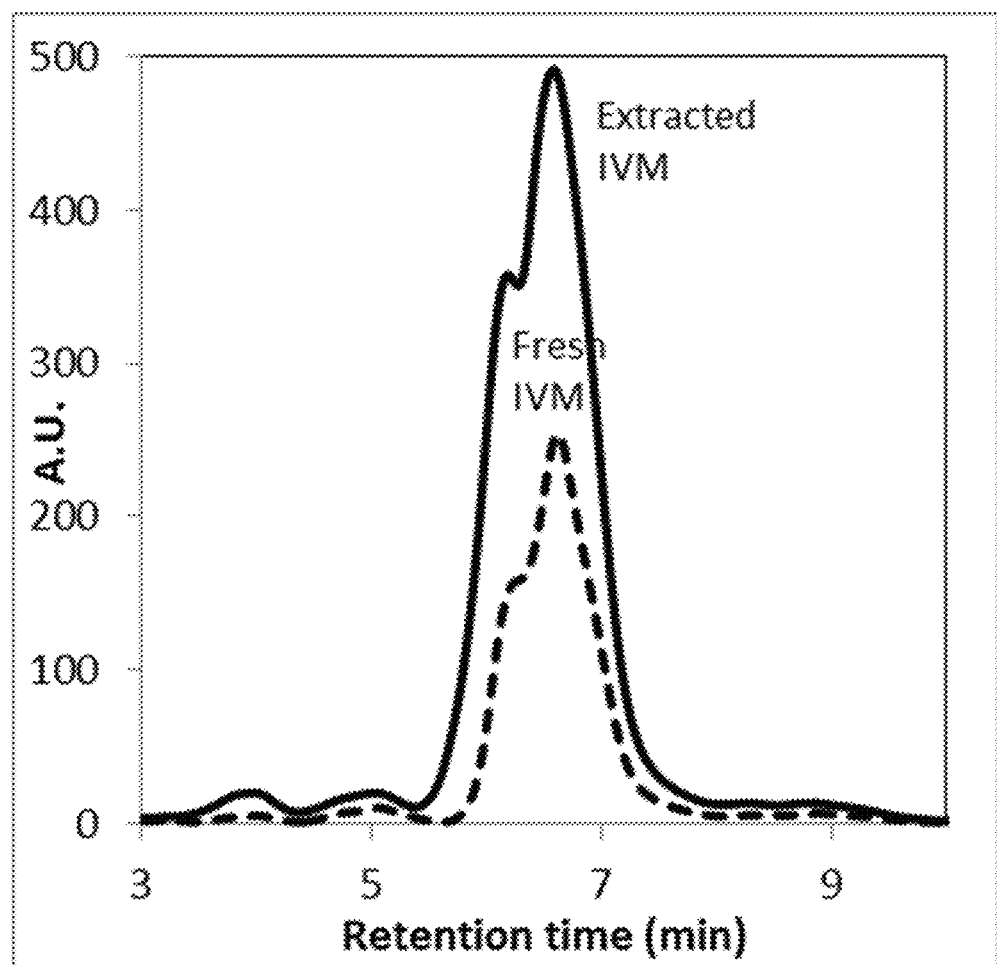

Free Ivermectin is unstable in acidic conditions (IAW, pH=1, 37° C.) is shown in FIG. 16A. PCL structures protected ivermectin against acidic degradation. Ivermectin (IVM) loaded structures, shown in FIG. 16B, were placed in SGF+RH solution (pH=1, 37° C.) for 72h. Drug was extracted by sonicating the structure in isopropanol for 10 min. The HPLC chromatogram of extracted IVM was similar to that of fresh IVM dissolved in isopropanol, indicating that PCL structures protected IVM in acidic environment.

Example 12—in vitro Drug Release Studies

Drug loaded oral delivery structures with varying compositions were prepared as described in Examples 16 and 17. Structures loaded with hydrophilic drugs were placed in sealed cups with 100 mL of SGF. For hydrophobic drugs, Kolliphor® RH40, a non-ionic oil-in-water solubilizing agent, was added to SGF (0.25% (w/v)) to increase the solubility of released drugs. The cups were placed in a shaking incubator (150 rpm, 37° C.). Samples were collected at defined time points for up to two weeks and analyzed by HPLC and LC-MS/MS to quantify the amount of drug released.

In vitro Release of Doxycycline (hydrophilic) Loaded Structures in SGF

Figure 17A:
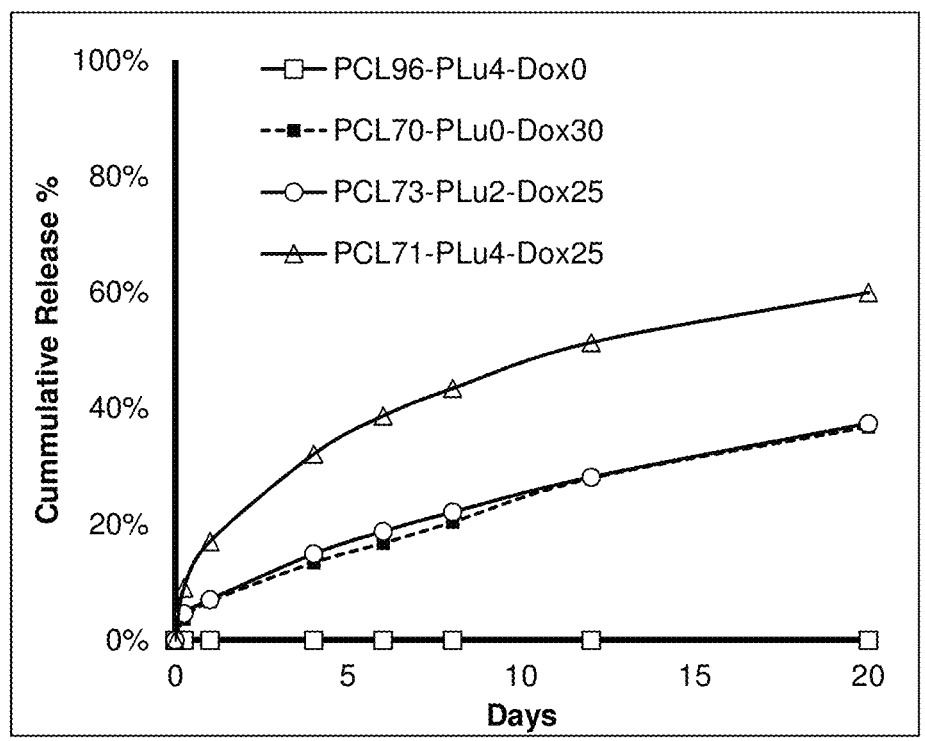
FIG. 17A is a plot that shows the in vitro release of doxycycline loaded PCL stars in simulated gastric fluid (SGF) (pH=1, 37° C.), according to one set of embodiments.

FIG. 17A shows the in vitro release of doxycycline loaded PCL stars in SGF (pH=1, 37° C.): Pluronic P407, a hydrophilic surfactant, was added to the PCL matrix to facilitate drug suspension in the polymer matrix and to tune the release kinetics. Drug concentration in the release media was measured by HPLC. The ratio of PCL:PLu:Dox is expressed as wt % in the figure legend.

In vitro Release of Ivermectin (hydrophobic) Loaded Structures in SGF+RH40

Figure 17B:
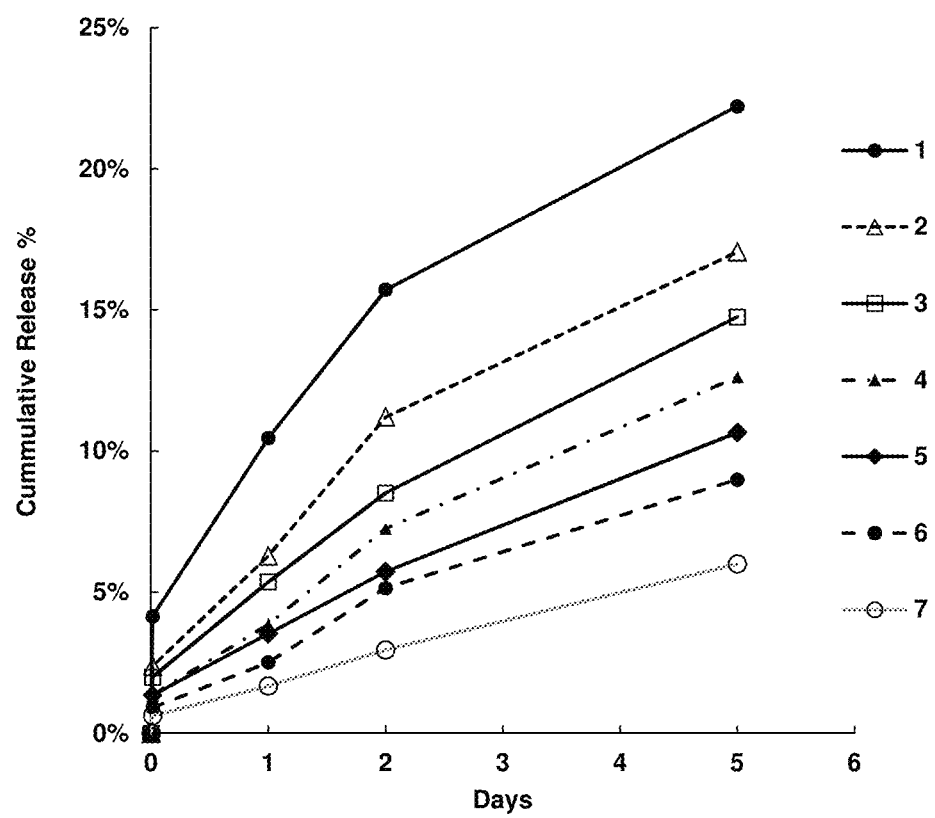
FIG. 17B is a plot that shows in vitro release of Ivermectin (IVM) loaded star-shaped structures with different formulations in SGF and Kolliphor® RH40, a non-ionic oil-in-water solubilizing agent (RH40), (pH=1, 37° C.), according to one set of embodiments.

FIG. 17B shows in vitro release of Ivermectin (IVM) loaded star-shaped structures with different formulations in SGF+RH40 (pH=1, 37° C.). Different excipients, i.e., RH40, Pluronic P407, and Soluplus, were added to tune the release kinetics, as shown in Table 4. Drug concentration in the release media was measured by HPLC.

TABLE 4

| Batch | PCL | IVM | RH40 | P407 | Soluplus |
|---|---|---|---|---|---|
| 1 | 55 | 20 | 20 | 5 | |
| 2 | 60 | 20 | 20 | | |
| 3 | 65 | 20 | 10 | 5 | |
| 4 | 70 | 20 | 10 | | |
| 5 | 70 | 20 | | 10 | |
| 6 | 55 | 20 | | 5 | 20 |
| 7 | 65 | 20 | | 5 | 10 |

Figure 17C:
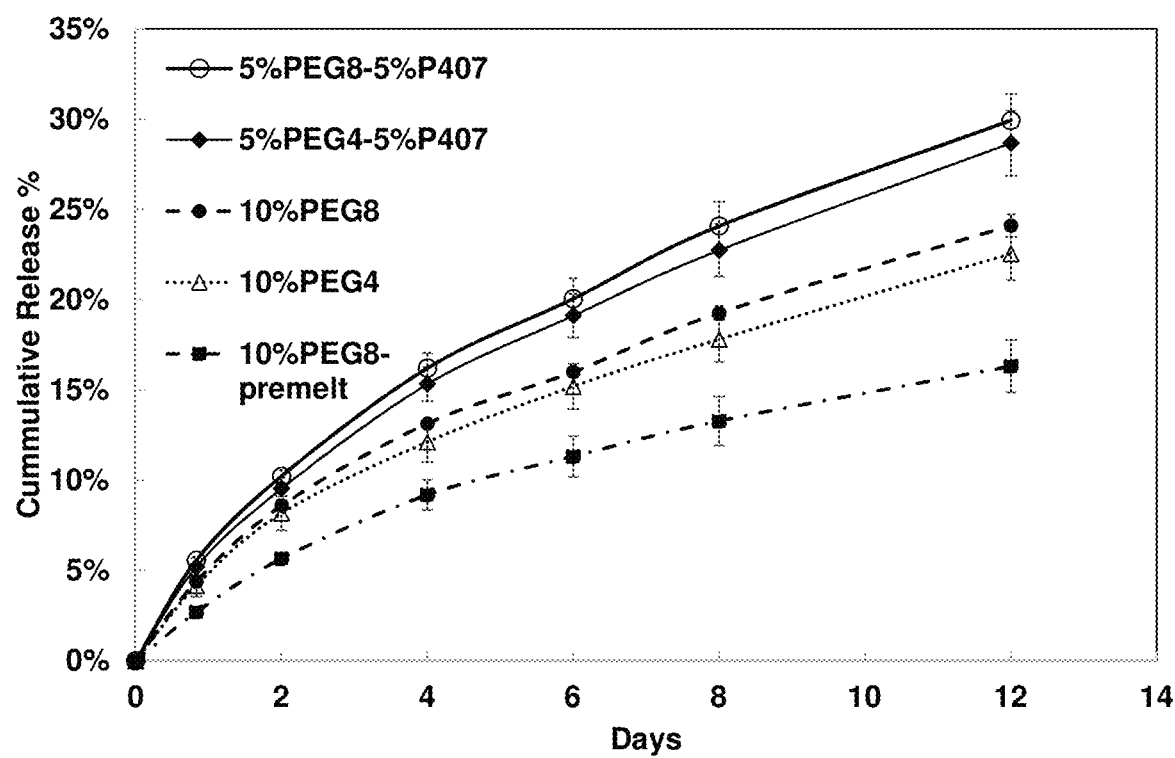
FIG. 17C is a plot that shows the in vitro release of IVM loaded star-shaped structures with different formulations in SGF+RH40 (pH=1, 37° C.), according to one set of embodiments.

FIG. 17C shows in vitro release of Ivermectin (IVM) loaded star-shaped structures with different formulations in SGF+RH40 (pH=1, 37° C.). All formulations include 70% PCL, 20% IVM, and 10% excipient. Excipients include 4-arm and 8-arm branched PEG, and Pluronic P407. For "premelt" sample, IVM and PEG8 were premelted before mixing and re-melting with PCL. Drug concentration in the release media was measured by HPLC. Error bars represent SD of three independent replicates.

Example 13—Flexural Properties of Drug-Loaded PCL Segments

Figure 18:
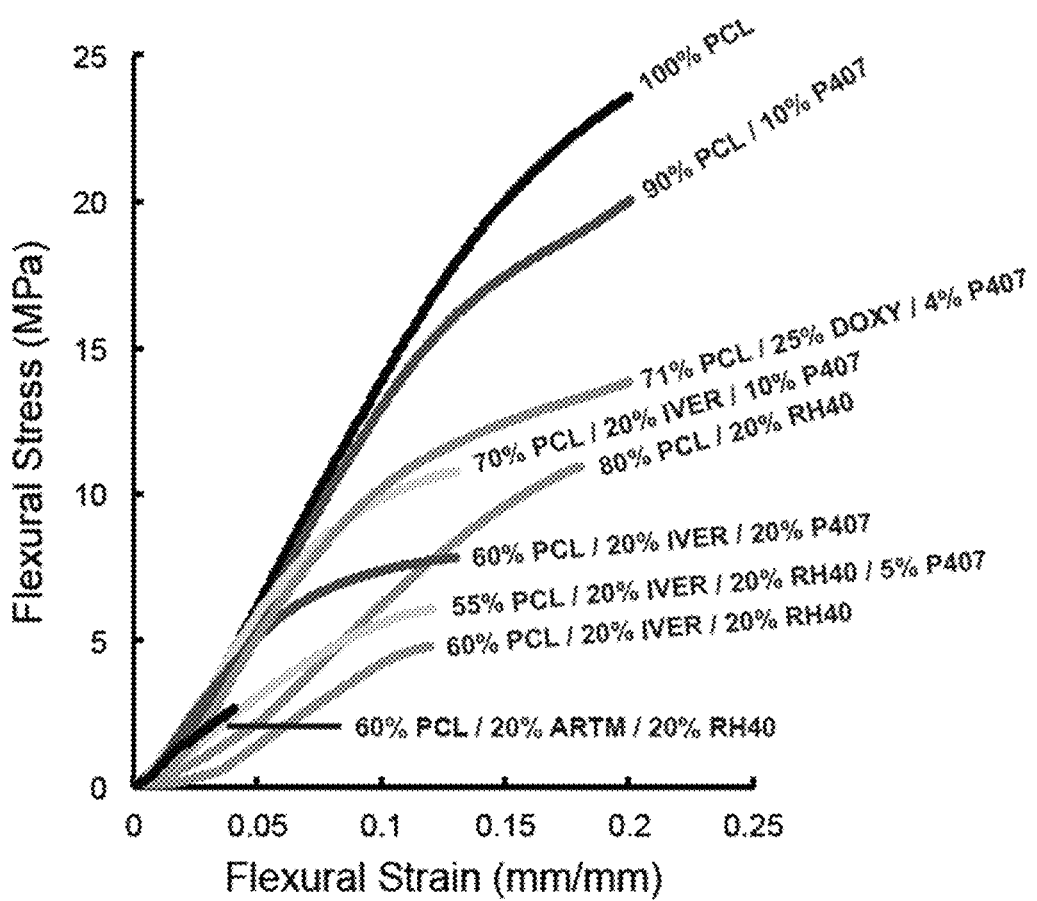
FIG. 18 is a plot that shows the mechanical characterization according to ASTM standard D790 of various PCL based materials, according to one set of embodiments.

Linear PCL was mechanically characterized in flexion according to ASTM standard D790, and shown in FIG. 18. Sheets of linear PCL, PCL with excipients, and PCL with excipients and drugs were cured into sheets 2 mm in thickness. The sheets were allowed to cool and then rectangles 80 mm length×8 mm width were cut out of the sheet to produce samples. A digital micrometer was used to measure the width and thickness of specimens prior to testing. An Instron testing machine fitted with a three-point bending fixture was used to test specimens. The test was conducted at a rate of 0.85 mm/min and a span of 32 mm was used for all specimens. The test was stopped when specimens failed or when they reached a flexural stain of 20%. Force was converted into flexural stress and displacement into flexural strain.

Example 14—Gastric Residence Times

Figure 19:
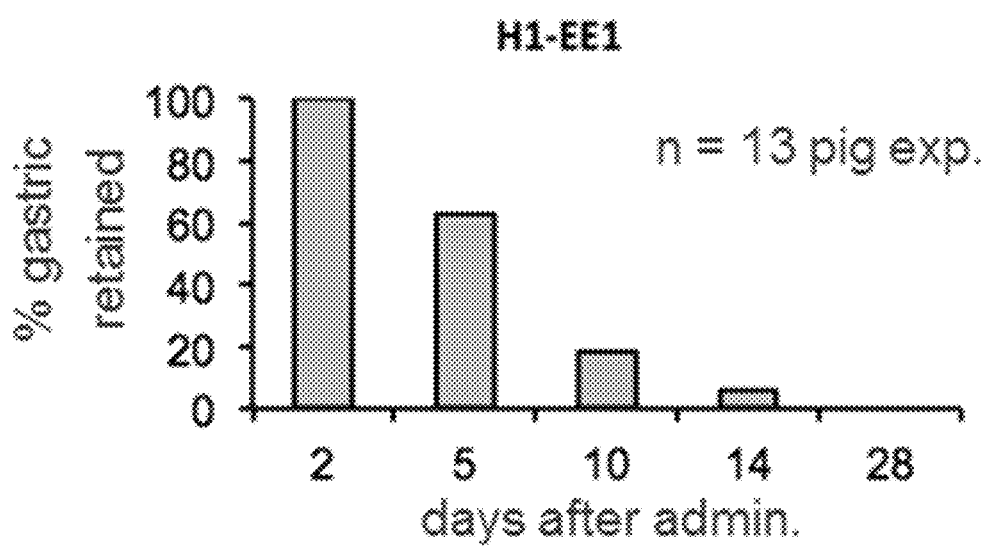
FIG. 19 is a plot that shows the probability of gastric retention at specified time points of a configurations of a gastric residence structure, according to one set of embodiments.
Figure 20:
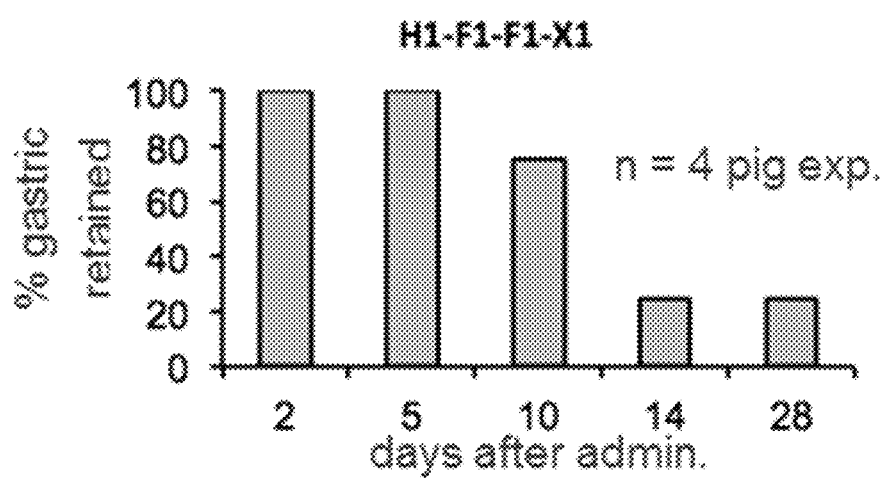
FIG. 20 is a plot that shows the probability of gastric retention at specified time points of a configurations of a gastric residence structure, according to one set of embodiments.
Figure 21:
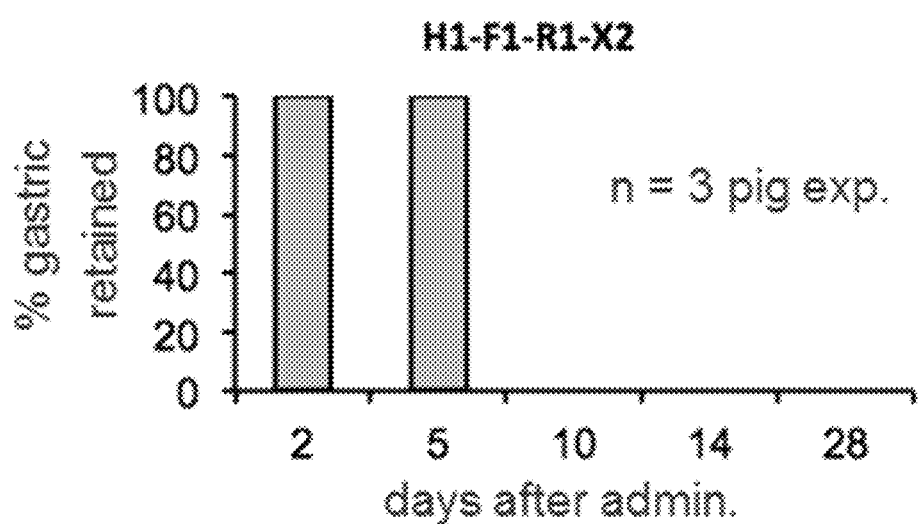
FIG. 21 is a plot that shows the probability of gastric retention at specified time points of a configurations of a gastric residence structure, according to one set of embodiments.

FIGS. 19-21 show histograms of the probability of gastric retention at specified time points of three different configurations of gastric residence systems. Gastric residence systems were formed with inclusion of stainless steel 1 mm fiducials placed in the polymeric drug delivery "arms" during polymerization of the arms. Gastric residence systems were administered to Yorkshire swine (35-50 kg) under sedation and through a endoscopic overtube into the gastric cavity. Serial radiographs were obtained in multiple positions (anteroposterior, left lateral, right lateral) of the chest, abdomen, and pelvis. Radiographs were taken after delivery for up to 15 minutes to confirm deployment from the outer capsule and/or restraining system. Radiographs were then obtained daily for the next 4 days and three times weekly after the first 5 days. Location of the residence system in the gastric cavity was confirmed from multiple radiographic views. (FIG. 19, H1-EE1) Hexagonal residence system with polycaprolactone "arms" and elastic elements at vertices made from enteric elastomer. (FIG. 20, H1-F1-F1-X1) Hexagonal residence system with arms made of isocyanate crosslinked polycaprolactone and elastic element made from isocyanate crosslinked polycaprolactone and with dissolvable linkers made of Eudragit L100-55 films. (FIG. 21, H1-F1-R1-X2) Hexagonal residence system with arms made of polycaprolactone and elastic elements made from isocyanate crosslinked polycaprolactone and dissolvable linkers made of a blend of 90% Eudragit L100-55 and 10% poly(acrylic acid).

Example 15—Passage of Food

Intra-gastric balloons (a gastric resident system which is deployed endoscopically) for the treatment of obesity has noted symptoms consistent with partial gastric outlet obstruction, specifically of nausea in the range of 18-90% of patients. To monitor the potential for gastric outlet obstruction in residence structures described herein, these structures were evaluated in a large animal model. Specifically a structure constructed primarily of non-degradable elastic polymeric components was prepared in a stellate configuration to observe potential outlet obstruction. This was deployed in the stomach of a ~50 kg pig which was monitored clinically twice a day for evidence of gastrointestinal obstruction including abdominal distension, vomiting and decreases feces production. Furthermore, serial x-rays were performed 3 times a week to evaluate for evidence of obstruction including gastric distension. Moreover at day 35 the animal was placed on a liquid diet for 24 hours prior to the endoscopic procedure to evaluate the animal's capacity for gastric emptying and the stomach evaluated endoscopically. On endoscopic imaging the structure was noted to overly the pylorus and the gastric cavity was devoid of food material supporting the capacity of the structure to allow for passage of food out of the stomach and yet remain resident in the stomach cavity and even overlying the pylorus.

Figure 22:
FIG. 22 is a reproduction of a photograph that shows endoscopic evaluation at day 35 of retention of a stellate delivery system, according to one set of embodiments.
Figure 23:
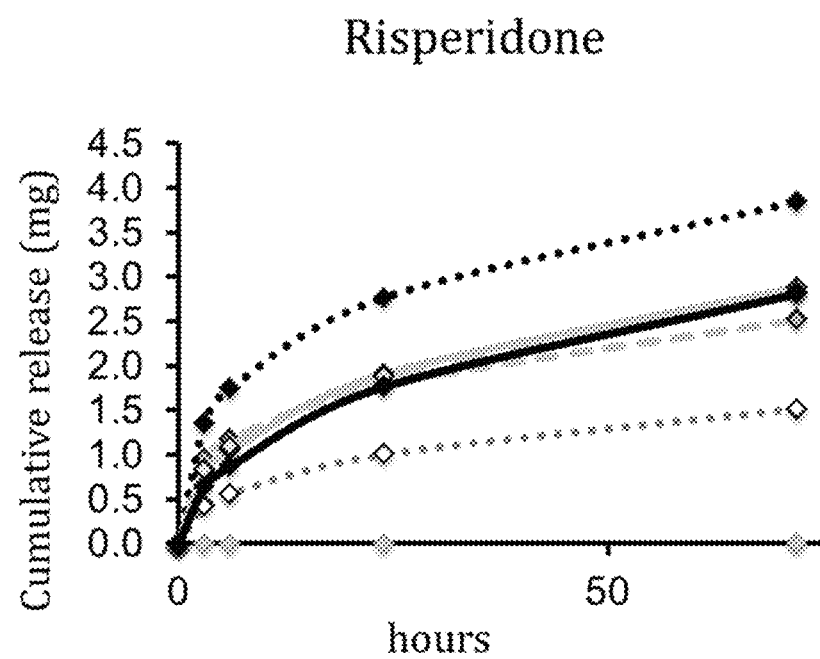
FIG. 23 is a plot that shows the cumulative release of risperidone over time for an exemplary residence structure, according to one set of embodiments.

FIG. 22 shows endoscopic evaluation at day 35 of retention of a stellate delivery system. In the image the delivery system is overlying the pylorus and a probe is in the field. As noted in the picture there appears to be no significant evidence of retained food and in fact the prototype is free of any entangled food particulates.

Example 16—In vivo Extended Oral Doxycycline Delivery

Figure 24:
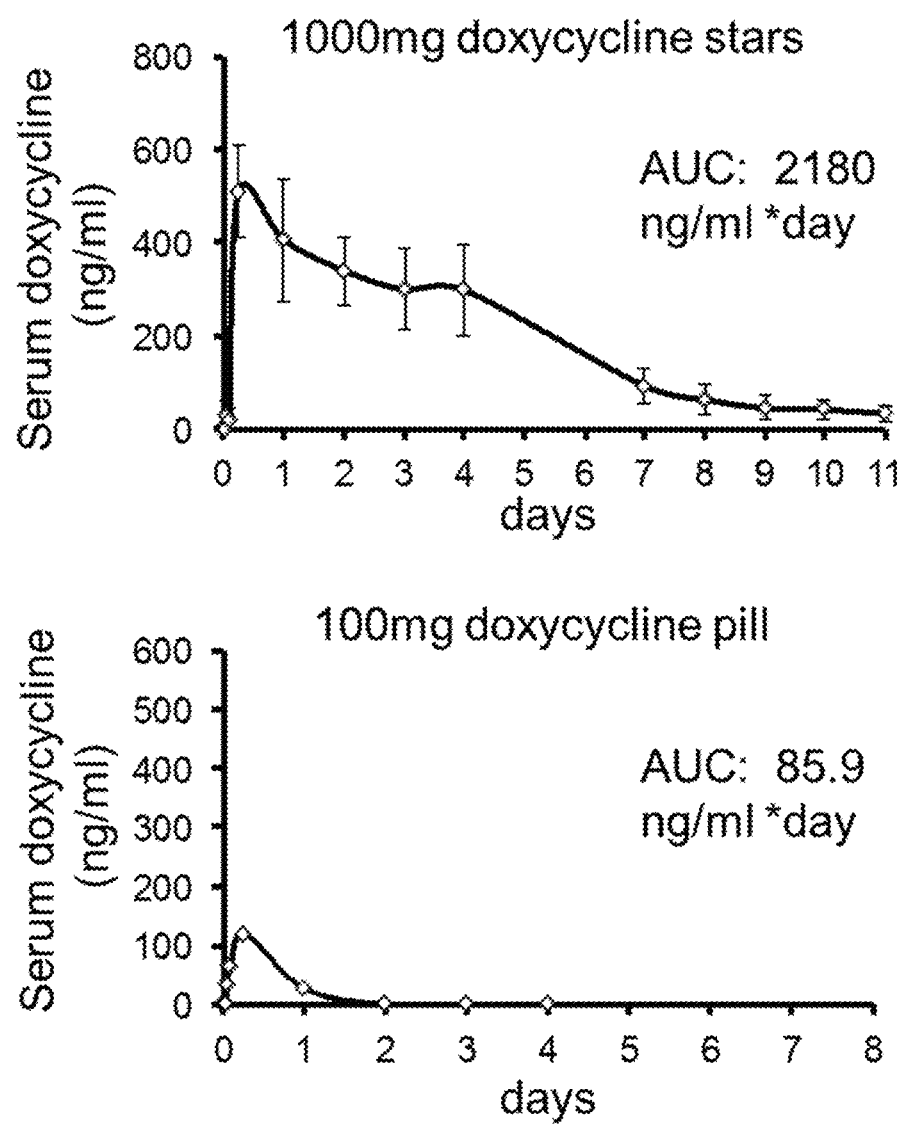
FIG. 24 are plots that show the release of doxycycline over time for an exemplary residence structure versus a doxycycline pill, according to one set of embodiments.

Doxycycline hyclate 100 mg commercially available tablets were purchased from a veterinary source (Patterson Veterinary). One tablet each was administered on Day 0 to three pigs and serum was collected from venous cannulation at the selected time points. Separate pigs were administered 6-armed star formulations of doxycycline totaling approximately 1000 mg intended to provide the same dosage as 100 mg twice daily for about 5 days. Doxycycline was formulated at 25% w/w loading in polycaprolactone 45,000 MW along with 4% w/w Pluronic P407 hydrophilic excipient. The blend was melted and mixed at 75 degrees Celsius and cast into PDMS molds. The central portion was removed from the star after cooling and elastic PCL prepolymer solution was poured into the central void and cured for 48 hours at approximately 75 degrees Celsius. The resulting shapes were encapsulated and administered to the Yorkshire pigs as previously described. Drug levels were quantified using LC/LC-MS, as shown in FIG. 24.

Example 17—In vivo Extended Oral Ivermectin Delivery

Figure 25A:
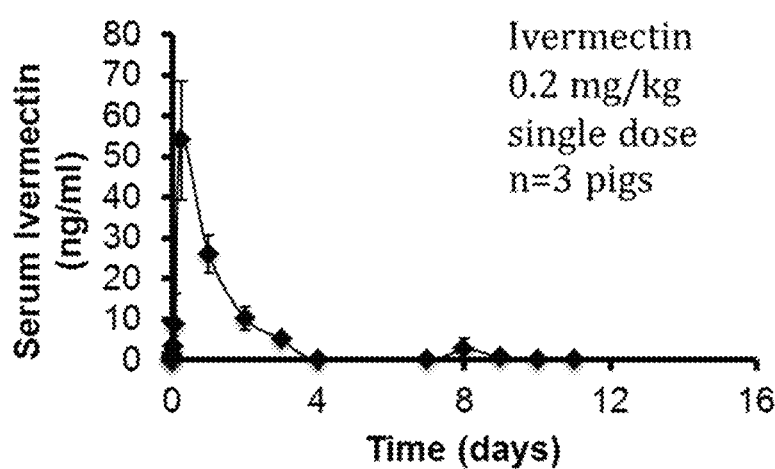
FIGS. 25A-C are plots that show the release of ivermectin over time for (A) an ivermectin pill, (B) a lower dose formulation, and (C) a higher dose formulation, according to one set of embodiments.

Ivermectin was dissolved in a 50:50 solution of EtoH and water and 0.2 mg/kg was administered to each 40-50 kg pig as an oral gavage in 10 ml of solution. Blood specimens from peripheral venous cannulation were collected in serum separator tubes at the indicated times before and after administration and centrifuged. Serum was frozen in aliquots for later batch analysis. Serum levels of ivermectin were measured on a Waters LC-MS using standard methods, as shown in FIG. 25A.

Figure 25B:
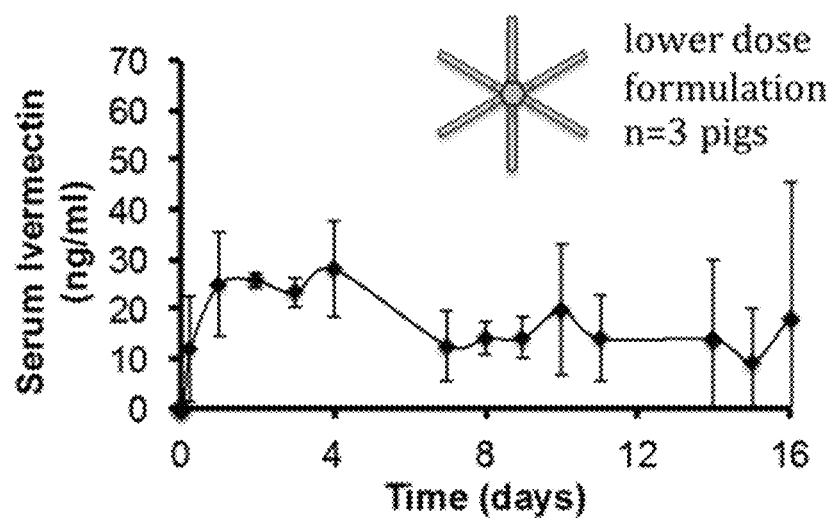

Ivermectin was loaded into polycaprolactone by first mixing ivermectin at 20% (w/w) of final mass with 10% (w/w) of the final mass Pluronic P407 poloxamer and briefly melting at 75 degrees celcius. Polycaprolactone 45,000 molecular weight (Sigma-Aldrich, St. Louis, Mo.) was then added (70% w/w) and the mixture was melted at 75 degrees C. for 20 minutes and mixed for 5 minutes. The molten mixture was transferred into a mold of the stellate design. The mold was heated to 90 degrees Celsius for 2 hours then air-cooled. Arm portions were prepared and placed back into the stellate mold leaving the central element as a void. Elastic PCL prepolymer solution was poured into the central elastic region and cured at 70 degree Celsius for 24 hours. Stellate shapes were removed from the mold and placed into 000 gelatin capsules. The capsules were administered via endoscopically placed esophageal overtube into the gastric cavity of sedated Yorkshire pigs. Three capsules, each containing about 200 mg of ivermectin embedded in the formulation, were administered to each of three pigs. Results are shown in FIG. 25B.

Figure 25C:
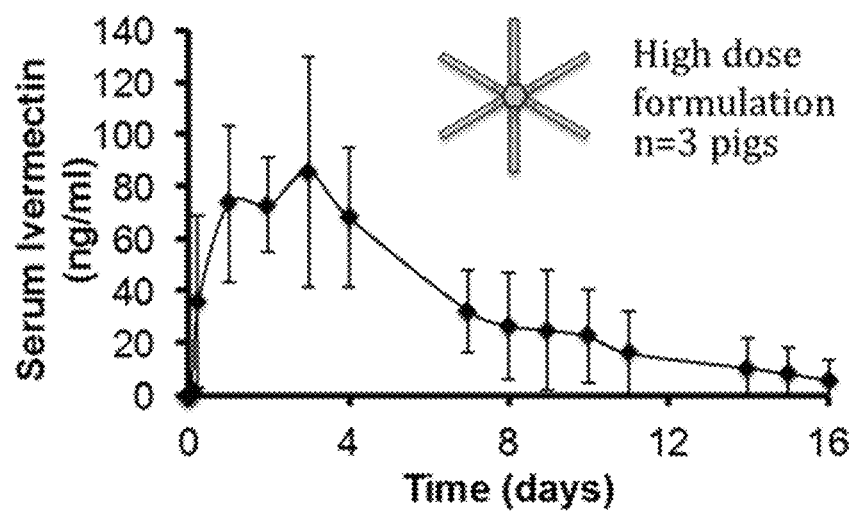
Figure 26:
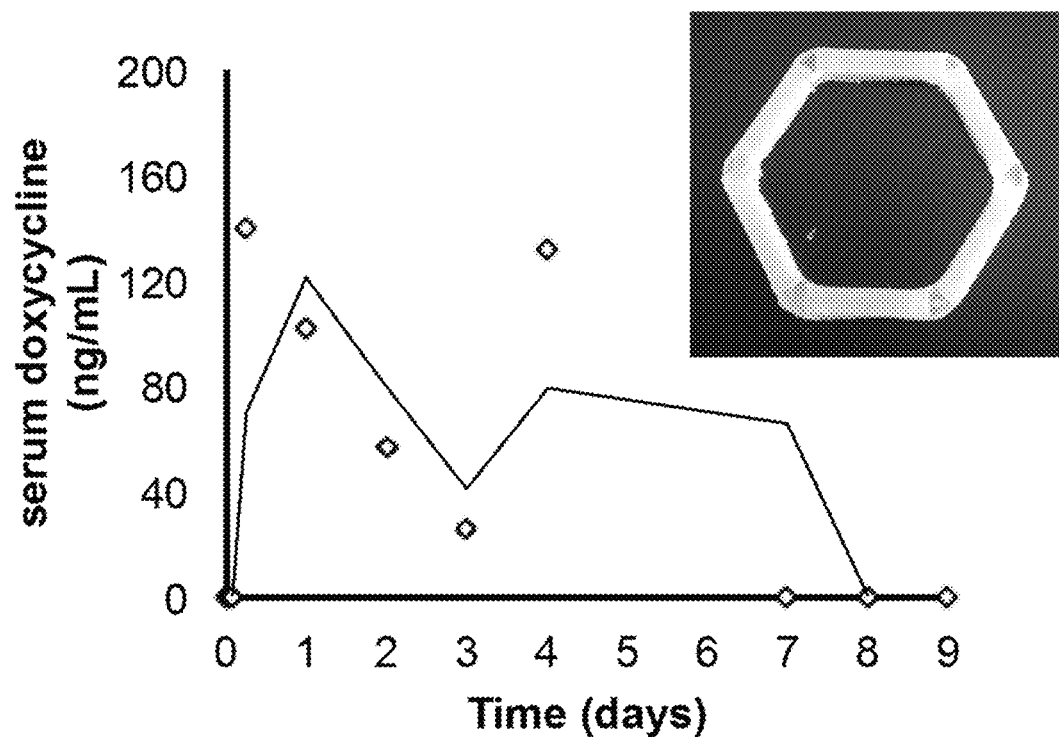
FIG. 26 is a plot that shows the release of doxycycline over time for an exemplary residence structure, according to one set of embodiments.

The elastic element was made as described above in specially made molds corresponding to the central elastic element. The ivermectin loaded element was made as described above for in FIG. 25B. The molten mixture was transferred into a mold of the stellate design into which the preformed elastic central element had been placed in position. The mold was heated to 90 degrees celcius for 2 hours then air-cooled. Stelllate shapes were removed from the mold and placed into 000 gelatin capsules. The capsules were administered via endoscopically placed esophageal overtube into the gastric cavity of sedated Yorkshire pigs. Ten capsules, each containing about 200 mg of ivermectin embedded in the formulation, were administered to each of three pigs. Results are shown in FIG. 25C.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of making a gastric residence structure comprising an active substance comprising:
    forming one or more arms comprising a loadable polymeric component, wherein the loadable polymeric component comprises one or more polymeric materials and at least one active substance; and
    connecting the one or more arms to an elastic polymeric component using a separate linker component;
    wherein the gastric residence structure is configured to be folded and physically constrained during administration and is configured to assume an open retention shape upon removal of a constraint, wherein change between the folded shape and the open retention shape is mediated by the elastic polymeric component that undergoes elastic deformation when the residence structure is in the folded shape and recoils when the gastric residence structure assumes the open retention shape; and
    wherein the linker degrades, dissolves, disassociates, or mechanically weakens in a gastric environment which results in loss of retention shape integrity and passage out of a gastric cavity.

2. The method of claim 1, wherein the loadable polymeric component comprises polycaprolactone (PCL).

3. The method of claim 1, wherein the loadable polymeric component comprises, poly(ethylene-co-vinyl acetate) or polyethylene glycol (PEG).

4. The method of claim 1, wherein the loadable polymeric component comprises at least 10 wt % active substance of the total weight of the loadable polymeric component.

5. The method of claim 1, wherein the loadable polymeric component comprises 10-50 wt % active substance of the total weight of the loadable polymeric component.

6. The method of claim 1, wherein the gastric residence structure comprises a plurality of active substances.

7. The method of claim 1, wherein the at least one active substance comprises a therapeutic agent or a diagnostic agent.

8. The method of claim 1, wherein the at least one active substance comprises an antiviral agent.

9. The method of claim 1, wherein the at least one active substance comprises an antiretroviral agent.

10. The method of claim 1, wherein the at least one active substance comprises an antipsychotic agent.

11. The method of claim 1, wherein the at least one active substance comprises an immunosuppresive agent.

12. The method of claim 1, wherein the at least one active substance comprises a neuroprotective agent.

13. The method of claim 1, wherein the at least one active substance comprises memantine.

14. The method of claim 1, wherein the at least one active substance comprises buprenorphine.

15. The method of claim 1, wherein the at least one active substance comprises risperidone.

16. The method of claim 1, wherein the linker component comprises an enteric polymer.

17. A method of making an orally administrable gastric residence system comprising an active substance comprising: forming one or more arms comprising a loadable polymeric component, wherein the loadable polymeric component comprises one or more polymeric materials and at least one active substance; and connecting the one or more arms to an elastic polymeric component using a separate linker component to form a gastric residence structure, said linker connecting the loadable polymeric component with the elastic polymeric component; wherein the gastric residence structure is configured to be folded and physically constrained during administration and is configured to assume an open retention shape upon removal of a constraint, wherein change between the folded shape and the open retention shape is mediated by the elastic polymeric component that undergoes elastic deformation when the residence structure is in the folded shape and recoils when the gastric residence structure assumes the open retention shape; wherein the linker degrades, dissolves, disassociates, or mechanically weakens in a gastric environment which results in loss of retention shape integrity and passage out of a gastric cavity; and inserting the gastric residence system in the folded shape into a capsule to form an administrable gastric residence system.

18. The method of claim 17, wherein forming a loadable polymeric component from one or more polymeric materials and at least one active substance comprises powder mixing, solvent loading, melt loading, or physical blending the one or more polymeric materials with the at least one active substance.

19. The method of claim 17, wherein the loadable polymeric component comprises polycaprolactone (PCL).

20. The method of claim 17, wherein the loadable polymeric component comprises poly(ethylene-co-vinyl acetate), or polyethylene glycol (PEG).

21. The method of claim 17, wherein the loadable polymeric component comprises at least 10 wt % active substance of the total weight of the loadable polymeric component.

22. The method of claim 17, wherein the loadable polymeric component comprises 10-50 wt % active substance of the total weight of the loadable polymeric component.

23. The method of claim 17, wherein the gastric residence structure comprises a plurality of active substances.

24. The method of claim 17, wherein the at least one active substance comprises a therapeutic agent or a diagnostic agent.

25. The method of claim 17, wherein the at least one active substance comprises an antiviral agent.

26. The method of claim 17, wherein the at least one active substance comprises an antiretroviral agent.

27. The method of claim 17, wherein the at least one active substance comprises an antipsychotic agent.

28. The method of claim 17, wherein the at least one active substance comprises an immunosuppresive agent.

29. The method of claim 17, wherein the at least one active substance comprises a neuroprotective agent.

30. The method of claim 17, wherein the at least one active substance comprises memantine.

31. The method of claim 17, wherein the at least one active substance comprises buprenorphine.

32. The method of claim 17, wherein the at least one active substance comprises risperidone.

33. The method of claim 17, wherein the linker component comprises an enteric polymer.

34. The method of claim 17, wherein the capsule is a 000 capsule, a 00 capsule, a 0 capsule, a 1 capsule, a 2 capsule, a 3 capsule, a 4capsule, or a 5 capsule.

35. A method of making a gastric residence structure comprising an active substance comprising:
forming one or more arms comprising a loadable polymeric component, wherein each polymeric component is formed from one or more polymeric materials and at least one active substance, and forming the loadable polymeric component comprises powder mixing, solvent loading, melt loading, or physical blending the one or more polymeric materials with the at least one active substance; and
connecting the one or more arms to an elastic polymeric component using a separate linker component;
wherein the gastric residence structure is configured to be folded and physically constrained during administration and is configured to assume an open retention shape upon removal of a constraint, wherein change between the folded shape and the open retention shape is mediated by the elastic polymeric component that undergoes elastic deformation when the residence structure is in the folded shape and recoils when the gastric residence structure assumes the open retention shape; and
wherein the linker degrades, dissolves, disassociates, or mechanically weakens in a gastric environment which results in loss of retention shape integrity and passage out of a gastric cavity.

36. The method of claim 35, wherein the loadable polymeric component comprises polycaprolactone (PCL).

37. The method of claim 35, wherein the loadable polymeric component comprises, poly(ethylene-co-vinyl acetate), or polyethylene glycol (PEG).

38. The method of claim 35, wherein the loadable polymeric component comprises at least 10 wt % active substance of the total weight of the loadable polymeric component.

39. The method of claim 35, wherein the loadable polymeric component comprises 10-50 wt % active substance of the total weight of the loadable polymeric component.

40. The method of claim 35, wherein the gastric residence structure comprises a plurality of active substances.

41. The method of claim 35, wherein the at least one active substance comprises a therapeutic agent or a diagnostic agent.

42. The method of claim 35, wherein the at least one active substance comprises an antiviral agent.

43. The method of claim 35, wherein the at least one active substance comprises an antiretroviral agent.

44. The method of claim 35, wherein the at least one active substance comprises an antipsychotic agent.

45. The method of claim 35, wherein the at least one active substance comprises an immunosuppresive agent.

46. The method of claim 35, wherein the at least one active substance comprises a neuroprotective agent.

47. The method of claim 35, wherein the at least one active substance comprises memantine.

48. The method of claim 35, wherein the at least one active substance comprises buprenorphine.

49. The method of claim 35, wherein the at least one active substance comprises risperidone.

50. The method of claim 35, wherein the linker component comprises an enteric polymer.

51. A method of making a gastric residence structure comprising an active substance comprising:
forming a plurality of loadable polymeric components, each loadable polymeric component being formed from one or more polymeric materials and at least one active substance; and
connecting each of the plurality of loadable polymeric components to a central elastic polymeric component using a separate linker component;
wherein the gastric residence structure is configured to be folded and physically constrained during administration and is configured to assume an open retention shape upon removal of a constraint, wherein change between the folded shape and the open retention shape is mediated by the central elastic polymeric component that undergoes elastic deformation when the residence structure is in the folded shape and recoils when the gastric residence structure assumes the open retention shape; and wherein the linker component degrades, dissolves, disassociates, or mechanically weakens in a gastric environment which results in loss of retention shape integrity and passage out of a gastric cavity.

52. The method of claim 51, wherein forming the plurality of loadable polymeric components comprises powder mixing, solvent loading, melt loading, or physical blending the one or more polymeric materials with the at least one active substance.

53. The method of claim 51, wherein the plurality of loadable polymeric components comprises at least three loadable polymeric components.

54. The method of claim 51, wherein the open retention shape is a multi-armed star shape.

55. The method of claim 51, wherein the plurality of loadable polymeric components comprise polycaprolactone (PCL).

56. The method of claim 51, wherein the plurality of loadable polymeric components comprise, poly(ethylene-co-vinyl acetate), or polyethylene glycol (PEG).

57. The method of claim 51, wherein the plurality of loadable polymeric components comprise at least 10 wt % active substance of the total weight of the plurality of loadable polymeric component.

58. The method of claim 51, wherein the plurality of loadable polymeric components comprise 10-50 wt % active substance of the total weight of the plurality of loadable polymeric components.

59. The method of claim 51, wherein the gastric residence structure comprises a plurality of active substances.

60. The method of claim 51, wherein the at least one active substance comprises a therapeutic agent or a diagnostic agent.

61. The method of claim 51, wherein the at least one active substance comprises an antiviral agent.

62. The method of claim 51, wherein the at least one active substance comprises an antiretroviral agent.

63. The method of claim 51, wherein the at least one active substance comprises an antipsychotic agent.

64. The method of claim 51, wherein the at least one active substance comprises an immunosuppresive agent.

65. The method of claim 51, wherein the at least one active substance comprises a neuroprotective agent.

66. The method of claim 51, wherein the at least one active substance comprises memantine.

67. The method of claim 51, wherein the at least one active substance comprises buprenorphine.

68. The method of claim 51, wherein the at least one active substance comprises risperidone.

69. The method of claim 51, wherein the linker component comprises an enteric polymer.

* * * * *

UNITED STATES PATENT AND TRADEMARK OFFICE
CERTIFICATE OF CORRECTION

PATENT NO. : 10,517,820 B2  
APPLICATION NO. : 16/379727  
DATED : December 31, 2019  
INVENTOR(S) : Andrew Bellinger et al.

Page 1 of 1

It is certified that error appears in the above-identified patent and that said Letters Patent is hereby corrected as shown below:

On the Title Page

Item (73) Assignees:
"Massachusetts Institute of Technology, Cambridge, MA (US); The Brigham and Women's Hospital, Inc., Boston, MA (US); Tokitae LLC, Bellevue, WA (US)"

Should read:
--Massachusetts Institute of Technology, Cambridge, MA (US); The Brigham and Women's Hospital, Inc., Boston, MA (US)--

Signed and Sealed this  
Twenty-fifth Day of February, 2020

Andrei Iancu  
*Director of the United States Patent and Trademark Office*